United States Patent
Kelley et al.

(10) Patent No.: US 7,741,033 B2
(45) Date of Patent: Jun. 22, 2010

(54) ELECTROCATALYTIC NUCLEIC ACID HYBRIDIZATION DETECTION

(75) Inventors: Shana Kelley, Boston, MA (US); Rahela Gasparac, Boston, MA (US); Melissa Lapierre-Devlin, Wakefield, MA (US); Bradford Taft, Medway, MA (US)

(73) Assignee: Trustees of Boston College, Chestnut Hill, MA (US)

( * ) Notice: Subject to any disclaimer, the term of this patent is extended or adjusted under 35 U.S.C. 154(b) by 882 days.

(21) Appl. No.: 10/913,925

(22) Filed: Aug. 6, 2004

(65) Prior Publication Data
US 2005/0084881 A1 Apr. 21, 2005

Related U.S. Application Data

(63) Continuation-in-part of application No. PCT/US2004/014788, filed on May 11, 2004.

(60) Provisional application No. 60/470,242, filed on May 13, 2003.

(51) Int. Cl.
C12Q 1/68 (2006.01)
C07H 21/02 (2006.01)
C07H 21/04 (2006.01)
(52) U.S. Cl. .................. 435/6; 536/23.1; 536/24.3
(58) Field of Classification Search .............. 435/6; 536/23.1, 24.3
See application file for complete search history.

(56) References Cited

U.S. PATENT DOCUMENTS

| | | | |
|---|---|---|---|
| 5,312,527 A | 5/1994 | Mikkelsen et al. | 204/153.12 |
| 5,968,745 A * | 10/1999 | Thorp et al. | 435/6 |
| 5,972,692 A | 10/1999 | Hashimoto et al. | 435/285.2 |
| 6,123,819 A | 9/2000 | Peeters | |
| 6,180,346 B1 * | 1/2001 | Thorp et al. | 204/403.15 |
| 6,221,586 B1 | 4/2001 | Barton et al. | 435/6 |
| 6,325,904 B1 | 12/2001 | Peeters | |
| 6,361,951 B1 | 3/2002 | Thorp et al. | 435/6 |
| 6,399,303 B1 | 6/2002 | Connolly | |
| 6,479,240 B1 | 11/2002 | Kayyem et al. | 435/6 |
| 6,593,090 B2 | 7/2003 | Connolly | |
| 7,361,470 B2 | 4/2008 | Kelley et al. | |
| 7,361,471 B2 | 4/2008 | Gerdes et al. | |
| 2002/0081588 A1 | 6/2002 | De Lumley-woodyear et al. | 435/6 |
| 2002/0084410 A1 | 7/2002 | Colbert et al. | |
| 2002/0158342 A1 | 10/2002 | Tuominen et al. | |
| 2003/0087277 A1 | 5/2003 | Fritzsche et al. | |
| 2003/0089899 A1 | 5/2003 | Lieber et al. | |
| 2003/0143571 A1 | 7/2003 | Sharp et al. | |
| 2003/0211637 A1 | 11/2003 | Schoeniger et al. | |
| 2004/0040840 A1 | 3/2004 | Mao et al. | |
| 2004/0072263 A1 | 4/2004 | Link et al. | |
| 2004/0106203 A1 | 6/2004 | Stasiak et al. | |
| 2004/0114445 A1 | 6/2004 | Occhipinti et al. | |
| 2004/0136866 A1 | 7/2004 | Pontis et al. | |
| 2009/0270266 A1 | 10/2009 | Kelley et al. | |

FOREIGN PATENT DOCUMENTS

| | | |
|---|---|---|
| AU | 758 063 B2 | 3/2003 |
| EP | 0 564 254 A | 10/1993 |
| WO | WO 96/06946 * | 3/1996 |
| WO | WO 99/67628 * | 12/1999 |
| WO | WO 02/074988 A2 | 9/2002 |
| WO | WO 02/079514 A1 | 10/2002 |
| WO | WO 2004/027093 A1 | 4/2004 |

OTHER PUBLICATIONS

Kelley et al; Single-base mismatch detection based on charge transduction through DNA, 1999, Nucleic Acids Res., 27, 4830-4837.*
Martin CR et al, Nanomaterials in analytical chemistry, 1998, Analytical Chemistry News & Features, pp. 322A-327 A.*
Ueno et al, Fabrication and electrochemical characterization of interdigitated nanoelectrode arrays, 2205, Electrochemistry Communications, 7, 161-165.*
Rogers et al , Using an elestomeric phasemask for sub-100 nm photolithography in the optical near field, 1997, Appl. Phys. Lett. 70, 2658-2660.*
Lee, Tris 2,2' bipyridyl ruthenium electrogenerated chemiluminscence in analytical science, Mikrochim. Acta, 1997, 127, 19-39.*
Maruyama et al, Detection of target DNA by electrochemical method, 2001, Sensors and Actuators B, 76, 215-219.*
Vercoutere and Akeson; "Biosensors for DNA sequence detection"; Current Op. in Chem. Biol.; (2002); 6: 816-822.
Millan, et al.; "Sequence-Selective Biosensor for DNA Based on Electroactive Hybridization Indicators"; Anal. Chem.; (1993); 65: 2317-2323.
Hashimoto, et al.; "Sequence-Specific Gene Detection with a Gold Electrode Modified with DNA Probes and an Electrochemically Active Dye"; Anal. Chem.; (1994); 66: 3830-3833.
Hashimoto, et al.; "Novel DNA sensor for electrochemical gene detection"; Anal. Chem.; (1994); 286: 219-224.
Xu, et al.; "Immobilization of DNA on an Aluminum(III) Alkanebisphosphonate Thin Film with Electrogenerated Chemiluminescent Detection"; J. Am. Chem. Soc.; (1994); 116: 8386-8387.

(Continued)

Primary Examiner—Stephen Kapushoc
Assistant Examiner—Narayan K Bhat
(74) Attorney, Agent, or Firm—Wolf, Greenfield & Sacks, P.C.

(57) ABSTRACT

The detection of specific nucleic acid sequences using electrochemical readout would permit the rapid and inexpensive detection and identification of bacterial pathogens and the analysis of human genes. A new assay developed for this purpose is described that harnesses an electrocatalytic process to monitor nucleic acid hybridization. Furthermore, the new assay when used on nanoscale electrodes, provides ultrasensitive detection of nucleic acids.

32 Claims, 16 Drawing Sheets

OTHER PUBLICATIONS

Liu, et al., "Voltammetric determination of sequence-specific DNA by electroactive intercalator on praphite electrode"; *Anal. Chem.*; (1996); 335: 239-243.

Napier, et al.; "Probing Biomolecule Recognition with Electron Transfer: Electrochemical Sensors for DNA Hybridization"; *Bioconj. Chem.*; (1997); 8: 906-913.

Ropp, et al.; "Site-sleective electron transfer form purines to electrocatalysts: voltammetric detection of a biologically relevant deletion in hybridized DNA duplexes"; *Chem. Biol.*; (1999); 6: 599-605.

Boon, et al.; Mutation detection by electrocatalysis at DNA-modified electrodes; *Nat. Biotech.*; (2000); 18: 1096-1100.

Armistead, et al.; "Electrochemical Detection of Gene Expression in Tumor Samples: Overexpression of Rak Nuclear Tyrosine Kinase"; (2002); *Bioconj. Chem.*; (2002); 13: 172-176.

Palecek, et al.; "Electrochemical biosensors for DNA hybridization and DNA damage"; *Biosens. Bioelectron.*; (1998); 13: 621-628.

Thorp, H. Holden; "Cutting out the middleman: DNA biosensors based on electrochemical oxidation"; *Trends in Biotechnology*; (1998); 16: 117-121.

Steel, et al.; "Electrochemical Quantitation of DNA Immobilized on Gold"; *Anal. Chem.*; (1998); 70: 4670-4677.

Kelley, et al.; Single-base mismatch detection based on charge transduction through DNA; *Nucleic Acids Research*; (1999); 27(24): 4830-4837.

Wang, Joseph; "Survey and Summary from DNA biosensors to gene chips"; *Nucleic Acids Research*; (2000); 28(16): 3011-3016.

International Search Report based on PCT/US04/14788 dated Jun. 24, 2005.

Coche-Guerente et al., Amplification of amperometric biosensor responses by electrochemical substrate recycling. 3. Theoretical and experimental study of the phenol-polyphenol oxidase system immobilized in Laponite hydrogels and layer-by-layer self-assembled structures. Anal Chem. Jul. 15, 2001;73(14):3206-18.

Beaucage et al., Deoxynucleoside phosphoramidites—A new class of key intermediates for deoxypolynucleotide synthesis. Tetrahedron Lett. 1981;22(20):1859-62.

Blaser, *Helicobacter pylori* and the pathogenesis of gastroduodenal inflammation. J Infect Dis. Apr. 1990;161(4):626-33. Review.

Cheng et al., Ultramicroelectrode ensembles. Comparison of experimental and theoretical responses and evaluation of electroanalytical detection limits. Anal Chem. 1989;61(7):762-6.

Finot et al., Performance of interdigitated nanoelectrodes for electrochemical DNA biosensor. Ultramicroscopy. Oct.-Nov. 2003;97(1-4):441-9.

Gasparac et al., Ultrasensitive electrocatalytic DNA detection at two- and three-dimensional nanoelectrodes. J Am Chem Soc. Oct. 6, 2004;126(39):12270-1.

Heaton et al., Electrostatic surface lasmon resonance: direct electric field-induced hybridization and denaturation in monolayer nucleic acid films and label-free discrimination of base mismatches. Proc Natl Acad Sci U S A. Mar. 27, 2001;98(7):3701-4. Epub Mar. 20, 2001.

Li et al., Carbon nanotube nanoelectrode array for ultrasensitive DNA detection. Nanoletters. 2003;3:597-602.

Li et al., Fabrication approach for molecular memory arrays. Appl Phys Lett. Jan. 27, 2003;82(4):645-7.

Li et al., Highly-ordered carbon nanotube arrays for electronics applications. Appl Phys Lett. 1999;75:367.

Malaquin et al., Nanoelectrode-based devices for electrical biodetection in liquid solution. Microelect Eng. Jun. 2004;73-74:887-92.

Mirkin et al., A DNA-based method for rationally assembling nanoparticles into macroscopic materials. Nature. Aug. 15, 1996;382(6592):607-9.

Nelson et al., Label-free detection of 16S ribosomal RNA hybridization on reusable DNA arrays using surface plasmon resonance imaging. Environ Microbiol. Nov. 2002;4(11):735-43.

Nelson et al., Surface plasmon resonance imaging measurements of DNA and RNA hybridization adsorption onto DNA microarrays. Anal Chem. Jan. 1, 2001;73(1):1-7.

Peterson et al., Hybridization of mismatched or partially matched DNA at surfaces. J Am Chem Soc. Dec. 11, 2002;124(49):14601-7.

Peterson et al., The effect of surface probe density on DNA hybridization. Nucleic Acids Res. Dec. 15, 2001;29(24):5163-8.

Pividori et al., Electrochemical genosensor design: immobilisation of oligonucleotides onto transducer surfaces and detection methods. Biosens Bioelectron. Aug. 2000;15(5-6):291-303.

Shi, Technologies for individual genotyping: detection of genetic polymorphisms in drug targets and disease genes. Am J Pharmacogenomics. 2002;2(3):197-205. Review.

Smalley, Chip senses trace DNA. Jul. 30/Aug. 6, 2003. TRN Mag. com. 2 pages.

Smith et al., Theory of the voltammetric response of electrodes of submicron dimensions. Violation of electroneutrality in the presence of excess supporting electrolyte. Anal Chem. 1993;65(23):3343-53.

Southern, DNA microarrays. History and overview. Methods Mol Biol. 2001;170:1-15. Review.

Taton et al., Scanometric DNA array detection with nanoparticle probes. Science. Sep. 8, 2000;289(5485):1757-60.

Wang et al., Electroactive beads for ultrasensitive DNA detection. Langmuir. 2003;19(4):989-91.

Wang et al., Origins of high sequence selectivity: a stopped-flow kinetics study of DNA/RNA hybridization by duplex- and triplex-forming oligonucleotides. Biochemistry. Aug. 1, 1995;34(30):9774-84.

Ferain et al., Track-etch templates designed for micro- and nanofabrication. Nucl Instrum Meth Phys Res Sec B. Aug. 1, 2003;208:115-22.

Koehne et al., Ultrasensitive label-free DNA analysis using an electronic chip based on carbon nanotube nanoelectrode arrays. Nanotechnology. Dec. 1, 2003; 14(12):1239-45.

Lapierre-Devlin et al., Amplified electrocatalysis at DNA-modified nanowires. Nano Lett. Jun. 2005;5(6):1051-5.

\* cited by examiner

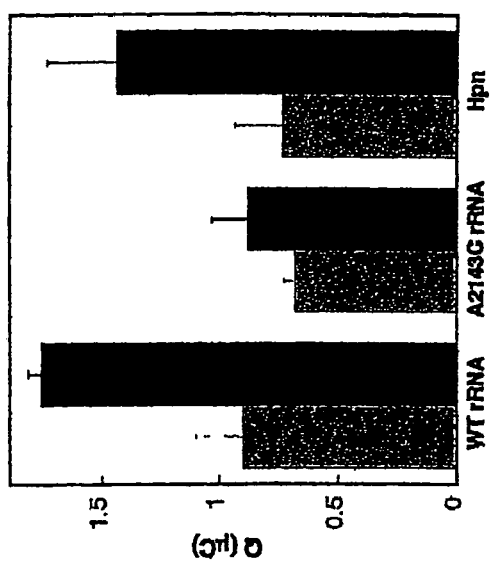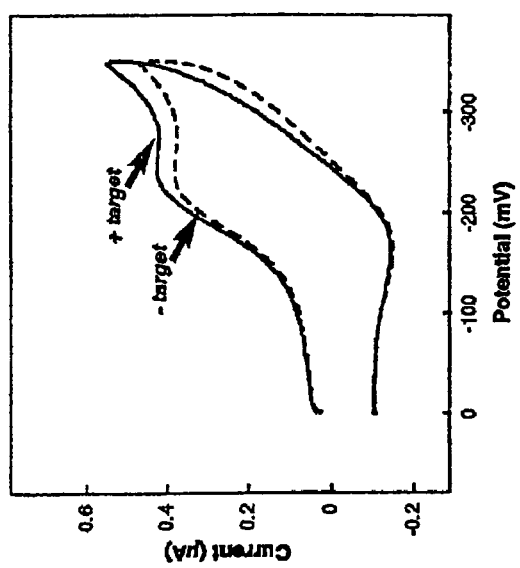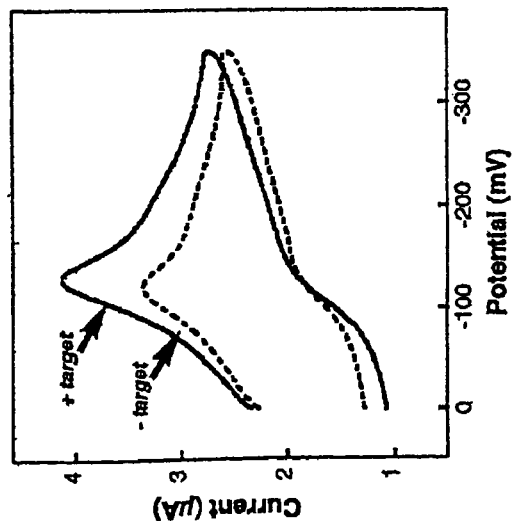

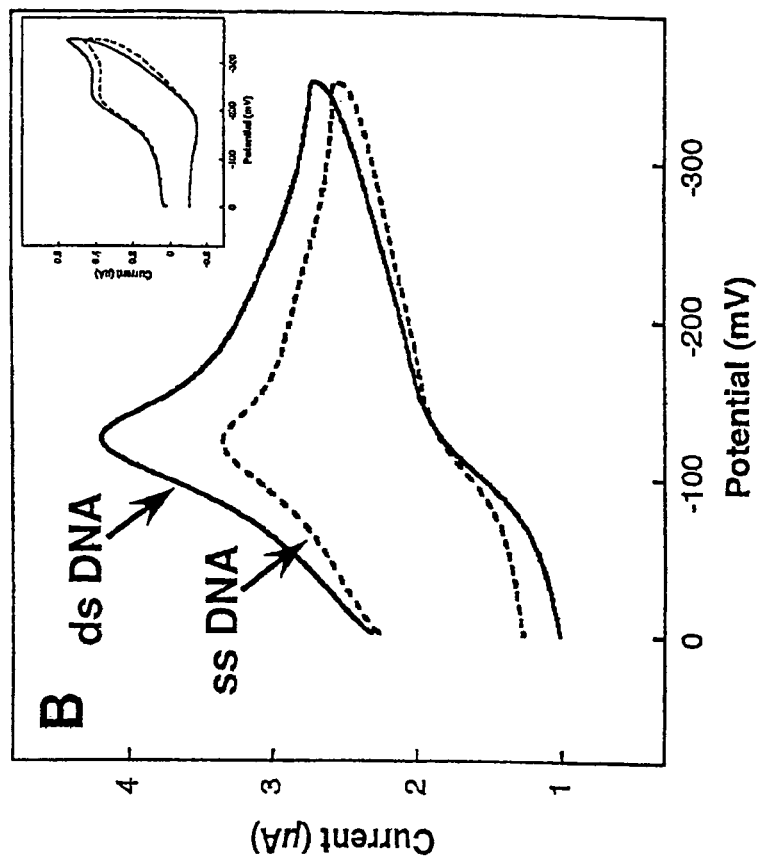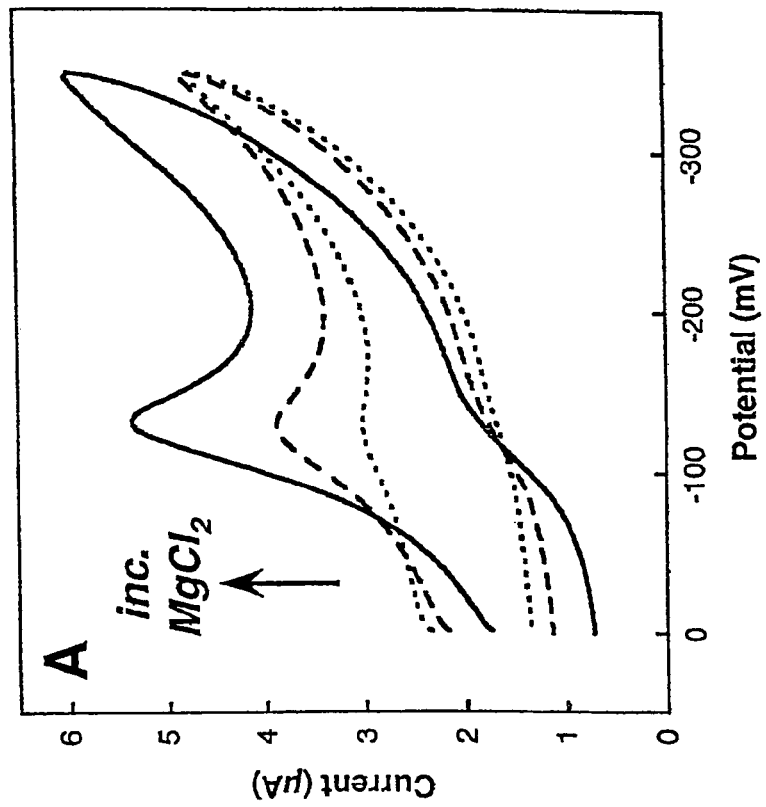
Figure 8

Figure 13A
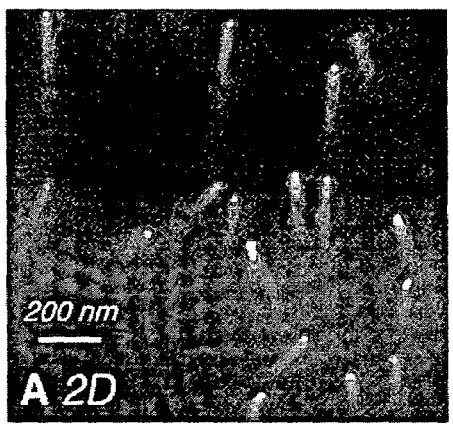 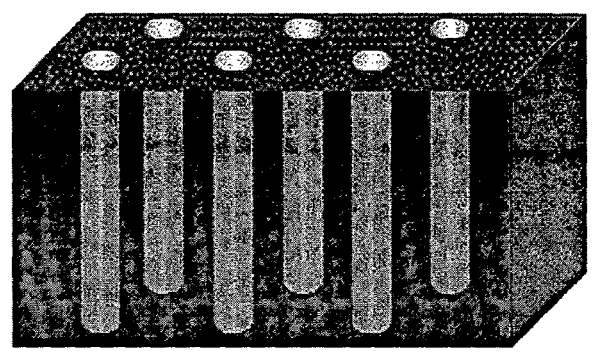
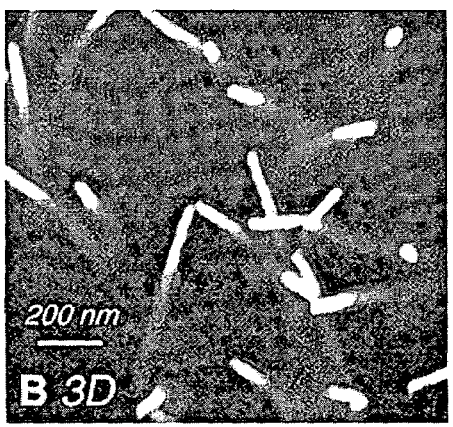 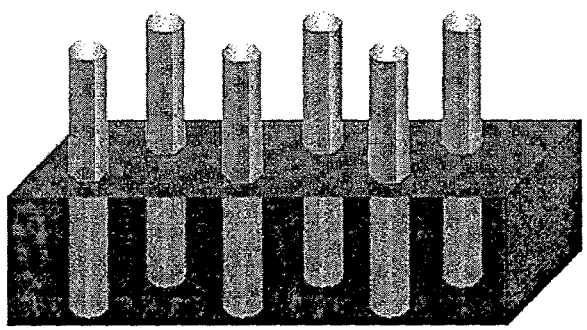

```
SEQUENCE LISTING

<160> NUMBER OF SEQ ID NOS: 20

<210> SEQ ID NO 1
<211> LENGTH: 30
<212> TYPE: DNA
<213> ORGANISM: Artificial sequence
<220> FEATURE:
<223> OTHER INFORMATION: T1 (hpn target)

<400> SEQUENCE: 1
tgttgcagca ctagcgatag tcatcatcaa                                        30

<210> SEQ ID NO 2
<211> LENGTH: 18
<212> TYPE: DNA
<213> ORGANISM: Artificial sequence
<220> FEATURE:
<223> OTHER INFORMATION: T2a (WT rRNA target)

<400> SEQUENCE: 2
ggcaagacgg aaagaccc                                                     18

<210> SEQ ID NO 3
<211> LENGTH: 18
<212> TYPE: DNA
<213> ORGANISM: Artificial sequence
<220> FEATURE:
<223> OTHER INFORMATION: T2aMUT (A2143C rRNA target)

<400> SEQUENCE: 3
ggcaagacgg acagaccc                                                     18
```

<210> SEQ ID NO 4
<211> LENGTH: 30
<212> TYPE: DNA
<213> ORGANISM: Artificial sequence
<220> FEATURE:
<223> OTHER INFORMATION: HP1b (18 nt + 12T complementary hpn probe)

<400> SEQUENCE: 4
tttttttttt ttgatgacta tcgctagtgc                                          30

<210> SEQ ID NO 5
<211> LENGTH: 30
<212> TYPE: DNA
<213> ORGANISM: Artificial sequence
<220> FEATURE:
<223> OTHER INFORMATION: HP1c (18 nt + 12T noncomplementary hpn probe)

<400> SEQUENCE: 5
tttttttttt ttgggataat tcttcaccgg                                          30

<210> SEQ ID NO 6
<211> LENGTH: 219
<212> TYPE: DNA
<213> ORGANISM: Artificial sequence
<220> FEATURE:
<223> OTHER INFORMATION: Target sequence (PCR product)

<400> SEQUENCE: 6
ggagtcatca tggcacacca tgaagaacag cacggcggtc atcaccacca tcaccaccac         60
acacaccacc accactatca cggcggtgaa caccaccatc accaccacag ctctcatcat        120
gaagaaggtt gttgcagcac tagcgatagt catcatcatc aagaagaggg ttgctgccac        180
gggcatcacg agtaatatcg gtgtggctag gggcaactt                               219

<210> SEQ ID NO 7
<211> LENGTH: 225
<212> TYPE: DNA
<213> ORGANISM: Artificial sequence
<220> FEATURE:
<223> OTHER INFORMATION: Target sequence (RNA transcript)

<400> SEQUENCE: 7
atcaaaggag tcatcatggc acaccatgaa gaacagcacg gcggtcatca ccaccatcac         60
caccacacac accaccacca ctatcacggc ggtgaacacc accatcacca ccacagctct        120
catcatgaag aaggttgttg cagcactagc gatagtcatc atcatcaaga agagggttgc        180
tgccacgggc atcacgagta atatcggtgt ggctaggggc aactt                        225

<210> SEQ ID NO 8
<211> LENGTH: 33
<212> TYPE: DNA
<213> ORGANISM: Artificial sequence
<220> FEATURE:
<223> OTHER INFORMATION: 30-mer oligonucleotide for Hpn target detection

<400> SEQUENCE: 8
tgttgcagca ctagcgatag tcatcatcat caa                                      33

<210> SEQ ID NO 9
<211> LENGTH: 24
<212> TYPE: DNA
<213> ORGANISM: Artificial sequence
<220> FEATURE:
<223> OTHER INFORMATION: Forward PCR primer for H. pylori hpn gene
      amplification

```
<400> SEQUENCE: 9
atcaaaggag tcatcatggc acac                                          24

<210> SEQ ID NO 10
<211> LENGTH: 18
<212> TYPE: DNA
<213> ORGANISM: Artificial sequence
<220> FEATURE:
<223> OTHER INFORMATION: Reverse PCR primer for H. pylori hpn gene
      amplification

<400> SEQUENCE: 10
aagttgcccc tagccaca                                                 18

<210> SEQ ID NO 11
<211> LENGTH: 41
<212> TYPE: DNA
<213> ORGANISM: Artificial sequence
<220> FEATURE:
<223> OTHER INFORMATION: Forward PCR primer containing the T7 polymerase
      promoter sequence

<400> SEQUENCE: 11
gctaggtaat acgactcact ataggagtca tcatggcaca c                       41

<210> SEQ ID NO 12
<211> LENGTH: 30
<212> TYPE: DNA
<213> ORGANISM: Artificial sequence
<220> FEATURE:
<223> OTHER INFORMATION: HP1a (30 nt complementary hpn probe):

<400> SEQUENCE: 12
ttgatgatga ctatcgctag tgctgcaaca                                    30

<210> SEQ ID NO 13
<211> LENGTH: 18
<212> TYPE: DNA
<213> ORGANISM: Artificial sequence
<220> FEATURE:
<223> OTHER INFORMATION: HP2a (rRNA probe)

<400> SEQUENCE: 13
gggtctttcc gtcttgcc                                                 18

<210> SEQ ID NO 14
<211> LENGTH: 18
<212> TYPE: DNA
<213> ORGANISM: Artificial sequence
<220> FEATURE:
<223> OTHER INFORMATION: HP2b (rRNA probe-2)

<400> SEQUENCE: 14
ggtccacggg gtctttcc                                                 18

<210> SEQ ID NO 15
<211> LENGTH: 18
<212> TYPE: DNA
<213> ORGANISM: Artificial sequence
<220> FEATURE:
<223> OTHER INFORMATION: T2b (WT rRNA target #2)

<400> SEQUENCE: 15
ggaaagaccc cgtggacc                                                 18
```

```
<210> SEQ ID NO 16
<211> LENGTH: 18
<212> TYPE: DNA
<213> ORGANISM: Artificial sequence
<220> FEATURE:
<223> OTHER INFORMATION: T2bMUT (A2143C rRNA target #2)

<400> SEQUENCE: 16
ggacagaccc cgtggacc                                                18

<210> SEQ ID NO 17
<211> LENGTH: 15
<212> TYPE: DNA
<213> ORGANISM: Artificial sequence
<220> FEATURE:
<223> OTHER INFORMATION: T-NC (noncomplementary target)

<400> SEQUENCE: 17
aacagttcct gcatg                                                   15

<210> SEQ ID NO 18
<211> LENGTH: 18
<212> TYPE: DNA
<213> ORGANISM: Helicobacter pylori

<400> SEQUENCE: 18
gggtctttcc gtcttgcc                                                18

<210> SEQ ID NO 19
<211> LENGTH: 18
<212> TYPE: DNA
<213> ORGANISM: Helicobacter pylori

<400> SEQUENCE: 19
ggcaagacgg aaagaccc                                                18

<210> SEQ ID NO 20
<211> LENGTH: 18
<212> TYPE: DNA
<213> ORGANISM: Helicobacter pylori

<400> SEQUENCE: 20
gcactagcga tagtcatc                                                18
```

ELECTROCATALYTIC NUCLEIC ACID HYBRIDIZATION DETECTION

PRIORITY CLAIM

This application is a continuation-in-part of international Application Serial No. PCT/US2004/014788, which designated the United States and was filed on May 11, 2004, which application claims priority to provisional U.S. Application No. 60/470,242, filed on May 13, 2003. The entire teachings of the above applications are incorporated herein by reference.

GOVERNMENT SUPPORT

The invention was partly supported by the National Institutes of Health and partly supported by DARPA and AFOSR. The Government has certain rights in the invention.

BACKGROUND

The application of newly available genetic information to advances in preventative medicine and disease treatment requires efficient and accurate DNA detection technologies.[1,2] One focus of recent technological developments is systems that exploit differential DNA hybridization at solid surfaces.[3-6] In theory, hybridization of target sequences representing microbial genomic fragments or human disease-related genes to immobilized probe sequences would permit high-sensitivity and high-throughput DNA detection. Moreover, if closely related sequences could be discriminated, microbial pathogens could be detected and identified.

A variety of spectroscopic and analytical techniques can be used to detect DNA hybridization at surfaces.[7-22] DNA-modified gold nanoparticles can be used to detect DNA sequences using optical and fluorescence spectroscopy.[12,18] Surface plasmon resonance also provides a means to monitor hybridization of target sequences to DNA-modified gold substrates in real time.[3,4,19,20,22] The results obtained with these methods indicate that high-sensitivity DNA detection can be achieved when immobilized oligonucleotides are used to capture sequences from solution.

Other gene detection methods (e.g., U.S. Pat. No. 5,972,692, and U.S. Pat. No. 5,312,527) do not use an electrocatalytic assay for DNA hybridization detection.

The detection of DNA sequences using electrochemical readout is particularly attractive for the development of clinical diagnostics.[2,6,23,24] Quantitative electrochemical measurements of this type can be made using compact and inexpensive instrumentation, and covalently labeling DNA samples with reporter groups is typically unnecessary, simplifying sample preparation procedures. Indeed, a number of methods have been reported for the electrochemical detection of DNA, most of which rely on the signal produced by a noncovalently bound redox-active reporter group that is increased when DNA is hybridized to a surface modified with a probe sequence.[7-11,13,15,21] In addition, single-base substitutions producing base mismatches within DNA duplexes immobilized on gold surfaces can be detected electrochemically using intercalating probes.[14,16] The interruption of base stacking caused by the mismatch attenuates the current flowing to the reporter by interfering with DNA-mediated electronic coupling. This effect would potentially permit the electrochemical detection of disease-related point mutations.

Electrocatalytic processes that amplify the signals obtained at DNA-modified electrode surfaces provide a powerful means to increase the sensitivity and accuracy of a detection assay. Electrochemically-generated $Ru(bpy)_3^{3+}$ reacts with guanines contained within a hybridized target in a catalytic process that generates large signals that can be used to detect DNA hybridization, albeit with limitations because of sequence dependence.[13,15,21,24] In addition, an electrocatalytic reaction between an intercalating probe, methylene blue, and solution-borne $Fe(CN)_6^{3-}$ has been used to amplify the signal changes reporting the presence of mismatch-producing point mutations.[16] However, neither system is ideal for hybridization-based detection of closely related sequences.

SUMMARY OF THE INVENTION

The invention relates to a new electrocatalytic nucleic acid detection assay that reports nucleic acid hybridization between a nucleic acid probe and a nucleic acid, or between a first nucleic acid and a second nucleic acid, and can resolve single-base changes in a target nucleic acid sequence. The method exploits a reaction between a redox pair comprising a nucleic acid-binding compound and a redox-active probe. The nucleic acid-binding compound comprises a redox active compound that can bind to the nucleic acid electrostatically and can be reduced at low potential. This compound is bound to the nucleic acid, producing an electrostatically bound complex. The signal generated by the binding can be amplified by use of a redox active probe that can reoxidize the electrostatically bound complex.

The nucleic acid-binding compound can be a transition metal complex. Preferably, the transition metal is one selected from the group consisting of cobalt, iron, molybdenum, osmium, ruthenium and rhenium. Also preferably, the transition metal complex is an ammonium complex of the transition metal. More preferably, the transition metal complex is $Ru(NH_3)_6^{3+}$. The redox active probe can also be a transition metal complex. Preferably, the transition metal is one selected from the group consisting of cobalt, molybdenum, iridium, osmium, iron and rhenium. Also preferably, the transition metal complex is a cynate or choloride complex of the transition metal. More preferably, the transition metal complex is $Fe(CN)_6^{-3}$. More preferably, the second transition metal complex is iridium chloride complex, preferably with iridium in its oxidative states ranging from +3 to +6 states. Preferably, the iridium chloride complex is $IrCl_6^{-2}$ or $IrCl_6^{-3}$.

Alternatively, the redox active can also be an organic molecule such as ascorbic acid or tripropylamine.

The nucleic acid-binding compound binds to the nucleic acid primarily through electrostatic interactions with the phosphate backbone, and therefore its electrochemical reduction yields a signal that reports on the increase of negatively charged groups at the electrode surface upon hybridization of a target nucleic acid. The signal is amplified by the transition metal or organic oxidant of the redox active probe which permits the transition metal to be regenerated for multiple cycles. The immobilization of the nucleic acid probe on highly conductive surfaces, e.g., gold, amplifies the kinetic effects of base mismatches on nucleic acid hybridization, permitting single-base changes to be resolved.

The assay of the present invention can be used to detect genes from pathogens, such as bacteria or viruses, or can be used to detect the expression of genes in a subject.

Preferably, the method is used to detect hybridization between two nucleic acid molecules. The invention also includes a method for detecting hybridization between two DNA or RNA molecules, or between DNA and RNA molecules.

The invention features a method of detecting nucleic acid hybridization between a nucleic acid probe and a target nucleic acid in a sample, where the method includes the steps of: (a) providing a nucleic acid probe immobilized on a solid substrate; (b) contacting, under hybridizing conditions, the solid support and the immobilized probe to a solution containing the sample and a redox pair, wherein the redox pair comprises a first transition metal complex and a second transition metal complex; and (c) measuring the electrocatalytic signal generated by hybridization of the nucleic acid probe and the target nucleic acid; where an increase of the signal detected in step (c) relative to that of a control sample containing no nucleic acid, indicates that the nucleic acid hybridization has occurred. The method can also include an additional step of testing a control, by contacting, under hybridizing conditions, the solid support and the immobilized nucleic acid probe to a solution containing no sample, and a redox pair comprising a first transition metal complex and a second transition metal complex.

Preferably, the transition metal of the first transition metal complex is one selected from the group consisting of cobalt, iron, molybdenum, osmium, ruthenium and rhenium. More preferably, the transition metal of the first transition metal complex is ruthenium. Also preferably, the first transition metal complex is a transition metal ammonium complex. More preferably, the first transition metal ammonium complex comprises a transition metal selected from the group consisting of cobalt, iron, molybdenum, osmium, ruthenium and rhenium. Most preferably, the transition metal ammonium complex is $Ru(NH_3)_6^{3+}$.

Preferably, the transition metal of the second transition metal complex is one selected from the group consisting of cobalt, iron, molybdenum, iridium, osmium and rhenium. More preferably, the transition metal of the second transition metal complex is iron or iridium. Also preferably, the second transition metal complex is a transition metal cynate complex. More preferably, the second transition metal cynate complex comprises a transition metal selected from the group consisting of cobalt, iron, molybdenum, iridium, osmium and rhenium. Most preferably, the second transition metal cynate complex is $Fe(CN)_6^{-3}$. Also preferably, the second transition metal complex is a transition metal chloride complex. More preferably, the second transition metal chloride complex comprises a transition metal selected from the group consisting of cobalt, iron, molybdenum, iridium, osmium and rhenium. More preferably, the second transition metal complex is iridium chloride complex, preferably with iridium in its oxidative states ranging from +3 to +6 states. Preferably, the iridium chloride complex is $IrCl_6^{-2}$ or $IrCl_6^{-3}$.

The invention also features a method of detecting nucleic acid hybridization between a first nucleic acid and a second nucleic acid, wherein the method includes the steps of: (a) providing the first nucleic acid immobilized on a solid support; (b) contacting, under hybridizing conditions, the solid support and the immobilized first nucleic acid to a solution suspected of containing the second nucleic acid and a redox pair comprising a first transition metal complex and a second transition metal complex; and (c) measuring the electrocatalytic signal generated by hybridization of the first and second nucleic acids; wherein an increase of the signal detected in step (c) relative to that of an unhybridized first nucleic acid, indicates that nucleic acid hybridization has occurred. The method can also include an additional step of testing a control, by contacting, under hybridizing conditions, the solid support and the immobilized first nucleic acid to a solution containing no sample, and a redox pair comprising a first transition metal complex and a second transition metal complex.

Preferably, the transition metal of the first transition metal complex is one selected from the group consisting of cobalt, iron, molybdenum, osmium, ruthenium and rhenium. More preferably, the transition metal of the first transition metal complex is ruthenium. Also preferably, the first transition metal complex is a transition metal ammonium complex. More preferably, the first transition metal ammonium complex comprises a transition metal selected from the group consisting of cobalt, iron, molybdenum, osmium, ruthenium and rhenium. Most preferably, the transition metal ammonium complex is $Ru(NH_3)_6^{3+}$.

Preferably, the transition metal of the second transition metal complex is one selected from the group consisting of cobalt, iron, molybdenum, iridium, osmium and rhenium. More preferably, the transition metal of the second transition metal complex is iron or iridium. Also preferably, the second transition metal complex is a transition metal cynate complex. More preferably, the second transition metal cynate complex comprises a transition metal selected from the group consisting of cobalt, iron, molybdenum, iridium, osmium and rhenium. Most preferably, the second transition metal cynate complex is $Fe(CN)_6^{-3}$. Also preferably, the second transition metal complex is a transition metal chloride complex. More preferably, the second transition metal chloride complex comprises a transition metal selected from the group consisting of cobalt, iron, molybdenum, iridium, osmium and rhenium. More preferably, the second transition metal complex is iridium chloride complex, preferably with iridium in its oxidative states ranging from +3 to +6 states. Preferably, the iridium chloride complex is $IrCl_6^{-2}$ or $IrCl_6^{-3}$.

In another aspect, the invention features a method of detecting a mismatch between a first nucleic acid and a second nucleic acid, comprising: (a) providing a nucleic acid probe immobilized on a solid support; (b) contacting, under hybridizing conditions, the solid support and the immobilized probe to a solution containing the sample containing a target nucleic acid and a redox pair, wherein the redox pair comprises a first transition metal complex and a second transition metal complex; and (c) measuring the electrocatalytic signal generated by hybridization of the nucleic acid probe and the target nucleic acid; wherein a decrease of the signal detected in step (c) relative to that of a perfect complementarity between the nucleic acid probe and the target nucleic acid, indicates that there is a mismatch between the first nucleic acid and the second nucleic acid. The method can also include an additional step of testing a control, by contacting, under hybridizing conditions, the solid support and the immobilized nucleic acid probe to a solution containing no sample, and a redox pair comprising a first transition metal complex and a second transition metal complex.

Preferably, the transition metal of the first transition metal complex is one selected from the group consisting of cobalt, iron, molybdenum, osmium, ruthenium and rhenium. More preferably, the transition metal of the first transition metal complex is ruthenium. Also preferably, the first transition metal complex is a transition metal ammonium complex. More preferably, the first transition metal ammonium complex comprises a transition metal selected from the group consisting of cobalt, iron, molybdenum, osmium, ruthenium and rhenium. Most preferably, the transition metal ammonium complex is $Ru(NH_3)_6^{3+}$.

Preferably, the transition metal of the second transition metal complex is one selected from the group consisting of cobalt, iron, molybdenum, iridium, osmium and rhenium. More preferably, the transition metal of the second transition metal complex is iron or iridium. Also preferably, the second transition metal complex is a transition metal cynate complex. More preferably, the second transition metal cynate complex comprises a transition metal selected from the group consisting of cobalt, iron, molybdenum, iridium, osmium and rhenium. Most preferably, the second transition metal cynate complex is $Fe(CN)_6^{-3}$. Also preferably, the second transition metal complex is a transition metal chloride complex. More preferably, the second transition metal chloride complex comprises a transition metal selected from the group consisting of cobalt, iron, molybdenum, iridium, osmium and rhenium. More preferably, the second transition metal complex is iridium chloride complex, preferably with iridium in its oxidative states ranging from +3 to +6 states. Preferably, the iridium chloride complex is $IrCl_6^{-2}$ or $IrCl_6^{-3}$.

The invention additionally features a method of detecting a mismatch between a first nucleic acid and a second nucleic acid, wherein the method includes the following steps: (a) providing the first nucleic acid immobilized on a solid support; (b) contacting, under hybridizing conditions, the solid support and the immobilized first nucleic acid to a solution containing the sample containing the second nucleic acid and a redox pair, wherein the redox pair comprises a first transition metal complex and a second transition metal complex; and (c) measuring the electrocatalytic signal generated by hybridization of the first nucleic acid and the second nucleic acid; wherein a decrease of the signal detected in step (c) relative to that of a perfect complementarity between the first nucleic acid and the second nucleic acid, indicates that there is a mismatch between the first nucleic acid and the second nucleic acid. The method can also include an additional step of testing a control, by contacting, under hybridizing conditions, the solid support and the immobilized nucleic acid probe to a solution containing no sample, and a redox pair comprising a first transition metal complex and a second transition metal complex.

Preferably, the transition metal of the first transition metal complex is one selected from the group consisting of cobalt, iron, molybdenum, osmium, ruthenium and rhenium. More preferably, the transition metal of the first transition metal complex is ruthenium. Also preferably, the first transition metal complex is a transition metal ammonium complex. More preferably, the first transition metal ammonium complex comprises a transition metal selected from the group consisting of cobalt, iron, molybdenum, osmium, ruthenium and rhenium. Most preferably, the transition metal ammonium complex is $Ru(NH_3)_6^{3+}$.

Preferably, the transition metal of the second transition metal complex is one selected from the group consisting of cobalt, iron, molybdenum, iridium, osmium and rhenium. More preferably, the transition metal of the second transition metal complex is iron or iridium. Also preferably, the second transition metal complex is a transition metal cynate complex. More preferably, the second transition metal cynate complex comprises a transition metal selected from the group consisting of cobalt, iron, molybdenum, iridium, osmium and rhenium. Most preferably, the second transition metal cynate complex is $Fe(CN)_6^{-3}$. Also preferably, the second transition metal complex is a transition metal chloride complex. More preferably, the second transition metal chloride complex comprises a transition metal selected from the group consisting of cobalt, iron, molybdenum, iridium, osmium and rhenium. More preferably, the second transition metal complex is iridium chloride complex, preferably with iridium in its oxidative states ranging from +3 to +6 states. Preferably, the iridium chloride complex is $IrCl_6^{-2}$ or $IrCl_6^{-3}$.

The invention also features a method of detecting nucleic acid hybridization between a nucleic acid probe and a target nucleic acid, where the method includes the following steps: (a) providing a nucleic acid probe immobilized on a solid support; (b) contacting the immobilized probe to a solution containing: (i) a transition metal complex; (c) measuring the electrocatalytic signal generated; (d) contacting the immobilized probe to a solution containing: (i) a sample thought to include the target nucleic acid, and (ii) a transition metal complex; (e) measuring the electrocatalytic signal generated; wherein an increase in the signal detected in step (e) over the signal generated in step (c) indicates that hybridization between the nucleic acid probe and the target nucleic acid has occurred. Preferably, the transition metal of the transition metal complex is one selected from the group consisting of cobalt, iron, molybdenum, osmium, ruthenium and rhenium. More preferably, the transition metal of the transition metal complex is ruthenium. Also preferably, the transition metal complex is a transition metal ammonium complex. More preferably, the first transition metal ammonium complex comprises a transition metal selected from the group consisting of cobalt, iron, molybdenum, osmium, ruthenium and rhenium. Most preferably, the transition metal ammonium complex is $Ru(NH_3)_6^{3+}$.

The solutions can also include a second transition metal complex to enhance the electrocatalytic signal generated. Preferably, the transition metal of the second transition metal complex is one selected from the group consisting of cobalt, iron, molybdenum, iridium, osmium and rhenium. More preferably, the transition metal of the second transition metal complex is iron or iridium. Also preferably, the second transition metal complex is a transition metal cynate complex. More preferably, the second transition metal cynate complex comprises a transition metal selected from the group consisting of cobalt, iron, molybdenum, iridium, osmium and rhenium. Most preferably, the second transition metal cynate complex is $Fe(CN)_6^{-3}$. Also preferably, the second transition metal complex is a transition metal chloride complex. More preferably, the second transition metal chloride complex comprises a transition metal selected from the group consisting of cobalt, iron, molybdenum, iridium, osmium and rhenium. More preferably, the second transition metal complex is iridium chloride complex, preferably with iridium in its oxidative states ranging from +3 to +6 states. Preferably, the iridium chloride complex is $IrCl_6^{-2}$ or $IrCl_6^{-3}$.

Alternatively, the solutions can also include an organic molecules as a redox probe to enhance the electrocatalytic signal generated. Preferably, the organic molecule can be ascorbic acid or tripropylamine.

The method can also include rinsing steps, e.g., rinsing the electrode between contact with the different solutions.

The invention additionally features a method of detecting the presence of a target nucleic acid in a sample, wherein the method includes the following steps: (a) providing a nucleic acid probe immobilized on a solid support; (b) contacting the immobilized probe to a solution containing: (i) a transition metal complex; (c) measuring the electrocatalytic signal generated; (d) contacting the immobilized probe to a solution containing: (i) a sample thought to include the target nucleic acid, and (ii) a transition metal complex; (e) measuring the electrocatalytic signal generated; wherein an increase in the signal detected in step (e) over the signal generated in step (c) indicates the target nucleic acid is present in the sample. Preferably, the transition metal of the transition metal complex is one selected from the group consisting of cobalt, iron, molybdenum, osmium, ruthenium and rhenium. More preferably, the transition metal of the transition metal complex is ruthenium. Also preferably, the transition metal complex is a transition metal ammonium complex. More preferably, the first transition metal ammonium complex comprises a transition metal selected from the group consisting of cobalt, iron, molybdenum, osmium, ruthenium and rhenium. Most preferably, the transition metal ammonium complex is $Ru(NH_3)_6^{3+}$.

The solutions can also include a second transition metal complex to enhance the electrocatalytic signal generated. Preferably, the transition metal of the second transition metal complex is one selected from the group consisting of cobalt, iron, molybdenum, iridium, osmium and rhenium. More preferably, the transition metal of the second transition metal complex is iron or iridium. Also preferably, the second transition metal complex is a transition metal cynate complex. More preferably, the second transition metal cynate complex comprises a transition metal selected from the group consisting of cobalt, iron, molybdenum, iridium, osmium and rhenium. Most preferably, the second transition metal cynate complex is $Fe(CN)_6^{-3}$. Also preferably, the second transition metal complex is a transition metal chloride complex. More preferably, the second transition metal chloride complex comprises a transition metal selected from the group consisting of cobalt, iron, molybdenum, iridium, osmium and rhenium. More preferably, the second transition metal complex is iridium chloride complex, preferably with iridium in its oxidative states ranging from +3 to +6 states. Preferably, the iridium chloride complex is $IrCl_6^{-2}$ or $IrCl_6^{-3}$.

Alternatively, the solutions can also include an organic molecules as a redox probe to enhance the electrocatalytic signal generated. Preferably, the organic molecule can be ascorbic acid or tripropylamine.

The method can also include rinsing steps, e.g., rinsing the electrode between contact with the different solutions.

The invention further features a method of detecting a mismatch between two nucleic acids, where the method includes the following steps: (a) providing a nucleic acid probe immobilized on a solid support; (b) contacting the immobilized probe to a solution containing: (i) a transition metal complex; (c) measuring the electrocatalytic signal generated; (d) contacting the immobilized probe to a solution containing: (i) a sample thought to include the target nucleic acid, and (ii) a transition metal complex; (e) measuring the electrocatalytic signal generated; wherein a decrease in the signal detected in step (e) over the signal generated in step (c) indicates that there is a mismatch between the nucleic acid probe and the target nucleic acid. Preferably, the transition metal of the transition metal complex is one selected from the group consisting of cobalt, iron, molybdenum, osmium, ruthenium and rhenium. More preferably, the transition metal of the transition metal complex is ruthenium. Also preferably, the transition metal complex is a transition metal ammonium complex. More preferably, the first transition metal ammonium complex comprises a transition metal selected from the group consisting of cobalt, iron, molybdenum, osmium, ruthenium and rhenium. Most preferably, the transition metal ammonium complex is $Ru(NH_3)_6^{3+}$.

The solutions can also include a second transition metal complex to enhance the electrocatalytic signal generated. Preferably, the transition metal of the second transition metal complex is one selected from the group consisting of cobalt, iron, molybdenum, iridium, osmium and rhenium. More preferably, the transition metal of the second transition metal complex is iron or iridium. Also preferably, the second transition metal complex is a transition metal cynate complex. More preferably, the second transition metal cynate complex comprises a transition metal selected from the group consisting of cobalt, iron, molybdenum, iridium, osmium and rhenium. Most preferably, the second transition metal cynate complex is $Fe(CN)_6^{-3}$. Also preferably, the second transition metal complex is a transition metal chloride complex. More preferably, the second transition metal chloride complex comprises a transition metal selected from the group consisting of cobalt, iron, molybdenum, iridium, osmium and rhenium. More preferably, the second transition metal complex is iridium chloride complex, preferably with iridium in its oxidative states ranging from +3 to +6 states. Preferably, the iridium chloride complex is $IrCl_6^{-2}$ or $IrCl_6^{-3}$.

Alternatively, the solutions can also include an organic molecules as a redox probe to enhance the electrocatalytic signal generated. Preferably, the organic molecule can be ascorbic acid or tripropylamine.

The method can also include rinsing steps, e.g., rinsing the electrode between contact with the different solutions.

In any of the methods described herein, the solid support can be a gold electrode.

In any of the detection methods described herein, the redox-active probe can be an organic molecule, preferably ascorbic acid or tripropylamine, or the second transition metal complex can be substituted with an organic molecule having a substantially equivalent function as the second transition metal complex, such as ascorbic acid and tripropylamine.

Additionally, another aspect of the present invention features applying the electrocatalytic assays disclosed herein on a detection device comprising nanoelectrode ensembles for ultrasensitive detection of nucleic acids. The device comprises an array of of metallic nanoelectrode ensembles (NEEs) comprising a metallic nanowire embedded within a non-conductive substrate such as a polycarbonate membrane and a nucleic acid probe attached to the metallic nanowire. Preferably the metallic nanowire comprises gold. Preferably, the metallic nanowire ranges from about 10 to about 80 nanometers in diameter, and the nanowires have a density on the non-conductive substrate of from about $1\times10^8$ to about $1\times10^9$ per square centimeters.

In one embodiment, the array of the nanoelectrode ensembles of the present invention is two-dimensional, i.e., the nanowires on the nanoelectrodes do not protrude out of the non-conductive substrate. In another embodiment, the array of the nanoelectrode ensembles is three-dimensional, i.e., the nanowires on the nanoelectrodes protrude out of the non-conductive substrate. Preferably, the part of the nanowires that protrudes out of the non-conductive substrate is about 50 to about 300 nanometers, more preferably about 100 to about 200 nanometers.

Another embodiment includes a nucleic acid probe which is attached to the exposed metallic nanowire on the non-conductive substrate.

In another embodiment, one or plurality of the nucleic acid probe can be attached to a single metallic nanowire.

As for detecting a target nucleic acid in a sample using the electrocatalytic assays on the nanoelectrode ensembles, generally, the detection is performed with a system comprised of nanoelectrode ensembles containing the nucleic acid probes attached thereto as work electrode and a reference electrode, wherein both electrodes are connected to a signal device. Upon contacting a sample containing a target nucleic acid with the nanoelectrode ensembles, the hybridization of the nucleic acid probe with the nucleic acid from the sample occurs and results in changes in electrocatalytic currents. The changes associated with the hybridization are reflected on an amplified signal on the detecting device and thus is indicative of the presence of the target nucleic acid in the sample.

For the electrochemical detection method to work, the detection method includes contacting the array of nanoelectrode ensembles with a sample under a hybridization condition and detecting an increase in the amplified signal on the circuit that is associated with the hybridization of the nucleic acid probe on the nanoelectrode to the target nucleic acid in the sample. The increase in the signal indicates the presence of the target nucleic acid in the sample.

The detection method described herein can be used for various applications such as for detection of human genes or mutations, detection of pathogens, such as bacteria or viruses, or can be used to detect the expression of genes in a subject.

The invention also includes a kit for carrying out the method, including a nucleic acid probe immobilized on a conducting electrode, and redox reagents. The kit can include positive control samples that include target nucleic acids, and negative control samples that contain no target nucleic acid. The kit can also include specific types of positive controls, e.g., target nucleic acids that are characteristic of specific target pathogens and genes. The kit can also include packaging materials and instructions for use.

BRIEF DESCRIPTION OF THE DRAWINGS

FIG. 2A: without target. FIG. 2B: with target.

FIGS. 5A, 5B and 5C are a pair of voltammograms and a bar graph. FIG. 5A is a cyclic voltammogram illustrating enhancement of the electrocatalytic signal upon hybridization of target sequence. The initial signal is shown as a dotted trace, and the signal obtained after introduction of the target is shown as a solid line. FIG. 5B is a voltammogram obtained with the same electrodes but in the presence of Ru(III) only, which displays a very small signal increase upon introduction of the target. FIG. 5C shows detection of H. pylori-related sequences by monitoring integrated charge. Data displayed correspond to change in charge after 30 minutes of hybridization.

FIG. 8 is Ru(III)/Fe(III) electrocatalysis as a reporter of surface-immobilized DNA. (A) Dependence of electrocatalysis on DNA surface coverage. DNA films with varying densities were prepared by varying $MgCl_2$ concentration during exposure of gold substrates to probe solutions. Cyclic voltammograms obtained at electrodes modified in the presence of 10 (dotted line), 30 (dashed line), and 100 (solid line) mM $MgCl_2$ are shown. (B) Cyclic voltammograms illustrating enhancement of electrocatalytic signal upon hybridization of T2a (dotted line corresponds to CV obtained pre-hybridization, solid line corresponds to CV obtained after hybridization). DNA films were prepared in the presence of 50 mM $MgCl_2$. Hybridization with T2a was induced by introducing a solution containing 20 µM DNA, 25 mM sodium phosphate (pH 7), 25 mM NaCl, and 100 mM $MgCl_2$ for 30 minutes. The solution of target was heated to 40° C., deposited on an inverted electrode, and incubated for 30 minutes. No change in signal was obtained when buffer or a noncomplementary sequence (T-NC) was introduced. For comparison, voltammograms of a solution of 27 µM $Ru(NH_3)_6^{3+}$ obtained before (dotted line) and after hybridization (solid line) are shown.

FIG. 13A shows schematic illustrations of 2D and 3D nanoelectrode ensembles.

DETAILED DESCRIPTION

Figure 1:
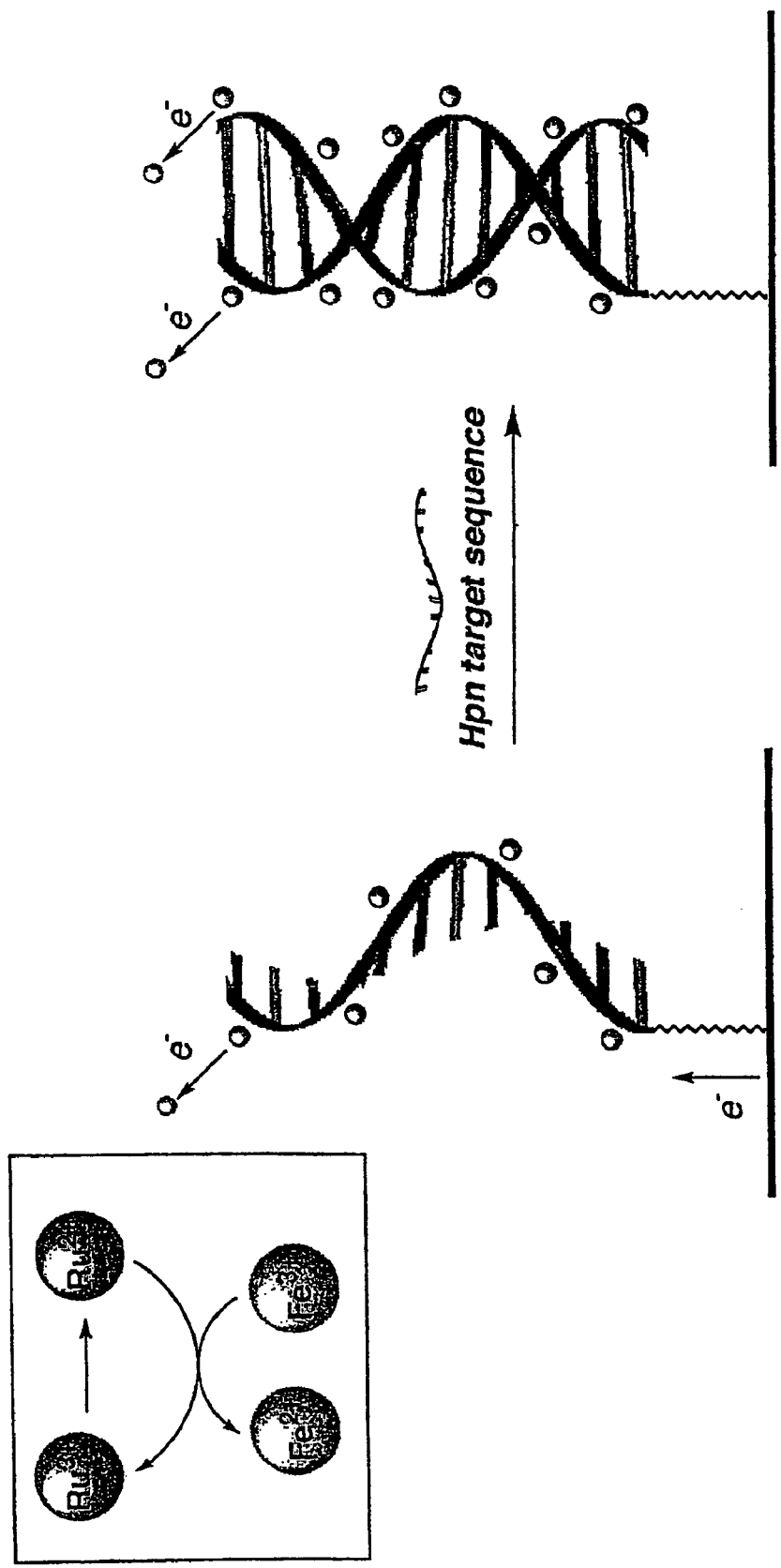
FIG. 1 is an illustration of electrocatalytic detection of DNA hybridization of an H. pylori sequence.

Definitions:

"Solid support", as used herein, refers to the material to which the nucleic acid probe is attached. Suitable solid supports are available commercially, and will be apparent to the skilled person. The supports can be manufactured from materials such as glass, ceramics, silica and silicon, and can incorporate conductive material to serve as an electrode. Conductive supports with a gold surface may also be used. The supports usually comprise a flat (planar) surface, or at least a structure in which the polynucleotides to be interrogated are in approximately the same plane. The support can be an electrode, or can be attached to an electrode.

"Mismatch", as used herein, refers to a duplex in which less than all of the nucleotides on one strand are perfectly matched to the other strand (e.g., where nucleotide pairing other than adenosine-thymine or guanine-cytosine occurs, e.g., nucleotide paring such as adenosine-cytosine, adenosine-guanine, adenosine-adenosine, thymine-cytosine, thymine-guanine, thymine-thymine, guanine-guanine, or cytosine-cytosine occurs), where a deletion or insertion of one or more DNA nucleotides on one strand as compared to the other complementary strand occurs (e.g., a deletion of 1, 2, 5, 10, 15, or more nucleotides or an insertion of 1, 2, 5, 10, 15, or more nucleotides occurs), or other mismatches between the two strand of the duplex occurs. DNA mismatches may arise from nucleic acid replication errors, mutagenesis, deamination of 5-methylcytosine, formation of thymidine dimers, nucleic acid recombination, etc.

By "probe" is meant a single-stranded oligonucleotide capable of binding to at least a portion of the target nucleic acid sought to be detected. The probe will generally have a sequence partly or completely complementary to a target nucleic acid sequence sought to be detected, so as to stably hybridize thereto under stringent hybridization conditions. In the case of a group or species-specific probe, the probe has the ability to stably hybridize to a target nucleic acid and not to non-target nucleic acids such as those from organisms outside the phylogenetic group or species under stringent hybridization conditions. Probes may, but need not, have regions which are not complementary to a target sequence, as long as such sequences do not substantially alter the probe's desired specificity under stringent hybridization conditions.

As used herein, the term "a nucleic acid probe" also refers to a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified on bases (7-deazaguanosine, inosine, etc.) or on sugar moiety. In addition, the bases in a probe can be joined by a linkage other than a phosphodiester bond, so long as it does not interfere with hybridization. Thus, for example, probes can be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. By assaying for the presence or absence of the probe, one can detect the presence or absence of the select sequence or subsequence.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. ESTs, chromosomes, cDNAs, mRNAs, and rRNAs are representative examples of molecules that can be referred to as nucleic acids.

As used herein, the term "hybridization" refers to any process by which a strand of nucleic acid binds with a complementary strand through base pairing.

As used herein, the term "hybridization conditions" refer to standard conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety. Non-limiting examples of hybridization conditions include low stringency hybridization conditions, moderate stringency hybridization conditions and high stringency hybridization conditions.

As used herein, the term "sample" as used in its broadest sense, refers to any plant, animal or viral material containing DNA or RNA, such as, for example, tissue or fluid isolated from an individual (including without limitation plasma, serum, cerebrospinal fluid, lymph, tears, saliva and tissue sections) or from in vitro cell culture constituents, as well as samples from the environment. The sample of nucleic acids can be drawn from any source and can be natural or synthetic. The sample of nucleic acids may contain of deoxyribonucleic acids (DNA), ribonucleic acids (RNA), or copolymers of deoxyribonucleic acids and ribonucleic acids or combinations thereof. Alternatively, the sample may have been subject to purification (e.g. extraction) or other treatment. The term "sample" can also refer to "a biological sample."

As used herein, the term "a biological sample" refers to a whole organism or a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). "A biological sample" further refers to a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. Most often, the sample has been removed from an animal, but the term "biological sample" can also refer to cells or tissue analyzed in vivo, i.e., without removal from animal. Typically, a "biological sample" will contain cells from the animal, but the term can also refer to non-cellular biological material, such as non-cellular fractions of blood, saliva, or urine, that can be used to measure the cancer-associated polynucleotide or polypeptides levels. "A biological sample" further refers to a medium, such as a nutrient broth or gel in which an organism has been propagated, which contains cellular components, such as proteins or nucleic acid molecules.

As used herein, the term "an increase of the signal" means that the signal generated from hybridization between two nucleic acids is greater than that generated from either one of said two nucleic acids alone in unhybridized form. Preferably, the hybridization is between a nucleic acid probe and a target nucleic acid. Also preferably, the hybridization is between a first nucleic acid and a second nucleic acid. Preferably, the increase is at least about 10%, preferably at least about 15%, about 25%, about 30%, about 40%, about 50%, about 65%, about 75%, about 85%, about 90%, about 95%, about more than 100%, about twofold, about ten fold, about fifty fold, or greater.

As used herein, the term "decrease of the signal" means that the signal generated from hybridization between two nucleic acids that are complementary but for a mismatch, is lower than that generated from hybridization between two completely complementary nucleic acids. Preferably, the decrease is at least about 10%, preferably at least about 15%, about 25%, about 30%, about 40%, about 50%, about 65%, about 75%, about 85%, about 90%, about 95%, about more than 100%, about twofold, about ten fold, about fifty fold, or greater.

As used herein, the term "a transition metal" refers to any of the elements found between the Group IIA Elements and the Group IIB Elements in the periodic table. Transition metals to be used in a transition metal complex of the present invention include those of the fourth, fifth, and sixth periods of the periodic table of elements. Preferably, the transition metals used in the present invention include iron, ruthenium, cobalt, molybdenum, osmium and rhenium.

As used herein, the term "transition metal complex" refers to a structure composed of a central transition metal atom or ion, generally a cation, surrounded by a number of negatively charged or neutral ligands possessing lone pairs electrons that can be given to the central metal.

The transition metal is defined herein above. The ligands bind to the central transition metal using dative bonds. There are a number of different types of ligands that can be applied to the present invention. Non-limiting examples include but not limited to, monodentate ligands, bidendate ligands, tridendate ligands, tetradentate ligands and hexadentaate ligands, etc. Preferably, the ligands can be pyridine-based, phenathroline-based, heterocyclic, aquo, aromatic, chloride ($Cl^-$), or ammonia ($NH_3$), or cyanide ($CN^-$).

As used herein, the singular forms "a," "an," and "the" used in the specification and claims include both singular and plural referents unless the content clearly dictates otherwise.

I Electrocatalytic Detection Assay for Detecting Nucleic Acid Hybridization

Described herein is an electrocatalytic detection assay that reports hybridization between nucleic acids, or between nucleic acids and proteins. In one aspect, the assay can be used to detect hybridization between a nucleic acid probe and a DNA or RNA target. The present assay is sufficiently sensitive to resolve single-base changes in the target sequence. The method exploits a reaction between a redox pair comprising a nucleic acid-binding compound and a redox-active probe.

The nucleic acid-binding compound can be a transition metal complex. Preferably, the transition metal is one selected from the group consisting of cobalt, iron, molybdenum, osmium, ruthenium and rhenium. Also preferably, the transition metal complex is an ammonium complex of the transition metal. More preferably, the transition metal complex is $Ru(NH_3)_6^{3+}$.

The redox active probe can also be a transition metal complex. Preferably, the transition metal is one selected from the group consisting of cobalt, molybdenum, iridium, osmium, iron and rhenium. Also preferably, the transition metal complex is a cynate or choloride complex of the transition metal. More preferably, the transition metal complex is $Fe(CN)_6^{-3}$. More preferably, the second transition metal complex is iridium chloride complex, preferably with iridium in its oxidative states ranging from +3 to +6 states. Preferably, the iridium chloride complex is $IrCl_6^{-2}$ or $IrCl_6^{-3}$.

Alternatively, the redox active probe can also be an organic molecule such as ascorbic acid or tripropylamine.

The nucleic acid-binding compound binds to the nucleic acid primarily through electrostatic interactions with the phosphate backbone, and therefore its electrochemical reduction yields a signal that reports on the increase of negatively charged groups at the electrode surface upon hybridization of a target nucleic acid. The signal is amplified by the transition metal or organic oxidant of the redox active probe which permits the transition metal to be regenerated for multiple cycles. The immobilization of the nucleic acid probe on highly conductive surfaces, e.g., gold, amplifies the kinetic effects of base mismatches on nucleic acid hybridization, permitting single-base changes to be resolved.

One advantage of the assay is the use of the nucleic acid-bound compound to report the hybridization event and the coupling of this signal to another electrocatalytic process. The design also provides superior sensitivity, e.g., detection of a single base mismatch.

The invention described herein is useful for the detection of infectious bacterial and viral agents. The invention is also useful in detecting genes and proteins, e.g., changes in genes and proteins, e.g., changes in oncogenes. It therefore is useful in a clinical diagnostic setting, and for detection of pathogenic agents in non-clinical settings, e.g., detection of biot-error agents.

In another aspect, the method described herein can be used to determine the presence of a target nucleic acid according to the following protocol. A biological sample suspected of containing the target nucleic acid may optionally be treated to release any nucleic acid contained within the sample. For instance, the sample can be serum, blood, other bodily fluids, tissue, etc. The sample can also be from a human, an animal, a plant, etc. The sample can also be nucleic acid washed from a swab or some other type of material used to wipe surfaces to detect contaminants. The sample can also be nucleic acid extracted or washed off of a filter through which air is passed, e.g. a filter from an air filtration system, in the case of detecting airborne bioterror agents. Such an article can be treated to extract the nucleic acid by methods that are known in the art, e.g., forensics and contamination detection. The nucleic acid extracted from the article can be tested directly by the methods described herein, or can be amplified to enhance detection.

In one embodiment, the invention features a method of detecting nucleic acid hybridization between a nucleic acid probe and a target nucleic acid in a sample, where the method includes the steps of: (a) providing a nucleic acid probe immobilized on a solid substrate; (b) contacting, under hybridizing conditions, the solid support and the immobilized probe to a solution containing the sample and a redox pair, wherein the redox pair comprises a first transition metal complex and a second transition metal complex; and (c) measuring the electrocatalytic signal generated by hybridization of the nucleic acid probe and the target nucleic acid; where an increase of the signal detected in step (c) relative to that of a control sample containing no nucleic acid, indicates that the nucleic acid hybridization has occurred. The method can also include an additional step of testing a control, by contacting, under hybridizing conditions, the solid support and the immobilized nucleic acid probe to a solution containing no sample, and a redox pair comprising a first transition metal complex and a second transition metal complex.

Preferably, the transition metal of the first transition metal complex is one selected from the group consisting of cobalt, iron, molybdenum, osmium, ruthenium and rhenium. More preferably, the transition metal of the first transition metal complex is ruthenium. Also preferably, the first transition metal complex is a transition metal ammonium complex. More preferably, the first transition metal ammonium complex comprises a transition metal selected from the group consisting of cobalt, iron, molybdenum, osmium, ruthenium and rhenium. Most preferably, the transition metal ammonium complex is $Ru(NH_3)_6^{3+}$.

Preferably, the transition metal of the second transition metal complex is one selected from the group consisting of cobalt, iron, molybdenum, iridium, osmium and rhenium. More preferably, the transition metal of the second transition metal complex is iron or iridium. Also preferably, the second transition metal complex is a transition metal cynate complex. More preferably, the second transition metal cynate complex comprises a transition metal selected from the group consisting of cobalt, iron, molybdenum, iridium, osmium and rhenium. Most preferably, the second transition metal cynate complex is $Fe(CN)_6^{-3}$. Also preferably, the second transition metal complex is a transition metal chloride complex. More preferably, the second transition metal chloride complex comprises a transition metal selected from the group consisting of cobalt, iron, molybdenum, iridium, osmium and rhenium. More preferably, the second transition metal complex is iridium chloride complex, preferably with iridium in its oxidative states ranging from +3 to +6 states. Preferably, the iridium chloride complex is $IrCl_6^{-2}$ or $IrCl_6^{-3}$.

In another embodiment, the invention also features a method of detecting nucleic acid hybridization between a first nucleic acid and a second nucleic acid, wherein the method includes the steps of: (a) providing the first nucleic acid immobilized on a solid support; (b) contacting, under hybridizing conditions, the solid support and the immobilized first nucleic acid to a solution suspected of containing the second nucleic acid and a redox pair comprising a first transition metal complex and a second transition metal complex; and (c) measuring the electrocatalytic signal generated by hybridization of the first and second nucleic acids; wherein an increase of the signal detected in step (c) relative to that of an unhybridized first nucleic acid, indicates that nucleic acid hybridization has occurred. The method can also include an additional step of testing a control, by contacting, under hybridizing conditions, the solid support and the immobilized first nucleic acid to a solution containing no sample, and a redox pair comprising a first transition metal complex and a second transition metal complex.

Preferably, the transition metal of the first transition metal complex is one selected from the group consisting of cobalt, iron, molybdenum, osmium, ruthenium and rhenium. More preferably, the transition metal of the first transition metal complex is ruthenium. Also preferably, the first transition metal complex is a transition metal ammonium complex. More preferably, the first transition metal ammonium complex comprises a transition metal selected from the group consisting of cobalt, iron, molybdenum, osmium, ruthenium and rhenium. Most preferably, the transition metal ammonium complex is $Ru(NH_3)_6^{3+}$.

Preferably, the transition metal of the second transition metal complex is one selected from the group consisting of cobalt, iron, molybdenum, iridium, osmium and rhenium. More preferably, the transition metal of the second transition metal complex is iron or iridium. Also preferably, the second transition metal complex is a transition metal cynate complex. More preferably, the second transition metal cynate complex comprises a transition metal selected from the group consisting of cobalt, iron, molybdenum, iridium, osmium and rhenium. Most preferably, the second transition metal cynate complex is $Fe(CN)_6^{-3}$. Also preferably, the second transition metal complex is a transition metal chloride complex. More preferably, the second transition metal chloride complex comprises a transition metal selected from the group consisting of cobalt, iron, molybdenum, iridium, osmium and rhenium. More preferably, the second transition metal complex is iridium chloride complex, preferably with iridium in its oxidative states ranging from +3 to +6 states. Preferably, the iridium chloride complex is $IrCl_6^{-2}$ or $IrCl_6^{-3}$.

In another aspect, the invention features a method of detecting a mismatch between a first nucleic acid and a second nucleic acid, comprising: (a) providing a nucleic acid probe immobilized on a solid support; (b) contacting, under hybridizing conditions, the solid support and the immobilized probe to a solution containing the sample containing a target nucleic acid and a redox pair, wherein the redox pair comprises a first transition metal complex and a second transition metal complex; and (c) measuring the electrocatalytic signal generated by hybridization of the nucleic acid probe and the target nucleic acid; wherein a decrease of the signal detected in step (c) relative to that of a perfect complementarity between the nucleic acid probe and the target nucleic acid, indicates that there is a mismatch between the first nucleic acid and the second nucleic acid. The method can also include an additional step of testing a control, by contacting, under hybridizing conditions, the solid support and the immobilized nucleic acid probe to a solution containing no sample, and a redox pair comprising a first transition metal complex and a second transition metal complex.

Preferably, the transition metal of the first transition metal complex is one selected from the group consisting of cobalt, iron, molybdenum, osmium, ruthenium and rhenium. More preferably, the transition metal of the first transition metal complex is ruthenium. Also preferably, the first transition metal complex is a transition metal ammonium complex. More preferably, the first transition metal ammonium complex comprises a transition metal selected from the group consisting of cobalt, iron, molybdenum, osmium, ruthenium and rhenium. Most preferably, the transition metal ammonium complex is $Ru(NH_3)_6^{3+}$.

Preferably, the transition metal of the second transition metal complex is one selected from the group consisting of cobalt, iron, molybdenum, iridium, osmium and rhenium. More preferably, the transition metal of the second transition metal complex is iron or iridium. Also preferably, the second transition metal complex is a transition metal cynate complex. More preferably, the second transition metal cynate complex comprises a transition metal selected from the group consisting of cobalt, iron, molybdenum, iridium, osmium and rhenium. Most preferably, the second transition metal cynate complex is $Fe(CN)_6^{-3}$. Also preferably, the second transition metal complex is a transition metal chloride complex. More preferably, the second transition metal chloride complex comprises a transition metal selected from the group consisting of cobalt, iron, molybdenum, iridium, osmium and rhenium. More preferably, the second transition metal complex is iridium chloride complex, preferably with iridium in its oxidative states ranging from +3 to +6 states. Preferably, the iridium chloride complex is $IrCl_6^{-2}$ or $IrCl_6^{-3}$.

The invention additionally features a method of detecting a mismatch between a first nucleic acid and a second nucleic acid, wherein the method includes the following steps: (a) providing the first nucleic acid immobilized on a solid support; (b) contacting, under hybridizing conditions, the solid support and the immobilized first nucleic acid to a solution containing the sample containing the second nucleic acid and a redox pair, wherein the redox pair comprises a first transition metal complex and a second transition metal complex; and (c) measuring the electrocatalytic signal generated by hybridization of the first nucleic acid and the second nucleic acid; wherein a decrease of the signal detected in step (c) relative to that of a perfect complementarity between the first nucleic acid and the second nucleic acid, indicates that there is a mismatch between the first nucleic acid and the second nucleic acid. The method can also include an additional step of testing a control, by contacting, under hybridizing conditions, the solid support and the immobilized nucleic acid probe to a solution containing no sample, and a redox pair comprising a first transition metal complex and a second transition metal complex.

Preferably, the transition metal of the first transition metal complex is one selected from the group consisting of cobalt, iron, molybdenum, osmium, ruthenium and rhenium. More preferably, the transition metal of the first transition metal complex is ruthenium. Also preferably, the first transition metal complex is a transition metal ammonium complex. More preferably, the first transition metal ammonium complex comprises a transition metal selected from the group consisting of cobalt, iron, molybdenum, osmium, ruthenium and rhenium. Most preferably, the transition metal ammonium complex is $Ru(NH_3)_6^{3+}$.

Preferably, the transition metal of the second transition metal complex is one selected from the group consisting of cobalt, iron, molybdenum, iridium, osmium and rhenium. More preferably, the transition metal of the second transition metal complex is iron or iridium. Also preferably, the second transition metal complex is a transition metal cynate complex. More preferably, the second transition metal cynate complex comprises a transition metal selected from the group consisting of cobalt, iron, molybdenum, iridium, osmium and rhenium. Most preferably, the second transition metal cynate complex is $Fe(CN)_6^{-3}$. Also preferably, the second transition metal complex is a transition metal chloride complex. More preferably, the second transition metal chloride complex comprises a transition metal selected from the group consisting of cobalt, iron, molybdenum, iridium, osmium and rhenium. More preferably, the second transition metal complex is iridium chloride complex, preferably with iridium in its oxidative states ranging from +3 to +6 states. Preferably, the iridium chloride complex is $IrCl_6^{-2}$ or $IrCl_6^{-3}$.

In another embodiment, the invention also features a method of detecting nucleic acid hybridization between a nucleic acid probe and a target nucleic acid, where the method includes the following steps: (a) providing a nucleic acid probe immobilized on a solid support; (b) contacting the immobilized probe to a solution containing: (i) a transition metal complex; (c) measuring the electrocatalytic signal generated; (d) contacting the immobilized probe to a solution containing: (i) a sample thought to include the target nucleic acid, and (ii) a transition metal complex; (e) measuring the electrocatalytic signal generated; wherein an increase in the signal detected in step (e) over the signal generated in step (c) indicates that hybridization between the nucleic acid probe and the target nucleic acid has occurred. Preferably, the transition metal of the transition metal complex is one selected from the group consisting of cobalt, iron, molybdenum, osmium, ruthenium and rhenium. More preferably, the transition metal of the transition metal complex is ruthenium. Also preferably, the transition metal complex is a transition metal ammonium complex. More preferably, the first transition metal ammonium complex comprises a transition metal selected from the group consisting of cobalt, iron, molybdenum, osmium, ruthenium and rhenium. Most preferably, the transition metal ammonium complex is $Ru(NH_3)_6^{3+}$.

The solutions can also include a second transition metal complex to enhance the electrocatalytic signal generated. Preferably, the transition metal of the second transition metal complex is one selected from the group consisting of cobalt, iron, molybdenum, iridium, osmium and rhenium. More preferably, the transition metal of the second transition metal complex is iron or iridium. Also preferably, the second transition metal complex is a transition metal cynate complex. More preferably, the second transition metal cynate complex comprises a transition metal selected from the group consisting of cobalt, iron, molybdenum, iridium, osmium and rhenium. Most preferably, the second transition metal cynate complex is $Fe(CN)_6^{-3}$. Also preferably, the second transition metal complex is a transition metal chloride complex. More preferably, the second transition metal chloride complex comprises a transition metal selected from the group consisting of cobalt, iron, molybdenum, iridium, osmium and rhenium. More preferably, the second transition metal complex is iridium chloride complex, preferably with iridium in its oxidative states ranging from +3 to +6 states. Preferably, the iridium chloride complex is $IrCl_6^{-2}$ or $IrCl_6^{-3}$.

Alternatively, the solutions can also include an organic molecules as a redox probe to enhance the electrocatalytic signal generated. Preferably, the organic molecule can be ascorbic acid or tripropylamine.

The method can also include rinsing steps, e.g., rinsing the electrode between contact with the different solutions.

Another aspect of the invention additionally features a method of detecting the presence of a target nucleic acid in a sample, wherein the method includes the following steps: (a) providing a nucleic acid probe immobilized on a solid support; (b) contacting the immobilized probe to a solution containing: (i) a transition metal complex; (c) measuring the electrocatalytic signal generated; (d) contacting the immobilized probe to a solution containing: (i) a sample thought to include the target nucleic acid, and (ii) a transition metal complex; (e) measuring the electrocatalytic signal generated; wherein an increase in the signal detected in step (e) over the signal generated in step (c) indicates the target nucleic acid is present in the sample. Preferably, the transition metal of the transition metal complex is one selected from the group consisting of cobalt, iron, molybdenum, osmium, ruthenium and rhenium. More preferably, the transition metal of the transition metal complex is ruthenium. Also preferably, the transition metal complex is a transition metal ammonium complex. More preferably, the first transition metal ammonium complex comprises a transition metal selected from the group consisting of cobalt, iron, molybdenum, osmium, ruthenium and rhenium. Most preferably, the transition metal ammonium complex is $Ru(NH_3)_6^{-3}$.

The solutions can also include a second transition metal complex to enhance the electrocatalytic signal generated. Preferably, the transition metal of the second transition metal complex is one selected from the group consisting of cobalt, iron, molybdenum, iridium, osmium and rhenium. More preferably, the transition metal of the second transition metal complex is iron or iridium. Also preferably, the second transition metal complex is a transition metal cynate complex. More preferably, the second transition metal cynate complex comprises a transition metal selected from the group consisting of cobalt, iron, molybdenum, iridium, osmium and rhenium. Most preferably, the second transition metal cynate complex is $Fe(CN)_6^{-3}$. Also preferably, the second transition metal complex is a transition metal chloride complex. More preferably, the second transition metal chloride complex comprises a transition metal selected from the group consisting of cobalt, iron, molybdenum, iridium, osmium and rhenium. More preferably, the second transition metal complex is iridium chloride complex, preferably with iridium in its oxidative states ranging from +3 to +6 states. Preferably, the iridium chloride complex is $IrCl_6^{-2}$ or $IrCl_6^{-3}$.

Alternatively, the solutions can also include an organic molecules as a redox probe to enhance the electrocatalytic signal generated. Preferably, the organic molecule can be ascorbic acid or tripropylamine.

The method can also include rinsing steps, e.g., rinsing the electrode between contact with the different solutions.

The invention further features a method of detecting a mismatch between two nucleic acids, where the method includes the following steps: (a) providing a nucleic acid probe immobilized on a solid support; (b) contacting the immobilized probe to a solution containing: (i) a transition metal complex; (c) measuring the electrocatalytic signal generated; (d) contacting the immobilized probe to a solution containing: (i) a sample thought to include the target nucleic acid, and (ii) a transition metal complex; (e) measuring the electrocatalytic signal generated; wherein a decrease in the signal detected in step (e) over the signal generated in step (c) indicates that there is a mismatch between the nucleic acid probe and the target nucleic acid. Preferably, the transition metal of the transition metal complex is one selected from the group consisting of cobalt, iron, molybdenum, osmium, ruthenium and rhenium. More preferably, the transition metal of the transition metal complex is ruthenium. Also preferably, the transition metal complex is a transition metal ammonium complex. More preferably, the first transition metal ammonium complex comprises a transition metal selected from the group consisting of cobalt, iron, molybdenum, osmium, ruthenium and rhenium. Most preferably, the transition metal ammonium complex is $Ru(NH_3)_6^{3+}$.

The solutions can also include a second transition metal complex to enhance the electrocatalytic signal generated. Preferably, the transition metal of the second transition metal complex is one selected from the group consisting of cobalt, iron, molybdenum, iridium, osmium and rhenium. More preferably, the transition metal of the second transition metal complex is iron or iridium. Also preferably, the second transition metal complex is a transition metal cynate complex. More preferably, the second transition metal cynate complex comprises a transition metal selected from the group consisting of cobalt, iron, molybdenum, iridium, osmium and rhenium. Most preferably, the second transition metal cynate complex is $Fe(CN)_6^{-3}$. Also preferably, the second transition metal complex is a transition metal chloride complex. More preferably, the second transition metal chloride complex comprises a transition metal selected from the group consisting of cobalt, iron, molybdenum, iridium, osmium and rhenium. More preferably, the second transition metal complex is iridium chloride complex, preferably with iridium in its oxidative states ranging from +3 to +6 states. Preferably, the iridium chloride complex is $IrCl_6^{-2}$ or $IrCl_6^{-3}$.

Alternatively, the solutions can also include an organic molecules as a redox probe to enhance the electrocatalytic signal generated. Preferably, the organic molecule can be ascorbic acid or tripropylamine.

The method can also include rinsing steps, e.g., rinsing the electrode between contact with the different solutions.

In any of the detection methods described herein, the solid support can be a gold electrode.

In any of the detection methods described herein, the redox-active probe can be an organic molecule, preferably ascorbic acid or tripropylamine, or the second transition metal complex can be substituted with an organic molecule having a substantially equivalent function as the second transition metal complex, such as ascorbic acid and tripropylamine.

The target nucleic acid that is detected by the method of the present invention can be, for example, single-stranded or double-stranded DNA, single-stranded or double-stranded RNA, single-stranded or double-stranded protein nucleic acid (PNA) or a hybrid of DNA, RNA and/or PNA. The target also can be a polynucleotide, e.g., in a purified or non-purified form. The sample of nucleic acids can be drawn from any source and can be natural or synthetic. The sample of nucleic acid may contain of deoxyribonucleic acids (DNA), ribonucleic acids (RNA), or copolymers of deoxyribonucleic acid and ribonucleic acid or combinations thereof. The target polynucleotide can be synthesized enzymatically or chemically in vitro, or be synthesized non-enzymatically. The sample containing the target polynucleotide can also comprise extragenomic DNA from an organism, RNA transcripts thereof, or cDNA prepared from RNA transcripts thereof. Also, the target polynucleotide can be synthesized by the polymerase or ligase chain reaction.

Preferably, the nucleic acid probe is a sequence that is known to be unique to the target nucleic acid (e.g., pathogen) being detected. Such unique sequences are known for a number of pathogens, and methods for obtaining such unique sequences are also known (see, e.g., U.S. Pat. No. 4,900,659, "Nucleotide sequence composition and method for detection of *Neisseria gonorrhoeae* and method for screening for a nucleotide sequence that is specific for a genetically distinct group"). The probe sequence is capable of binding to the target nucleic acid of complementary sequence through one or more types of chemical bonds including base pairing.

Among the target nucleic acid which can be detected using the molecular probe of the invention is genetic material in the form of DNA or RNA obtained from any naturally occurring prokaryotes such as for example, pathogenic or non-pathogenic bacteria including but not limited to species of *Escherichia, Salmonella, Clostridium, Chlamydia*, etc., eukaryotes such as for example, protozoans and parasites, fungi, yeast, higher plants, insects, lower and higher animals, including mammals and humans and cells in tissue culture, or viruses such as for example, Herpes viruses, HIV, influenza virus, Epstein-Barr virus, hepatitis B virus, etc.

Target nucleic acids from these sources may, for example, be found in samples of a bodily fluid from an animal, including a human, such as, but not limited to, blood, urine, lymphatic fluid, synovial fluid, bile, phlegm, saliva, menstrual fluid and semen. In addition, samples containing DNA or RNA may, for example, be found in fluids from a plant, such as, but not limited to, xylem fluid, phloem fluid and plant exudates. Samples containing DNA or RNA may, for example also be found in non-living sources such as, but not limited to, food, sewage, forensic samples, lakes, reservoirs, rivers and oceans. Target polynucleotides can also be those of defunct or extinct organisms, e.g., pressed plants in herbarium collections, or from pelts, taxidermy displays, fossils, or those of biological materials in museum collections.

The target nucleic acid molecule may optionally be amplified prior to detection by the method of the present invention. The target nucleic acid can be in either a double-stranded or single-stranded form. In the case where the target nucleic acid molecule is double-stranded, it is preferably first treated by a denaturation agent to render the two strands into a single-stranded, or partially single-stranded form, at the start of the amplification reaction, by methods known in the art such as heating, alkali treatment, or by enzymatic methods. General methods for accomplishing this treatment are provided by Sambrook, J. et al., *Molecular Cloning: A Laboratory Manual*, Cold Spring Harbor Laboratory Press, Cold Spring Harbor, N.Y., U.S.A. (1989).

Once the sample has been treated to expose any target nucleic acid, the solution can be tested as described herein to detect hybridization between the attached nucleic acid and the target nucleic acid, if such is present. Alternatively, some samples can be tested directly, e.g., the target may exist in a serum sample and can be directly accessible, and may not require treatment to release the nucleic acid.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., *Molecular Cloning: A Laboratory Manual*, Cold Spring Harbor Laboratory Press). The conditions of temperature and ionic strength determine the "stringency" of the hybridization. For preliminary screening for homologous nucleic acids, low stringency hybridization conditions, corresponding to a $T_m$ of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementary, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8). Preferably a minimum length for a hybridizable nucleic acid is at least about 10 nucleotides; preferably at least about 15 nucleotides; and more preferably the length is at least about 20 nucleotides; and most preferably 30 nucleotides.

"High stringency hybridization conditions" can employ hybridization at either (1) 1×SSC (10×SSC=3 M NaCl, 0.3 M Na$_3$-citrate·2H$_2$O (88 g/liter), pH to 7.0 with 1 M HCl), 1% SDS (sodium dodecyl sulfate), 0.1-2 mg/ml denatured salmon sperm DNA at 65° C., (2) 1×SSC, 50% formamide, 1% SDS, 0.1-2 mg/ml denatured salmon sperm DNA at 42° C., (3) 1% bovine serum albumen (fraction V), 1 mM Na$_2$.EDTA, 0.5 M NaHPO$_4$ (pH 7.2) (1 M NaHPO$_4$=134 g Na$_2$HPO$_4$.7H$_2$O, 4 ml 85% H$_3$PO$_4$ per liter), 7% SDS, 0.1-2 mg/ml denature DNA at 65° C., (4) 50% formamide, 5×SSC, 0.02 M Tris-HCl (pH 7.6), 1× Denhardt's solution (100×=10 g Ficoll 400, 10 g polyvinylpyrrolidone, 10 g bovine serum albumin (fraction V), water to 500 ml), 10% dextran sulfate, 1% SDS, 0.1-2 mg/ml denatured salmon sperm DNA at 42° C., (5) 5×SSC, 5× Denhardt's solution, 1% SDS, 100 µg/ml denatured salmon sperm DNA at 65° C., or (6) 5×SSC, 5× Denhardt's solution, 50% formamide, 1% SDS, 100 µg/ml denatured salmon sperm DNA at 42° C., with high stringency washes of either (1) 0.3-0.1×SSC, 0.1% SDS at 65° C., or (2) 1 mM Na$_2$EDTA, 40 mM NaHPO$_4$ (pH 7.2), 1% SDS at 65° C. The a conditions are intended to be used for DNA-DNA hybrids of 50 base pairs or longer. Where the hybrid is believed to be less than 18 base pairs in length, the hybridization and wash temperatures should be 5-10° C. below that of the calclated $T_m$ of the hybrid, where $T_m$ in ° C.=(2× the number of A and T bases)+(4× the number of G and C bases). For hybrids believed to be about 18 to about 49 base pairs in length, the $T_m$ in ° C.=(81.5° C.+16.6 (log$_{10}$M)+0.41(% G+C)–0.61 (% formamide)–500/L), where "M" is the molarity of monovalent cations (e.g., Na$^+$), and "L" is the length of the hybrid in base pairs.

"Moderate stringency hybridization conditions" can employ hybridization at either (1) 4×SSC, (10×SSC=3 M NaCl, 0.3 M Na$_3$-citrate-2H$_2$O (88 g/liter), pH to 7.0 with 1 M HCl), 1% SDS (sodium dodecyl sulfate), 0.1-2 mg/ml denatured salmon sperm DNA at 65° C., (2) 4×SSC, 50% formamide, 1% SDS, 0.1-2 mg/ml denatured salmon sperm DNA at 42° C., (3) 1% bovine serum albumen (fraction V), 1 mM Na$_2$·EDTA, 0.5 M NaHPO$_4$ (pH 7.2) (1 M NaHPO$_4$=134 g Na$_2$HPO$_4$.7H$_2$O, 4 ml 85% H$_3$PO$_4$ per liter), 7% SDS, 0.1-2 mg/ml denature DNA at 65° C., (4) 50% formamide, 5×SSC, 0.02 M Tris-HCl (pH 7.6), 1× Denhardt's solution (100×=10 g Ficoll 400, 10 g polyvinylpyrrolidone, 10 g bovine serum albumin (fraction V), water to 500 ml), 10% dextran sulfate, 1% SDS, 0.1-2 mg/ml denatured salmon sperm DNA at 42° C., (5) 5×SSC, 5× Denhardt's solution, 1% SDS, 100 µg/ml denatured salmon sperm DNA at 65° C., or (6) 5×SSC, 5× Denhardt's solution, 50% formamide, 1% SDS, 100 µg/ml denatured salmon sperm DNA at 42° C., with moderate stringency washes of 1×SSC, 0.1% SDS at 65° C. The above conditions are intended to be used for DNA-DNA hybrids of 50 base pairs or longer. Where the hybrid is believed to be less than 18 base pairs in length, the hybridization and wash temperatures should be 5-10° C. below that of the calclated $T_m$ of the hybrid, where $T_m$ in ° C.=(2× the number of A and T bases)+(4× the number of G and C bases). For hybrids believed to be about 18 to about 49 base pairs in length, the $T_m$ in ° C.=(81.5° C.+16.6 (log$_{10}$M)+0.41 (% G+C)–0.61 (% formamide)–500/L), where "M" is the molarity of monovalent cations (e.g., Na$^+$), and "L" is the length of the hybrid in base pairs.

"Low stringency hybridization conditions" can employ hybridization at either (1) 4×SSC, (10×SSC=3 M NaCl, 0.3 M Na$_3$-citrate·2H$_2$O (88 g/liter), pH to 7.0 with 1 M HCl), 1% SDS (sodium dodecyl sulfate), 0.1-2 mg/ml denatured salmon sperm DNA at 50° C., (2) 6×SSC, 50% formamide, 1% SDS, 0.1-2 mg/ml denatured salmon sperm DNA at 40° C., (3) 1% bovine serum albumen (fraction V), 1 mM Na$_2$·EDTA, 0.5 M NaHPO$_4$ (pH 7.2) (1 M NaHPO$_4$=134 g Na$_2$HPO$_4$.7H$_2$O, 4 ml 85% H$_3$PO$_4$ per liter), 7% SDS, 0.1-2 mg/ml denature DNA at 50° C., (4) 50% formamide, 5×SSC, 0.02 M Tris-HCl (pH 7.6), 1× Denhardt's solution (100=10 g Ficoll 400, 10 g polyvinylpyrrolidone, 10 g bovine serum albumin (fraction V), water to 500 ml), 10% dextran sulfate, 1% SDS, 0.1-2 mg/ml denatured salmon sperm DNA at 40° C., (5) 5×SSC, 5× Denhardt's solution, 1% SDS, 100 µg/ml denatured salmon sperm DNA at 50° C., or (6) 5×SSC, 5× Denhardt's solution, 50% formamide, 1% SDS, 100 µg/ml denatured salmon sperm DNA at 40° C., with low stringency washes of either 2×SSC, 0.1% SDS at 50° C., or (2) 0.5% bovine serum albumin (fraction V), 1 mM Na$_2$EDTA, 40 mM NaHPO$_4$ (pH 7.2), 5% SDS. The above conditions are intended to be used for DNA-DNA hybrids of 50 base pairs or longer. Where the hybrid is believed to be less than 18 base pairs in length, the hybridization and wash temperatures should be 5-10° C. below that of the calclated $T_m$ of the hybrid, where $T_m$ in ° C.=(2× the number of A and T bases)+(4× the number of G and C bases). For hybrids believed to be about 18 to about 49 base pairs in length, the $T_m$ in ° C.=(81.5° C.+16.6 (log$_{10}$M)+0.41(% G+C)–0.61 (% formamide)–500/L), where "M" is the molarity of monovalent cations (e.g., Na$^+$), and "L" is the length of the hybrid in base pairs.

The assays described herein can be used to detect pathogens, such as bacteria or viruses, or can be used to detect the expression of genes in a subject. For instance, genes from *Helicobacter pylori*, a pathogen implicated in gastric ulcers and cancer, were detected by the methods described herein. Two sequences belonging to the pathogenic microbe *Helicobacter pylori* are used to demonstrate the versatility and specificity of the assay: one that codes for an unique *H. pylori* protein and one that represents a small portion of the 23S rRNA from this organism. Both sequences can be detected into the nanomolar concentration range. In addition to reporting the presence of pathogen-related sequences, this assay can accurately resolve single-base changes in target sequences. An A2143C substitution within the *H. pylori* rRNA that confers antibiotic resistance significantly attenuates hybridization to an immobilized probe corresponding to the WT sequence. The single base mismatch introduced by this mutation slows the kinetics of hybridization and permits discrimination of the two sequences at short hybridization times. The assay described may therefore provide a means to detect and genotype infectious bacteria using electrochemical methods.

Figure 2A:
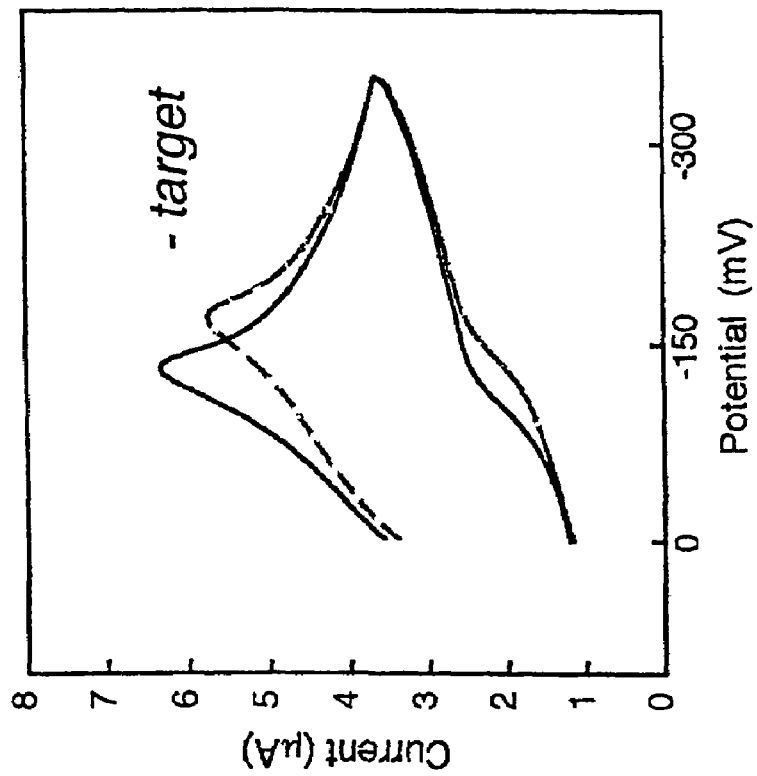
FIGS. 2A and 2B shows electrocatalytic hybridization detection of the Hpn sequence from H. pylori.
Figure 2B:
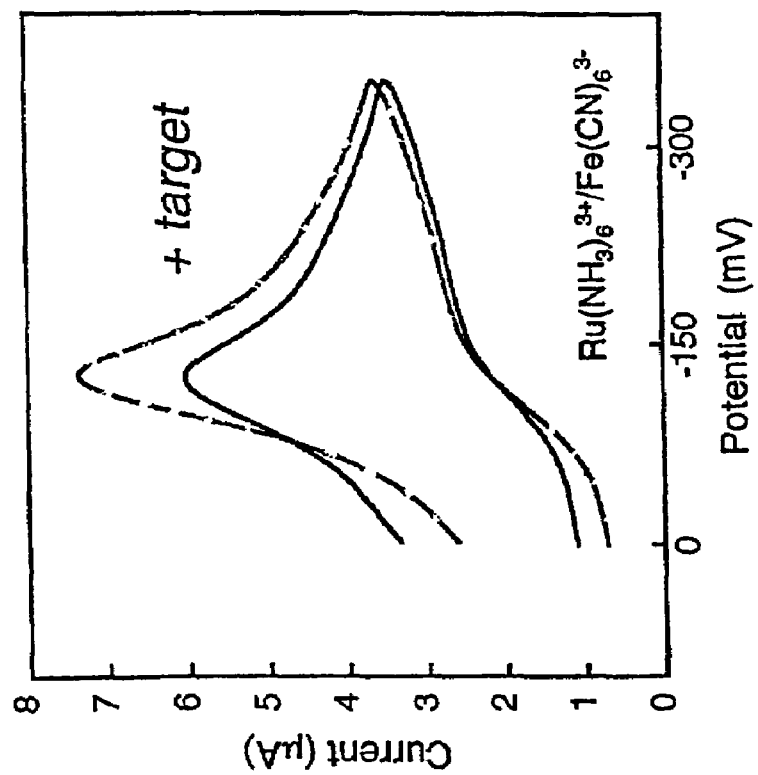

FIG. 1 shows a schematic of the electrocatalytic DNA hybridization detection system of the invention, which uses the increased loading of $Ru(NH_3)_6^{3+}$ resulting from the formation of a DNA duplex to report hybridization. The introduction of $Fe(CN)_6^{3-}$ makes the electrochemical reduction of this cation catalytic and amplifies the signal dramatically. FIG. 2 illustrates representative data obtained using this approach to detect a synthetic 30-mer modeling the Hpn gene from *Helicobactor pylori*, an infectious bacterium that is strongly linked with gastric ulcers and cancer. Gold electrodes were modified with single-stranded probe sequence, the electrodes treated with mercaptohexanol, and incubated in two heated buffer solutions (one which contained the target sequence (FIG. 2A), and the other which did not (FIG. 2B). Hybridization conditions were 40° C., 35 mM sodium phosphate, 100 mM NaCl, 25 Minutes, with or without 4 µM Hpn target sequence:

```
                                        (SEQ ID NO: 1)
5'-TGT TGC AGC ACT AGC GAT AGT CAT CAT CAA-3'
```

Figure 3:
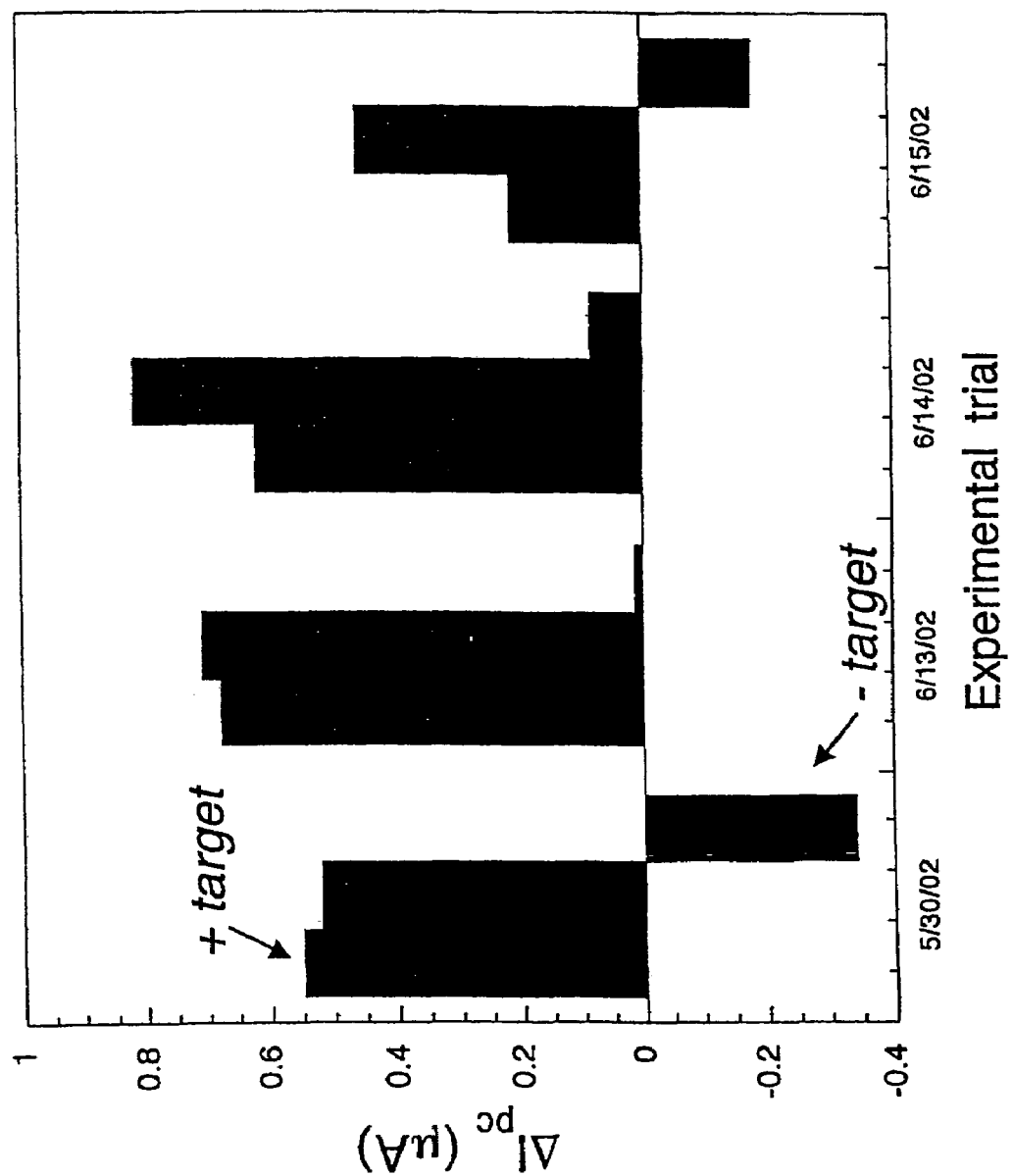
FIG. 3 is a histogram showing the reproducibility of the electrocatalytic hybridization detection. The tests described below and shown in FIG. 2 were performed on four different days.

The electrode exposed to the target sequence exhibited a pronounced increase in the electrochemical response, while that incubated in a buffer solution displayed a decreased response (this is a reproducible event—it appears that the heat treatment dislodges some loosely bound probe DNA). FIG. 3 shows the excellent reproducibility of the assay.

II Detection Nucleic Acids Using Nanoelectrode Ensembles (NEEs)

Another aspect of the present invention features utilizing the electocatalytic assays described herein on a device comprising oligonucleotide-functionalized metallic nanoelectrode ensembles for detecting extremely low levels of nucleic acid molecules. The application of the electrocatalytic assays on the nanoelectrode ensembles substantially expands the repertoire of nucleic acid detection scope to ultrasensitive biomolecular detection because the nanoelectrode ensembles provide very high sensitivity for biomolecular sensing.

The device for ultrasensitive detection of the nucleic acid molecules include an array of metallic nanoelectrode ensembles (NEEs) comprising a metallic nanowire embedded within a non-conductive substrate such as a polycarbonate membrane and a nucleic acid probe attached to the metallic nanowire. Preferably the metallic nanowire comprises gold. Preferably, the metallic nanowire ranges from about 10 to about 80 nanometers in diameter, and the nanowires have a density on the non-conductive substrate of from about $1\times10^8$ to about $1\times10^9$ per square centimeters.

In one embodiment, the array of the nanoelectrode ensembles of the present invention is two-dimensional, i.e., the nanowires on the nanoelectrodes do not protrude out of the non-conductive substrate. In another embodiment, the array of the nanoelectrode ensembles is three-dimensional, i.e., the nanowires on the nanoelectrodes protrude out of the non-conductive substrate. Preferably, the part of the nanowires that protrudes out of the non-conductive substrate is about 50 to about 300 nanometers, more preferably about 100 to about 200 nanometers.

Conventional techniques are used to prepare an array of the metallic nanowires and the nanoelectrode ensembles. See Menon, V P and Martin, C R, "Fabrication and Evaluation of Nanoelectrode Ensembles," *Anal. Chem.*, 67: 1920-1928 (1995), and Yu, S et al., "Nano Wheat Fields Prepared by Plasma-Etching Gold Nanowire-Containing Membranes," *Nano Lett.*, 3:815-818 (2004), which are hereby incorporated by reference. Generally, the non-conductive substrate containing nano-sized cylindrical pores is used as template for the preparation of the nanoelectrode ensembles. The metallic nanowires are deposited into the pores on the substrate. The procedure results in the metallic nanowires within the pores of the non-conductive substrate as well as thin metallic films that cover both faces of the substrate. Preferably, the metallic films on both of the surfaces can be removed by applying and then removing a strip of scotch tape. The metallic films on both faces are removed to yield the two-dimensional nanoelectrode ensembles. See FIG. 13A. To prepare three-dimensional nanoelectrode ensembles, the surface of the two-dimensional nanoelectrode ensembles is removed to expose the nanowires. See FIG. 13A. The length of the exposed nanowire is dependent on the etching time. For example, the longer etching times result in longer nanowire exposure.

A critical part of the nanoelectrode ensembles includes a nucleic acid probe which is attached to the exposed metallic nanowire on the non-conductive substrate. As used herein, "a nucleic acid probe" refers to a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified on bases (7-deazaguanosine, inosine, etc.) or on sugar moiety. In addition, the bases in a probe can be joined by a linkage other than a phosphodiester bond, so long as it does not interfere with hybridization. Thus, for example, probes can be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. By assaying for the presence or absence of the probe, one can detect the presence or absence of the select sequence or subsequence.

Various methods known in the art can be used for attaching the nucleic acid probe to the metallic nanowires. Preferably, the nucleic acid probe is attached to the metallic nanowire via a linker that imparts the shortest connectivity and provides the highest level of conjugation so that measured electrical conductivities correspond closely to the nucleic acid, and not to the properties of the linkers. Preferably, a thiol-terminated linker is used. In a preferred embodiment, the coupling method involves a solution-phase reaction between 4-mercaptobenzoic acid and a terminal amine either at the 3' or 5' position on the ribose moiety. This method provides a highly conjugated path between the gold particle and the DNA base stack. The incorporation of an amine at the 3' or 5' position is accomplished during chemical DNA synthesis by using commercially available reagents. A 3'-derivatization orients the DNA away from the gold surface when the linker is placed at the 3' end of an oligonucelotide, while the 5'-derivization provides the correct orientation for an oligonucleotide linked at the 5' end.

In another preferred embodiment, linker conjugation is achieved by the attachment of 4-mercaptobenzoic acid with a 5' pendant alkyl-amine or the incorporation of a short alkanethiol linker to the 3' end of DNA using a commercially-available reagent. These linkers give rise to more intervening σ-bonds between the gold surface and the DNA base stack, and can be used when a more insulating linker is desired, such as for example, in the construction of a single-electron transistor of the invention.

In another embodiment, one or plurality of the nucleic acid probe can be attached to a single metallic nanowire. The plurality of the nucleic acid probe on a single nanowire will help recognize an enhanced signal conducted to the detection device, thus, improve the sensitivity of the nucleic acid and reduce the background noise of the detection method.

Furthermore, the nucleic acid probe varies in length. In one embodiment, the probe can comprise about 7, preferably about 12, preferably about 15, more preferably about 25, 50, 75, 100, 125, 150, 175, 200, 250, 300, 350, or 400, or more nucleotides.

As for detection of a target nucleic acid in a sample using the nanoelectrode ensembles, generally, the detection is performed with a system comprised of nanoelectrode ensembles containing the nucleic acid probes attached thereto as work electrode and a reference electrode, wherein both electrodes are connected to a signal detection device. Upon contacting a sample containing a target nucleic acid with the nanoelectrode ensembles, the hybridization of the nucleic acid probe with the nucleic acid from the sample occurs and results in changes in electrodatalytic currents. The changes associated with the hybridization are reflected on the amplified signal on the detecting device and thus is indicative of the presence of the target nucleic acid in the sample.

To facilitate the nucleic acid detection, hybridization conditions can vary. For example, hybridization can be performed under high stringency, moderate stringency and low stringency conditions. The conditions of temperature and ionic strength determine the "stringency" of the hybridization. For preliminary screening for homologous nucleic acids, low stringency hybridization conditions, corresponding to a $T_m$ of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementary, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., *Molecular Cloning: A Laboratory Manual*, Cold Spring Harbor Laboratory Press, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8). Preferably a minimum length for a hybridizable nucleic acid is at least about 10 nucleotides; preferably at least about 15 nucleotides; and more preferably the length is at least about 20 nucleotides; and most preferably 30 nucleotides.

For the electrochemical detection method to work on nanoelectrode ensembles, the detection method includes contacting the array of nanoelectrode ensembles with a sample under a hybridization condition and detecting an increase in the amplified signal on the circuit that is associated with the hybridization of the nucleic acid probe on the nanoelectrode to the target nucleic acid in the sample. The increase in the signal indicates the presence of the target nucleic acid in the sample. Furthermore, the electrochemical detection method can be used to quantitatively detect the amount of the target nucleic acid in the sample. In one embodiment, the change in the amplified signal after the hybridization relative to the signal before the hybridization can be compared to a standard for obtaining the amount of the target nucleic acid in the sample. Alternatively, the amplified signal after hybridization can be compared to the signal associated with the hybridization of the nucleic acid to a control sample containing no target nucleic acid. The amount of the target nucleic acid in the sample can be deduced from the difference in the amplified between the two.

The sample is placed in contact with the array of nanoelectrode ensembles. The contact can take place in any suitable container. Generally, the incubation of the sample in contact with the array is at temperatures normally used for hybridization of the target nucleic acid in the sample to the nucleic acid probe.

The target nucleic acid to be detected can be isolated from samples like a bodily fluid from an animal, including a human, such as, but not limited to, blood, urine, lymphatic fluid, synovial fluid, bile, phlegm, saliva, menstrual fluid and semen. In addition, samples containing DNA or RNA can, for example, be found in fluids from a plant, such as, but not limited to, xylem fluid, phloem fluid and plant exudates. Samples containing DNA or RNA may, for example also be found in non-living sources such as, but not limited to, food, sewage, forensic samples, lakes, reservoirs, rivers and oceans. Target polynucleotides can also be those of defunct or extinct organisms, e.g., pressed plants in herbarium collections, or from pelts, taxidermy displays, fossils, or those of biological materials in museum collections. When whole cells, viruses or other tissue samples are analyzed, it is necessary to extract the nucleic acids from the cells, viruses or the tissue samples. Following sample collection, nucleic acids can be liberated from the cells, viruses or tissues. It is also necessary to separate the nucleic acids from other elements of the crude extract, e.g., denatured proteins, cell membrane particles and the like. Various methods well known in the art can be used to carry out the separation.

The target nucleic acid molecule can optionally be amplified prior to detection by the method of the present invention. The target nucleic acid can be in either a double-stranded or single-stranded form. In the case where the target nucleic acid molecule is double-stranded, it is preferably first treated by a denaturation agent to render the two strands into a single-stranded, or partially single-stranded form, at the start of the amplification reaction, by methods known in the art such as heating, alkali treatment, or by enzymatic methods. General methods for accomplishing this treatment are provided by Sambrook, J. et al., *Molecular Cloning: A Laboratory Manual*, Cold Spring Harbor Laboratory Press, Cold Spring Harbor, N.Y., U.S.A. (1989).

Once the sample has been treated to expose any target nucleic acid, the solution can be tested as described herein to detect hybridization between the attached nucleic acid and the target nucleic acid, if such is present. Alternatively, some samples can be tested directly, e.g., the target may exist in a serum sample and can be directly accessible, and may not require treatment to release the nucleic acid.

The detection method using nanoelectrode ensembles can be used for various applications such as for detection of human genes or mutations, detection of pathogens, such as bacteria or viruses, or can be used to detect the expression of genes in a subject. For instance, genes from *Helicobacter pylori*, a pathogen implicated in gastric ulcers and cancer, can be detected by the methods described herein. Two sequences belonging to the pathogenic microbe *Helicobacter pylori* are used to demonstrate the versatility and specificity of the assay: one that codes for an unique *H. pylori* protein and one that represents a small portion of the 23S rRNA from this organism. Both sequences can be detected into the femtomolar concentration range.

The detection method of the present invention using nanoelectrode ensembles offers numerous advantages over those other detection methods. Such advantages include very high sensitivity, good control, good reproducibility, label free and simple operation and instrumentation. With the detection method of the present invention using nanotechology, as few as around 1000 nucleic acid molecules can be detected.

The invention is further illustrated by the following examples, which are not intended to be limiting.

EXAMPLES

Example 1

Materials and Methods

Chemicals and materials. DNA synthesis reagents were obtained from Glen Research. 1,6-hexamethylenediamine, 99.8% anhydrous 1,4-dioxane, 6-mercapto-1-hexanol (97%) (MCH), and potassium ferrocyanide trihydrate were received from Aldrich Chemical Company. Potassium ferricyanide, 1,1'-carbonyldiimidazole, and hexaammineruthenium chloride were purchased from Acros Organics. N-succinimidyl 3-(2-pyridyldithio)propionate (SPDP) was purchased from Pierce. Dithiothreitol (DTT) and 2-mercaptoethanol were obtained from Fisher Scientific. Gold-coated silicon wafers were received from Platypus Technologies. Cloned Pfu DNA polymerase was obtained from Stratagene.

Preparation and purification of modified oligonucleotides. Oligonucleotides were synthesized using an ABI 394 DNA/RNA synthesizer according to standard automated solid-phase techniques. Oligonucleotides modified at the 5'-terminus with hexanediamine-based linker (C6) were prepared and purified as described previously.[25] All unmodified oligonucleotides were stringently purified using reversed phase HPLC. The following probe and target sequences were used in experiments employing synthetic oligonucleotides:

HP1a (30 nt complementary hpn probe):
(SEQ ID NO: 12)
SH-5'TTGATGATGACTATCGCTAGTGCTGCAACA3'

HP1b (18 nt + 12T complementary hpn probe)
(SEQ ID NO: 4)
SH-5'TTTTTTTTTTTTGATGACTATCGCTAGTGC3'

-continued

HP1c (18 nt + 12T noncomplementary hpn probe)
(SEQ ID NO: 5)
SH-5'TTTTTTTTTTTTGGGATAATTCTTCACCGG3'

HP2a (rRNA probe):
(SEQ ID NO: 13)
SH-5'GGGTCTTTCCGTCTTGCC3'

HP2b (rRNA probe-2):
(SEQ ID NO: 14)
SH-5'GGTCCACGGGGTCTTTCC3'

T1 (hpn target)
(SEQ ID NO: 1)
5'TGTTGCAGCACTAGCGATAGTCATCATCAA3'

T2a (WT rRNA target):
(SEQ ID NO: 2)
5'GGCAAGACGGAAAGACCC3'

T2aMUT (A2143C rRNA target):
(SEQ ID NO: 3)
5'GGCAAGACGGA<u>C</u>AGACCC3'

T2b (WT rRNA target #2):
(SEQ ID NO: 15)
5'GGAAAGACCCCGTGGACC3'

T2bMUT (A2143C rRNA target #2):
(SEQ ID NO: 16)
5'GGA<u>C</u>AGACCCCGTGGACC3'

(in both A2143C rRNA sequences, the site of the resistance mutation is underlined.)

T-NC (noncomplementary target):
(SEQ ID NO: 17)
5'AAC AGT TCC TGC ATG3'

Probe strands featuring fluorescein attached to the base at the 3'-terminus were synthesized using a fluorescein-dT CPG (Glen Research) and modified with a thiol-terminated linker as described previously. Fluorescein attachment to target strands was achieved with a 5'-fluorescein phosphoramidite following standard automated solid phase techniques. Fluorescein-modified oligonucleotides were purified by reversed phase HPLC.

Modification of gold surfaces with probe DNA. Single-stranded thiolated probes were immobilized on bulk gold electrodes with A=0.02 cm$^2$ (Bioanalytical Systems). Prior to probe immobilization, gold electrodes were polished using 0.05 μm alumina, rinsed in water, sonicated for 5 mm, etched by scanning from 0-1.8 V at 200 mV/sec in 1M $H_2SO_4$, and rinsed with water. Inverted gold electrodes were typically exposed to ssDNA thiolated probes in solutions containing 5 μM SH-DNA, 500 nM MCH, 25 mM sodium phosphate (pH 7), 25 mM NaCl, and 50 mM $MgCl_2$ in a humidity chamber at room temperature for 1 hour. (Any deviations from these conditions are described in individual figure captions.) Manipulation of probe film densities was achieved with solutions containing variable amounts of $MgCl_2$ ranging from 10-100 mM. Following deposition, electrodes were rinsed in 25 mM sodium phosphate (pH 7), 25 mM NaCl buffer. The adsorption of DNA on the electrode surface was confirmed by monitoring the blocking of 2 mM ferrocyanide in 25 mM sodium phosphate (pH 7), 25 mM NaCl.

Hybridization of target sequences. Gold electrodes modified with thiolated ssDNA were exposed to target sequences and hybridization was detected through enhancement of the electrocatalytic signal. Prior to hybridization of target, initial electrocatalytic measurements of immobilized ssDNA probes were recorded and upon hybridization of target the change in signal could be calculated.

Electrochemical measurements. Electrochemical measurements were conducted with a Bioanalytical Systems CV-50 potentiostat. A one-compartment cell fitted with a Luggin capillary was used. All cyclic voltammetry measurements were conducted at room temperature with a Bioanalytical Systems CV-50W potentiostat. A three-electrode configuration was used consisting of a modified gold working electrode, a platinum wire auxiliary electrode, and an Ag/AgCl reference electrode. A one-compartment cell fitted with a Luggin capillary was used to separate the working compartment from the reference compartment.

Electrocatalytic currents were measured in solutions of 2 mM $Fe(CN)_6^{3-}$, 27 µM $Ru(NH_3)_6^{3+}$ in 25 mM sodium phosphate/250 mM NaCl (pH 7) at a scan rate of 100 mV/s. Cathodic charge (Q) was quantitated by integrating background-subtracted voltammograms. Signal changes corresponding to hybridization were calculated as follows $\Delta Q = (Q_{final} - Q_{initial})/Q_{initial}$. Error bars shown on individual figures correspond to variabilities among multiple independent trials of each experiment.

Electrochemical Detection of Target Hybridization

The electrocatalytic current obtained at gold electrodes modified with thiolated probe DNA was measured, and rinsed electrodes were then exposed to target sequences and hybridization was detected through enhancement of the electrocatalytic signal. Hybridization solutions typically contained 500 nM-20 µM target DNA in 25 mM sodium phosphate (pH 7), 25 mM NaCl, 100 mM $MgCl_2$. Electrodes were incubated at 37-50° C. in a thermostatted humidity chamber and were washed extensively with buffer before electrochemical analysis. The conditions used for individual experiments varied depending on the size and source of the target nucleic acid; details of different hybridization trials are provided in the figure captions.

Fluorescence-based Quantitation of Surface Coverage and Hybridization Efficiencies.

Quanatitation of electrode surface coverage using fluorescein-labeled DNA was achieved based on the procedure described by Demers et al. Prior to the deposition of fluorophore-labeled DNA, bulk gold electrodes were prepared as described above with electrochemical etching. Larger (0.28 cm$^2$) flat gold surfaces were cleaned in Piranha solution (3:1 $H_2SO_4/H_2O_2$) for 20 minutes followed by stringent washing in water. Using a guide producing an area of 0.28 cm$^2$, 3'-fluorescein-5'-thiol modified oligonucleotide was incubated on the gold surface for 1 hour at room temperature in a humidity chamber. Probe immobilization was performed using a solution containing 5 µM 3'-fluorescein-5'-thiol probe, 500 nM MCH, 25 mM sodium phosphate (pH 7), 25 mM NaCl and varied amounts of $MgCl_2$ (10 mM to 100 mM). Substrates treated with noncomplementary probes were used as controls. After deposition, gold surfaces were washed extensively with 25 mM sodium phosphate (pH 7), 25 mM NaCl. Fluorophore-modified probes were then displaced with 12 mM mercaptoethanol for approximately 3-4 hours at room temperature in a humidity chamber; a second round of displacement was conducted overnight. Fluorescence intensities for calibration standards and samples removed from the gold surface were measured in 50 mM NaOH (pH 12) on a Wallac VictorF fluorescence plate reader. Amounts of 3'-fluorescein-5'-thiol modified oligonucleotide displaced from the surface were determined by interpolation from a standard linear calibration curve prepared with known concentrations of the modified probe.

For the measurement of hybridization efficiencies using fluorescence, labeled target sequences were introduced from solutions containing 5 µM target (F1-T2), 25 mM sodium phosphate (pH 7), 25 mM NaCl, and 100 mM $MgCl_2$ for 1 hour in a 40° C. incubator. The surfaces were then stringently washed with 25 mM sodium phosphate (pH 7), 25 mM NaCl to remove non-hybridized target. Displacement of duplexes and fluorescence measurements were performed as described above. A standard linear calibration curve was plotted using known concentrations of duplex DNA (BP2a/F1-T2).

Thermal Denaturation of Probe/target Duplexes

Thermal denaturation measurements were performed with solutions containing 1 µM of complementary strands in 25 mM sodium phosphate (pH 7), 25 mM NaCl. Measurements were obtained by monitoring absorbance at 260 nM on an AVIV spectrophotometer.

Example 2

Fabrication of DNA-modified Surfaces

The appendage of a thiol-terminated linker to synthetic oligonucleotides permits the self-assembly of DNA films on gold electrodes. Gold surfaces modified with single-stranded oligonucleotides have been prepared by several groups interested in monitoring electrochemical processes in the presence of DNA. The films used in the experiments described here feature oligonucleotides containing an aliphatic linker that is attached post-synthetically using a combination of solid- and solution-phase synthesis. A co-adsorbent, mercaptohexanol, is introduced during deposition to decrease the density of adsorbed DNA and to minimize non-specific DNA binding at the gold surface.

The conditions employed here for deposition produce high-density films from thiol-modified oligonucelotides within minutes and have coverages that depend on the amount of divalent cation used in the deposition solution. Using fluorescein-modified oligonucleotides, it was determined that densities of 12(±2), 23(±3), and 27(±4) pmol/cm$^2$ of single-stranded oligonucleotides were obtained with 10, 50, or 100 mM $MgCl_2$ present in the deposition buffer, respectively. Probe-density measurements were made both on bulk gold electrodes and vapor-deposited gold substrates to confirm that comparable densities existed (working with the larger substrates was desirable for more accurate quantitation of the less dense coverages). Coverages comparable to those measured here with low [Mg$^{2+}$] were observed in previous studies where deposition was performed in the presence of 10 mM sodium phosphate and 100 mM NaCl.

For the electrochemical experiments described below, DNA films were used that were formed with 50 mM $MgCl_2$ present during deposition. While sparser surface coverages promote more efficient DNA hybridization (vide infra), greater reproducibility was achieved with higher DNA densities that produced larger voltammetric signals.

Example 3

Detection of Target DNA Sequences Based On the Electrocatalytic Reduction of $Ru(NH_3)_6^{3+}$ at DNA-Modified Surfaces $Ru(NH_3)_6^{3+}$, lacking any ligands that can bind to DNA intercalatively, associates electrostatically with the negatively charged backbone. It is therefore a sequence-neutral binder and an ideal probe for quantitating DNA adsorbed on an electrode surface.[26] Monitoring hybridization with $Ru(NH_3)_6^{3+}$ would potentially provide a means to detect DNA electrochemically. However, the films with sparser surface coverages that permit efficient hybridization only yield small signals for this redox-active species.

Figure 4:
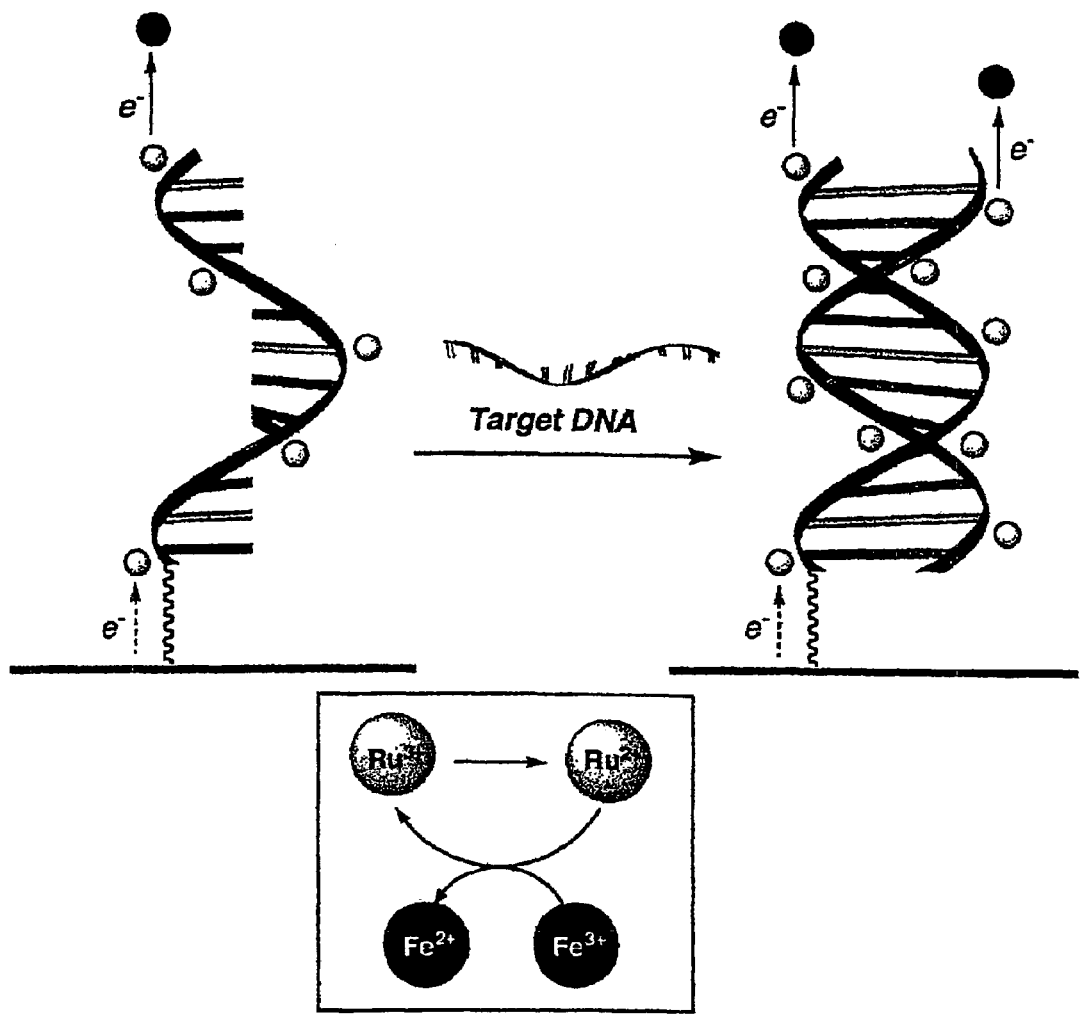
FIG. 4 is an illustration of electrocatalytic detection of DNA hybridization.
Figure 6:
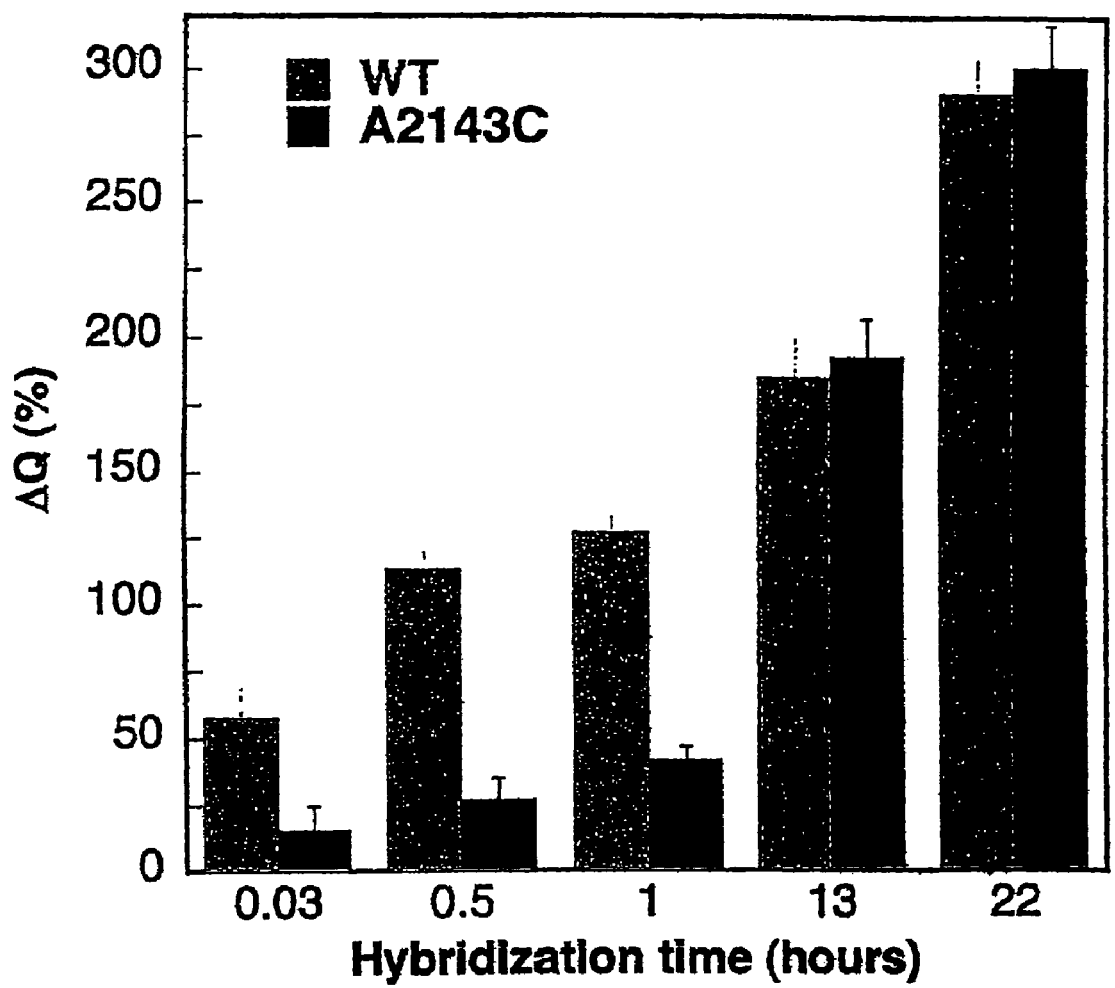
FIG. 6 is a bar graph showing the time dependence of hybridization for WT and A2143C sequences corresponding to a fragment of the H. pylori 23S rRNA.

To amplify signals obtained at DNA-modified electrodes in the presence of $Ru(NH_3)_6^{3+}$, we introduced an oxidant, $Fe(CN)_6^{3-}$, that would permit turnover of $Ru(NH_3)_6^{3+}$ by regenerating the oxidized form (FIG. 4). As shown in FIG. 5, large, irreversible reductive waves are observed at DNA-modified electrodes immersed in solutions of $Fe(CN)_6^{3-}$ and $Ru(NH_3)_6^{3+}$, consistent with the proposed reaction cycle (FIG. 5). The electrochemical signals obtained with DNA-modified electrodes from solutions of Ru(III) and Fe(III) are amplified by ~100-fold over those obtained when only $Ru(NH_3)_6^{3+}$ is present (no signal is obtained in this region when only $Fe(CN)_6^{3-}$ is present). The electrocatalysis requires DNA to attract the cation to the gold surface, as no signal is observed with a bare electrode.

This assay sensitively reports the presence of a target DNA sequence. The Ru(III)/Fe(III) signal monitored at a gold electrode modified with a probe sequence complementary to a portion of the *H. pylori* 23S rRNA gene (sequence: 5'-GGC AAG ACG GAA AGA CCC-3' (SEQ ID NO: 2)) significantly increases after exposure of the electrode to a synthetic target oligonucleotide (FIG. 5). The change in the electrochemical response is barely detectable in the absence of Fe(III). Short hybridization times (<1 hour) under mild conditions (40° C.) are sufficient to observe an increase in the electrocatalytic signal of >100%. In the presence of noncomplementary sequences or buffer lacking any DNA, no appreciable signal differences are observed.

The Ru(III)/Fe(III) electrocatalysis accurately reports hybridization of sequences of difference lengths and base composition. Both the 18-nt 23S rRNA sequence described above and a 30-nt sequence corresponding to a fragment of the Hpn gene (which encodes a protein unique to *H. pylori*, sequence: 5'-TGT TGC AGC ACT AGC GAT AGT CAT CAT CAA-3' (SEQ ID NO: 1)) can be detected as shown in FIG. 5A. It is also sensitive, as target concentrations down to 10 nM produced measurable increases in the electrochemical response after hybridization.

Example 4

Discrimination of Targets Containing Single-Base Substitutions

In experiments monitoring the hybridization of DNA oligonucleotides corresponding to a region of the *H. pylori* 23S rRNA, a pronounced sensitivity to mismatched base pairs within the target/probe complex was observed. The enhancement in the electrochemical signal typically observed with the WT rRNA sequence was significantly diminished when an A-to-C substitution at position 2143 within the 23S rRNA was introduced (sequence: 5'-GGC AAG ACG Gac AGA CCC-3' (SEQ ID NO: 3), the nucleotide corresponding to C2143 is in lower case). The A2143C variant is important because this substitution imparts resistance to clarithromycin, the antibiotic typically used to combat *H. pylori*, and about 10% of the infections observed clinically are clarithromycin resistant.

The discrimination of the A2143C mutant is a result of slower hybridization kinetics for the sequence that is mismatched with respect to the probe. A systematic study of the hybridization efficiency as a function of time for the WT versus A2143C target revealed that the extent of hybridization for the two sequences only becomes comparable with incubation times over 12 hours. The pronounced effect caused by the single-base mismatch within the target/probe complex is a significant finding. Previous studies of duplex hybridization in solution by other groups have characterized much more subtle effects, with association rates for two DNA oligonucleotides displaying little sensitivity to the loss of a single Watson-Crick pair, and dissociation rates that increase by about an order of magnitude in mismatched assemblies.[27] Therefore, it appears that heterogeneous hybridization reactions, with one oligonucleotide immobilized on an electrode surface, are much more sensitive to mismatches, a finding that provides the basis for distinguishing similar sequences with an electrochemical hybridization assay. The probe density that we use in our experiments also appears to amplify the effect, as studies using surface plasmon resonance to follow hybridization at gold surfaces with very low surface coverages have elucidated similar, but much less pronounced, effects.[22] A surface with a high coverage of negatively charged oligonucleotides may serve to further destabilize mismatched target/probe duplexes.

The electrocatalytic DNA detection assay described provides a sensitive and specific means to execute electrochemical genotyping. The method described will be useful for genetic analysis in a multiplexed format.

Example 5

Hpn Target Detection Using PCR Products, RNA Transcripts, and a Synthetic 30-mer Two probe sequences were tested with the different targets: HP2a (complementary Hpn probe) 5'-TTT TTT TTT TTT GAT GAC TAT CGC TAG TGC-3' (SEQ ID NO: 4) and HP2b (noncomplementary Hpn probe) 5'-TTT TTT TTT TTT GGG ATA ATT CTT CAC CGG-3' SEQ ID NO: 5). The appended thymine bases allowed for the probe to be more accessible to he target. The complementary probe effectively detects the presence of the different target nucleic acids using the elctrocatalytic Ru(III)/Fe(III) system.

The target sequences were as follows:

PCR (generated using asymmetric PCR as single-stranded DNA, portion complementary to probe is underlined):

```
5'-GGA GTC ATC ATG GCA CAC CAT GAA GAA CAG CAC GGC GGT CAT CAC CAC   (SEQ ID NO: 6)

CAT CAC CAC CAC ACA CAC CAC CAC CAC TAT CAC GGC GGT GAA CAC CAC CAT

CAC CAC CAC AGC TCT CAT CAT GAA GAA GGT TGT TGC AGC ACT AGC GAT AGT

CAT CAT CAT CAA GAA GAG GGT TGC TGC CAC GGG CAT CAC GAG TAA TAT CGG

TGT GGC TAG GGG CAA CTT-3'
```

RNA (same sequence as PCR product, generated in vitro from DNA template, portion complementary to probe is underlined):

```
5'ATC AAA GGA GTC ATC ATG GCA CAC CAT GAA GAA CAG CAC GGC GGT CAT    (SEQ ID NO: 7)

CAC CAC CAT CAC CAC CAC ACA CAC CAC CAC CAC TAT CAC GGC GGT GAA CAC

CAC CAT CAC CAC CAC AGC TCT CAT CAT GAA GAA GGT TGT TGC AGC ACT AGC

GAT AGT CAT CAT CAT CAA GAA GAG GGT TGC TGC CAC GGG CAT CAC GAG TAA

TAT CGG TGT GGC TAG GGG CAA CTT-3'
```

30-mer synthetic oligo (SEQ ID NO: 8)
5'-TGT TGC AGC ACT AGC GAT AGT CAT CAT CAT CAA-3'

DNA probe solutions (HP2a and HP2b) containing 5 µM ssDNA, 500 nM MCH, 50 mM MgCl$_2$, and 25 mM sodium phosphate/NaCl buffer pH 7 were deposited for 1.5 hours at room temperature in humidity chamber. Target solution containing synthetic 30-mer and PCR product contained 500 nM target, 100 mM MgCl$_2$, and 25 mM sodium phosphate/NaCl buffer pH 7 and were exposed to DNA films for 1 hour at 45° C. RNA target hybridization was under the same conditions except 1 µM target was used.

Figure 7:
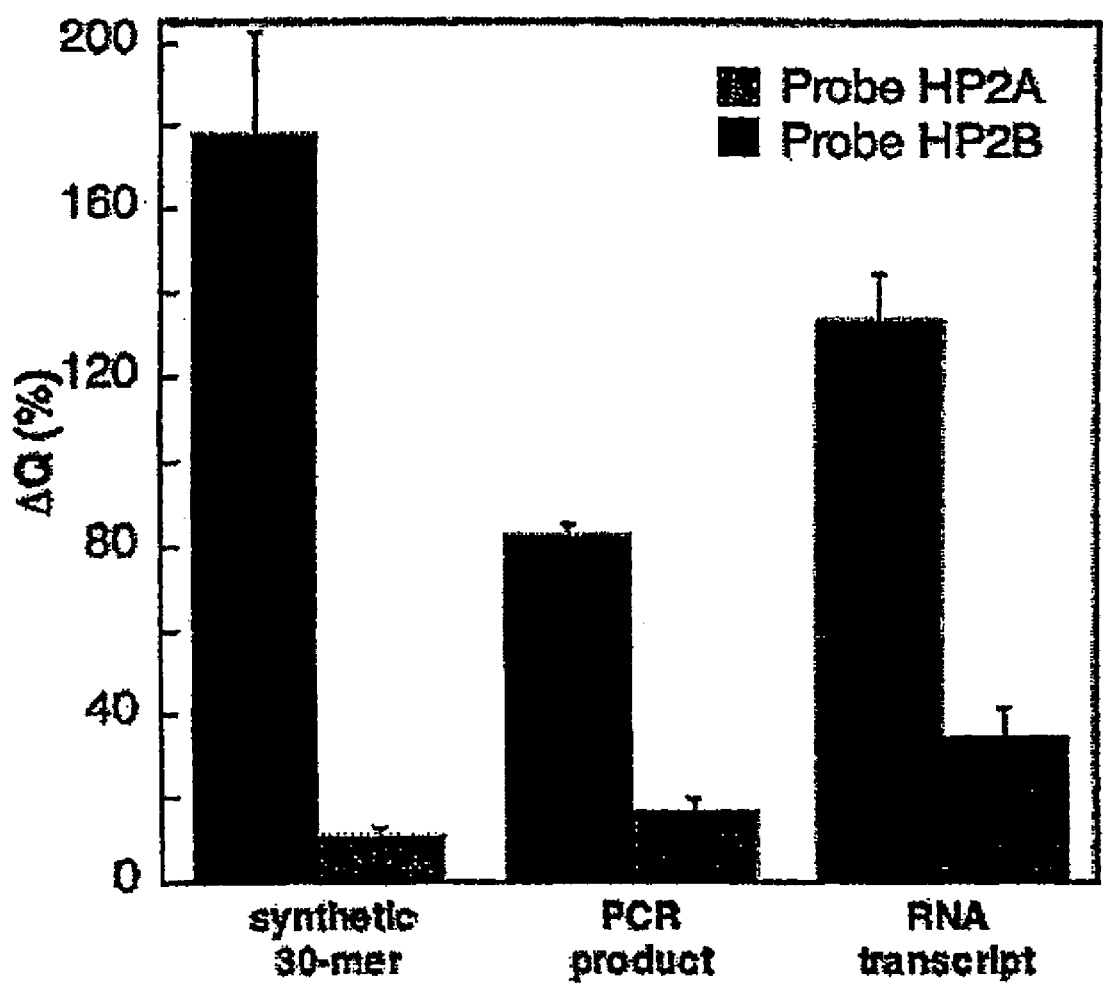
FIG. 7 is a bar graph showing the time dependence of hybridization for HP2A probe (complementary Hpn probe) and HP2B probe (noncomplementary Hpn probe).

The results are shown in FIG. 7, which is a bar graph showing the time dependence of hybridization for HP2A probe (complementary Hpn probe) and HP2B probe (non-complementary Hpn probe). It shows that target DNA sequences can be detected as either PCR products or RNA transcripts using the methods described herein.

Example 6

Preparation of Asymmetric PCR Amplicon and RNA Targets

The *H. pylori* hpn gene was PCR amplified from a recombinant source (an *E. coli* plasmid provided by Dr. Andrew Plaut of Tufts University). Two PCR products were generated, one using the asymmetric method that produces mainly single-stranded DNA, and another using conventional PCR conditions that would generate a double-stranded product for T7 runoff transcription of RNA. For the former reaction, a forward PCR primer (5'-ATC AAA GGA GTC ATC ATG GCA CAC-3' (SEQ ID NO: 9)) and reverse PCR primer (5'-AAG TTG CCC CTA GCC ACA-3' (SEQ ID NO: 10)) were used in reactions containing 1 µg/ml of plasmid DNA, 500 nM forward primer, 5 nM reverse primer, 1× of cloned Pfu DNA polymerase reaction buffer (200 mM Tris-HCl (pH 8.8), 100 mM KCl, 100 mM (NH$_4$)$_2$SO$_4$, 20 mM MgSO$_4$, 1% Triton X-100, 1 mg/ml nuclease-free bovine serum albumin), 1 mM dNTPs, and 2.5 U of cloned Pfu DNA polymerase, polymerase buffer and enzyme purchased from Stratagene, in a total reaction volume of 100 µL. For the synthesis of the PCR product used for the generation of the RNA transcript, a forward PCR primer containing the T7 polymerase promoter sequence (5'-GCT AGG TAA TAC GAC TCA CTA TAG GAG TCA TCA TGG CAC AC-3' (SEQ ID NO: 11)) was used with the same reaction conditions with the exception of the addition of 500 nM forward and 500 nM reverse primer. PCR was performed on a Stratagene Robocycler with 30 cycles at 94° C. for 2 minutes, 52° C. for 2 minutes, 72° C. for 3 minutes. PCR products were subjected to phenol-chloroform extraction and ethanol precipitation. RNA target was transcribed from amplified DNA template with T7 promoter region using standard conditions. The resultant DNA and RNA targets had the following sequences:

(SEQ ID NO: 6)
5'GGAGTCATCATGGCACACCATGAAGAACAGCACGGCGGTCATCACCAC
CATCACCACCACACACACCACCACCACTATCACGGCGGTGAACACCACCA
TCACCACCACAGCTCTCATCATGAAGAAGGTTGTTGCAGCACTAGCGATA
GTCATCATCATCAAGAAGAGGGTTGCTGCCACGGGCATCACGAGTAATAT
CGGTGTGGCTAGGGCAACTT3' (RNA, 219 nt)
and (SEQ ID NO: 7)
5'ATCAAAGGAGTCATCATGGCACACCATGAAGAACAGCACGGCGGTCAT
CACCACCATCACCACCACACACACCACCACCACTATCACGGCGGTGAACA
CCACCATCACCACCACAGCTCTCATCATGAAGAAGGTTGTTGCAGCACTA
GCGATAGTCATCATCATCAAGAAGAGGGTTGCTGCCACGGGCATCACGAG
TAATATCGGTGTGGCTAGGGGCAACTT3' (DNA, 225 nt);

the portion of the sequence that is complementary to the HP1b probe is underlined.

Example 7

Electrocatalytic Reduction of Ru(NH$_3$)$_6^{3+}$ at DNA-modified Surfaces

Ru(NH$_3$)$_6^{3+}$, lacking any ligands that can bind to DNA intercalatively, associates electrostatically with the negatively charged backbone. It is therefore a sequence-neutral binder and an ideal probe for the quantitation of single- or double-stranded DNA adsorbed on an electrode surface. However, the limited concentration of Ru(NH$_3$)$_6^{3+}$ localized at DNA-modified electrodes yields a small current under conditions suitable for hybridization detection (i.e. concentrations of Ru(III) sufficiently low to prohibit direct adsorption of the redox-active probe). To provide maximal sensitivity for the detection of DNA hybridization, we introduced an oxidant, Fe(CN)$_6^{3-}$, that would permit turnover of Ru(NH$_3$)$_6^{3+}$ by regenerating the oxidized form (Scheme 1), thereby significantly amplifying the response obtained.

Indeed, as shown in FIG. 8, large, irreversible reductive waves are observed using cyclic voltammetry (CV) at DNA-modified electrodes immersed in solutions of Fe(CN)$_6^{3-}$ and Ru(NH$_3$)$_6^{3+}$, consistent with the proposed reaction. The amount of current observed reports the quantity of DNA present at the electrode surface, as the response obtained at surfaces featuring different densities (controlled by varying

[Mg$^{2+}$] during deposition) was directly dependent on the number of DNA molecules immobilized.

The electrochemical signals obtained with DNA-modified electrodes from solutions of Ru(III) and Fe(III) are amplified by ~100-fold over those obtained when only Ru(NH$_3$)$_6^{3+}$ is present (FIG. 8B inset); no signal is obtained in this region when only Fe(CN)$_6^{3-}$ is present (data not shown). The electrocatalysis requires DNA to attract the cationic complex to the gold surface, as no signal is observed with a bare electrode.

The electrocatalytic assay sensitively reports the presence of a complementary target DNA sequence. The Ru(NH$_3$)$_6^{3+}$/Fe(CN)$_6^{3-}$ signal monitored at a gold electrode modified with a probe sequence complementary to a portion of the *H. pylori* 23S rRNA gene (nucleotides 2132-2149) significantly increases after exposure of the electrode to a synthetic target oligonucleotide (FIG. 8B). Short hybridization times (<1 hour) and mild conditions are sufficient to observe an increase in the integrated charge of >100%. In the presence of non-complementary sequences or buffer lacking any DNA, no appreciable signal differences are observed.

Figure 9:
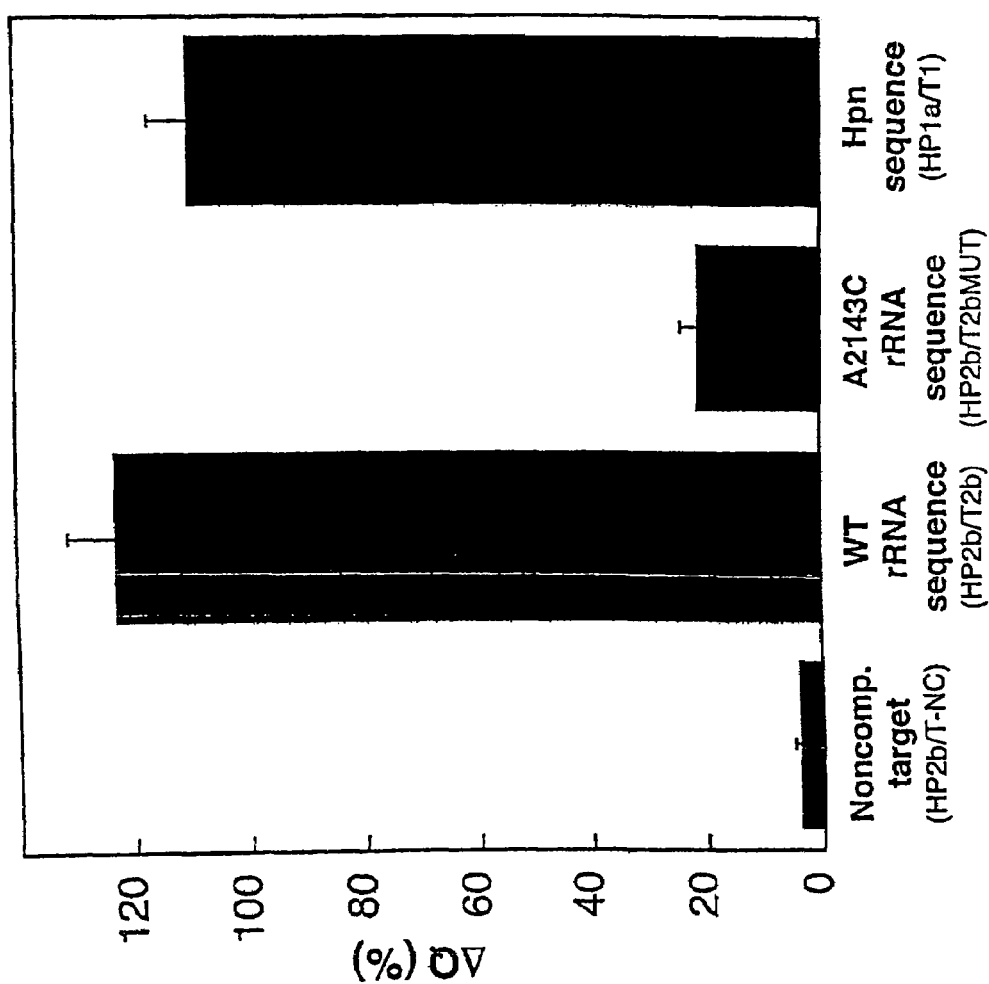
FIG. 9 shows detection of H. pylori-related sequences through changes in integrated charge obtained using electrocatalysis. Cyclic voltammetry was used to quantitate charge at electrodes exposed to different target/probe sequence pairs. Films of DNA probe sequences (HP2b and HP1a) were prepared as described in FIG. 8 with the exception that the 30-nucleotide probe sequence (HP1a) was deposited for 1.5 hours. The average integrated charge measured at probe-modified electrodes prior to hybridization is shown as a dotted line. Hybridization of all target sequences was allowed to proceed for 30 minutes and was otherwise performed as described in FIG. 8 with the exception of the inclusion of 200 mM $MgCl_2$ in the hybridization solution for the hpn target (T1).

The Ru(III)/Fe(III) electrocatalysis accurately reports hybridization of sequences of different lengths. Both the 18 nucleotide 23S rRNA sequence described above and a 30 nucleotide sequence corresponding to a fragment of the hpn gene (which encodes a histidine-rich protein of unknown function unique to *H. pylori*) can be detected as shown in FIG. 9. Thus, the assay described is versatile and is compatible with different probe sequence lengths and base composition. It is unnecessary to match the length of the target and probe, as experiments where the size of the target was increased by 10-15 nucleotides also produced successful hybridization detection (data not shown). The electrocatalytic assay is also sensitive, as target concentrations down to 10 mM (50 fmol) produced measurable increases in the electrochemical response after hybridization.

Example 8

Effect of Immobilized Probe Density

Figure 10:
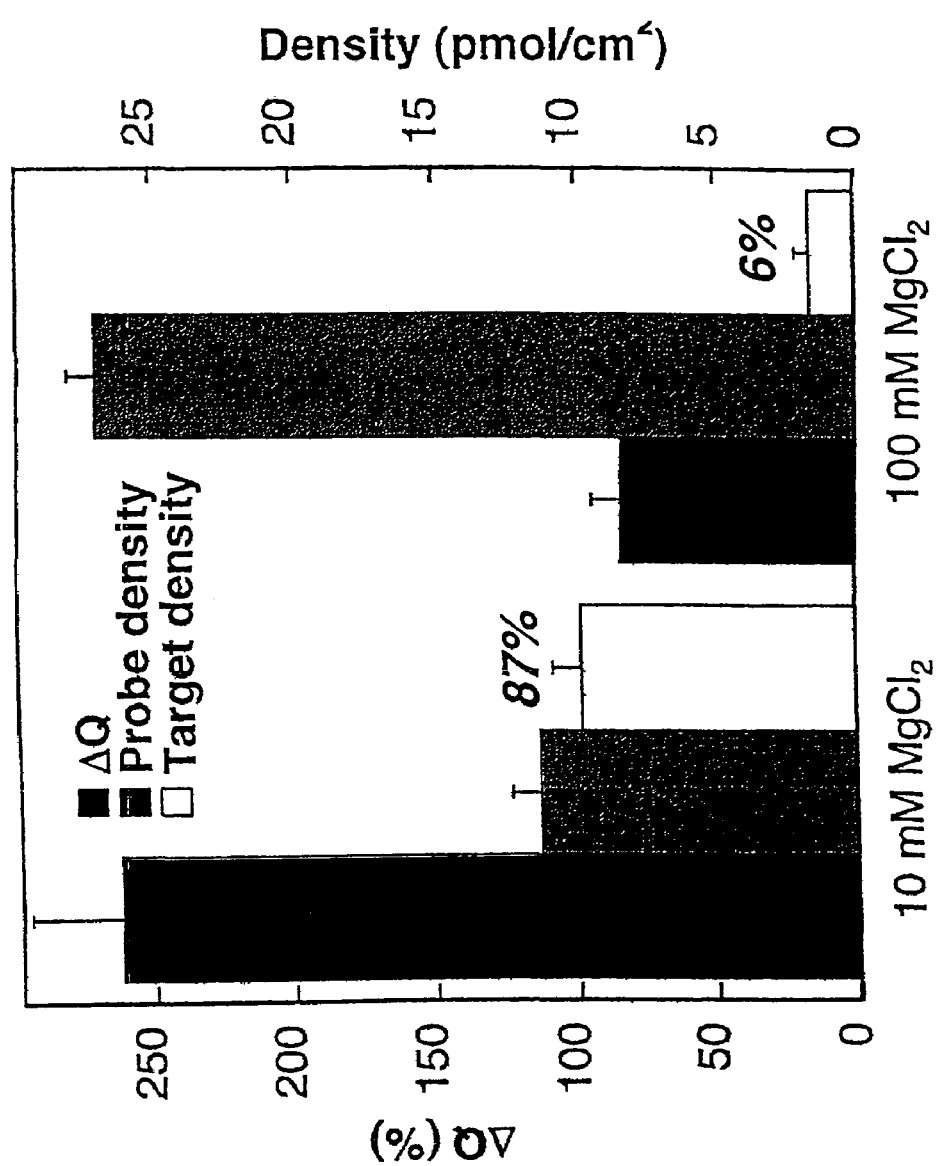
FIG. 10 shows dependence of hybridization efficiency on surface coverage. Fluorescein-modified thiolated probes and target sequences were used to quantitate absolute surface coverages, and cyclic voltammetry was used to quantitate changes in charge upon hybridization. The probe (HP2a) and target sequences (T2a) and experimental conditions are identical to FIG. 8A.

The efficiency of hybridization, investigated using the electrocatalytic assay and fluorescence-based quantitation, was sensitive to the density of the immobilized probe sequence (FIG. 10). As described above, the density of DNA films prepared with different amounts of MgCl$_2$ present was monitored using fluorescein-modified oligonucleotides. As the amount of Mg$^{2+}$ in the deposition solution increases, the density of probe increases, with films with 11 pmol DNA/cm$^2$ obtained with 10 mM MgCl$_2$ and films with 27 pmol DNA/cm$^2$ obtained with 100 mM MgCl$_2$. The response obtained in the presence of Ru(NH$_3$)$_6^{3+}$ and Fe(CN)$_6^{3-}$ was also monitored, and increased with the surface coverage. With the film prepared with 10 mM MgCl$_2$, the average charge measured was 0.13(5) µC, while with 100 mM MgCl$_2$ present during probe deposition, the average charge measured was 0.59(5) µC. The correlation between these values and the density of probe DNA indicates that the electrochemical signal exhibits a direct dependence on the concentration of immobilized DNA present at the electrode surface.

When signal increases upon hybridization were monitored for the electrodes with different surface coverages, it was observed that films with lower probe densities permitted more efficient target capture (FIG. 10). This effect has been observed in several studies and is proposed to arise because of steric crowding when local concentrations of immobilized DNA are high. While the lowest density film studied here (formed with 10 mM MgCl$_2$) allowed 87(±5)% hybridization, the highest density film (formed with 100 mM MgCl$_2$) displayed a much lower level of hybridization with 6(±2)% efficiency. The films prepared with 50 mM MgCl$_2$ that were routinely used in the electrocatalysis assay also displayed only partial hybridization, with 7(±2)% of probes forming a complex with a target DNA sequence. It is noteworthy, however, that the electrocatalytic assay was able to resolve this low level of target complexation with a change in the integrated charge of typically >100%.

Based on the dimensions of duplex DNA, ~50 pmol/cm$^2$ is the maximal coverage of duplexes that can be achieved. Therefore, it is apparent that the coverage of single-stranded probe must be well below this level to achieve efficient hybridization.

Example 9

Detecting Targets Containing Single-base Substitutions

In experiments monitoring the hybridization of DNA oligonucleotides corresponding to a region of the *H. pylori* 23S rRNA, a pronounced sensitivity to mismatched base pairs within the target/probe complex was observed. The enhancement in the electrochemical signal typically observed with the WT rRNA sequence was significantly diminished when a sequence containing an A-to-C substitution at position 2143 was introduced (FIG. 9). The A2143C sequence is medically significant because this substitution imparts resistance to clarithromycin, the antibiotic typically used to combat *H. pylori*. Over 10% of the infections observed clinically are clarithromycin resistant.

Based on the thermal stabilities of the rRNA sequences used for these experiments, the observation of differential hybridization is surprising. The target/probe duplexes formed from the ribosomal sequences employed for this study exhibited T$_m$ values of 58(2)° C. when fully matched, and 52(2)° C. when the A2143C mutation was present that produced a C-T mismatch. Thus, it is reasonable to expect that both duplexes should be formed at the surface if the complexation was governed by thermodynamic stability.

Figure 11:
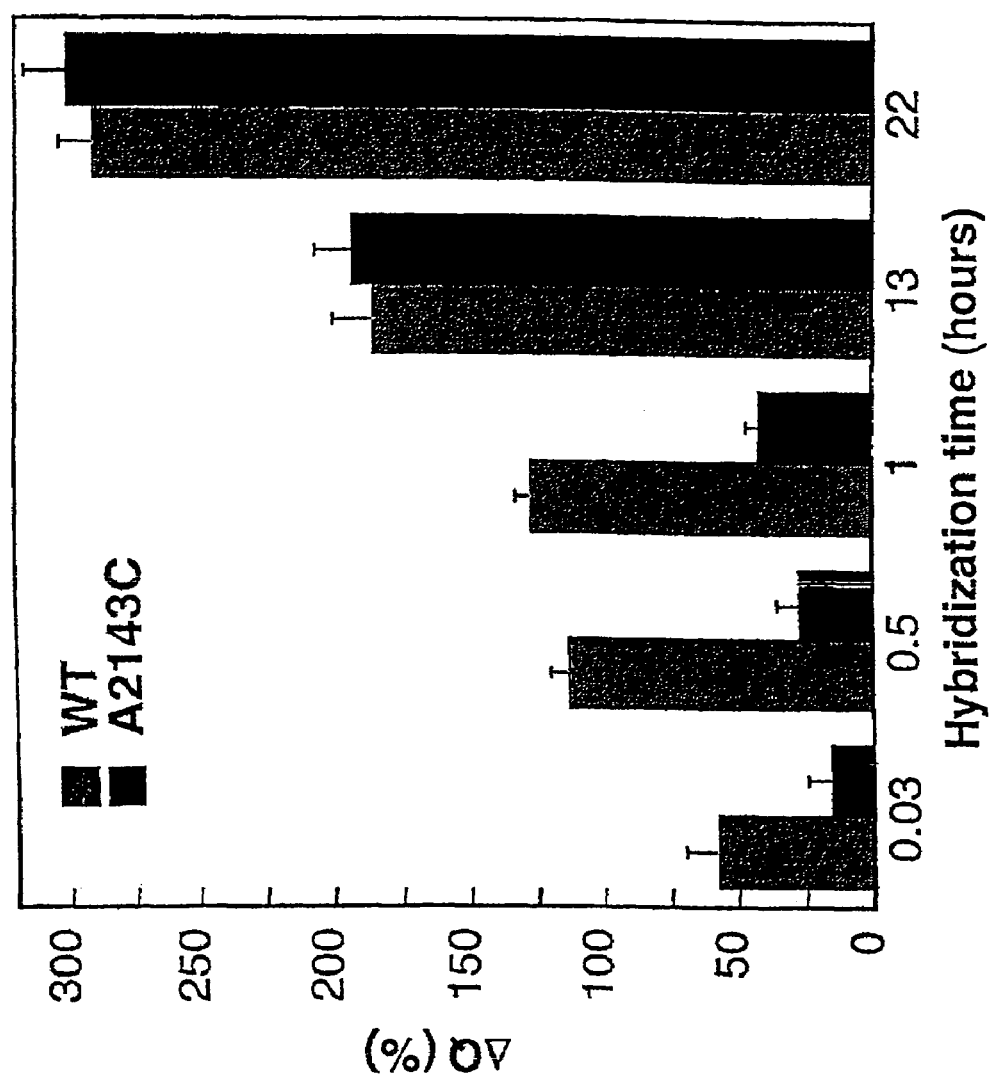
FIG. 11 shows time dependence of hybridization for WT and A2143C sequences corresponding to a fragment of the H. pylori 23S rRNA. Films of probe (HP2a) DNA were deposited from solutions containing 1 µM MCH, 5 µM ssDNA, and 0.8 M sodium phosphate (pH 7) for 1 hour at room temperature. Hybridization was performed with 1 µM target in 25 mM sodium phosphate (pH 7), 25 mM NaCl, and 100 mM $MgCl_2$ for the designated time. Electrodes were incubated at 40° C. during hybridization.

To investigate the origin of the differential hybridization observed in the presence of the point mutation, the time dependence of the hybridization was monitored (FIG. 11). With short incubation times, a pronounced difference in the signal obtained for the WT sequence was observed relative to the A2143C sequence. However, if the hybridization was permitted to proceed longer than 12 hours, comparable results were obtained with both sequences. Therefore, the discrimination of the A2143C mutation is a result of slower hybridization kinetics for the sequence that is mismatched with respect to the probe. The rate of association for both sequences is likely similar, thus the observed change may reflect a faster dissociation rate for the mismatched complex that limits the accumulation of hybridized duplexes.

Example 10

Detection of Extended DNA and RNA Targets

Figure 12:
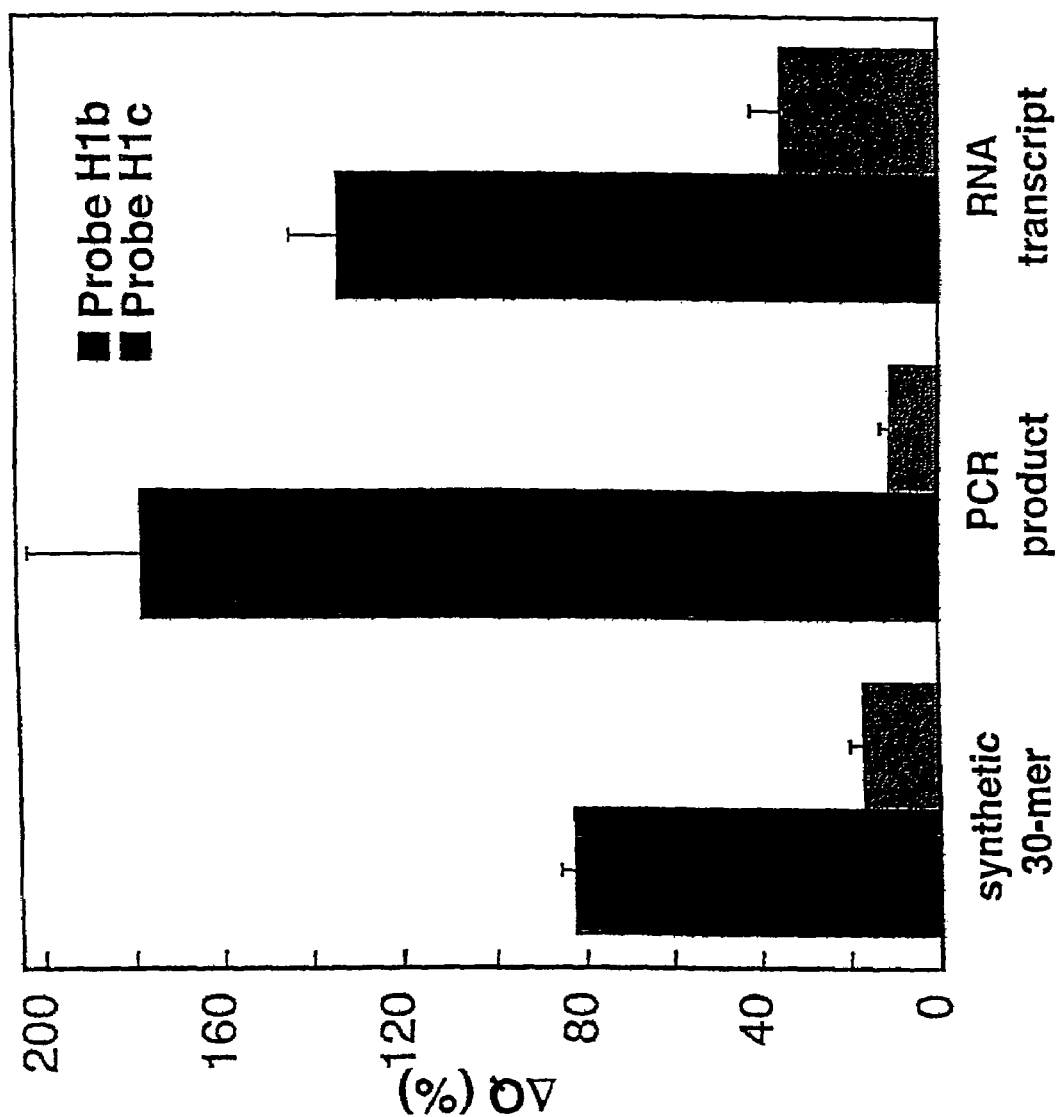
FIG. 12 shows electrocatalytic detection of extended DNA and RNA targets. DNA probe solutions (HP1b and HP1c) were deposited for 1.5 hours. Target solution containing synthetic 30-mer and PCR product contained 500 nM target, 100 mM $MgCl_2$, 25 mM sodium phosphate (pH 7), and 25 mM NaCl and were exposed to DNA films for 1 hour at 45° C. RNA target hybridization was under the same conditions except 1 µM RNA was used.

The applicability of the electrocatalytic assay to the detection of large DNA and RNA targets was tested using a >200 nucleotide sequence containing the *H. pylori* hpn gene (FIG. 12). For these hybridization experiments, probe sequences were employed containing a linker of 12 thymine residues that served to increase the accessibility of the portion of the oligonucleotide used for target capture. Using mild hybridization conditions (1 hour, 45° C.), single-stranded DNA made by asymmetric PCR and RNA generated in vitro was specifically detected via large increases in electrocatalytic currents obtained in the presence of a complementary probe. Low levels of non-specific binding were observed with a noncomplementary probe sequence, indicating that the increases in signal observed with the complementary probe resulted from the highly specific hybridization of the targets. It is noteworthy, however, that the RNA target reproducibly exhibited higher levels of nonspecific binding.

The electrocatalytic assay described here provides a sensitive means to detect nucleic acid sequences belonging to infectious pathogens with high specificity using electrochemical readout. The method is very sensitive, and is suitable for the detection of low levels of DNA hybridization from dilute solutions of target sequences. A particularly attractive feature of the method is the large signal enhancements that result from formation of duplex DNA on the electrode surface. Typically, the changes in integrated charge observed are greater than 100% even though the extent of hybridization at the electrode surface can be as low as 5-10%. Moreover, the unexpected finding that a single point mutation drastically attenuates the kinetics of duplex formation at the electrode surface indicates that hybridization-based bacterial genotyping is feasible, and that high-resolution sequence discrimination can be achieved with immobilized DNA probes. The further development of electrochemical tools such as the assay reported here that can be adapted for high-throughput analysis of DNA will enable efficient analysis of bacterial and human genes.

References

1. M. M. Shi, "Technologies for individual genotyping: detection of genetic polymorphisms in drug targets and disease genes". *Am. J. Pharmacogenomics* 2002, 2, 197-205.
2. W. Vercoutere, and M. Akeson, "Biosensors for DNA sequence detection". *Curr. Opin. Chem. Biol.* 2002, 6, 816-822.
3. B. P. Nelson, M. R. Liles, K. B. Frederick, R. M. Corn, and R. M. Goodman, "Label-free detection of 16S ribosomal RNA hybridization on reusable DNA arrays using surface plasmon resonance imaging". *Environ. Microbiol.* 2002, 4, 735-743.
4. B. P. Nelson, T. E. Grimsrud, M. R. Liles, R. M. Goodman, and R. M. Corn, "Surface plasmon resonance imaging measurements of DNA and RNA hybridization adsorption onto DNA microarrays". *Anal. Chem.* 2001, 73, 1-7.
5. E. M. Southern, "DNA microarrays. History and overview". *Methods Mol. Biol.* 2001, 170, 1-15.
6. J. Wang, "From DNA biosensors to gene chips". *Nucleic Acids Res.* 2000, 28, 3011-3016.
7. K. M. Millan, and S. R. Mikkelsen, "Sequence-selective biosensor for DNA based on electroactive hybridization indicator". *Anal. Chem.* 1993, 65, 2317-2323.
8. K. Hashimoto, K. Ito, and Y. Ishimori, "Sequence-specific gene detection with gold electrode modified with DNA probes and an electrochemically active dye." *Anal. Chem.* 1994, 66, 3830.
9. K. Hashimoto, K. Ito, and Y. Ishimori, "Novel DNA sensor for electrochemical gene detection." *Anal. Chem. Acta.* 1994, 286, 219.
10. X.-H. Xu, H. C. Yang, T. E. Mallouk, and A. J. Bard, "Immobilization of DNA on an Aluminum(III) Alkanebisphosphonate Thin Film with Electrogenerated Chemiluminescent Detection". *J. Am. Chem. Soc.* 1994, 116, 8386-8387.
11. S. Liu, M. Wang, P. He, and Y. Fang, "Voltammetric determination of sequence-specific DNA by electroactive intercalator on graphite electrode". *Anal. Chim. Acta* 1996, 335, 239-243.
12. C. A. Mirkin, R. L. Letsinger, R. C. Mucic, and J. J. Storhoff, "A DNA-based method for rationally assembling nanoparticles into macroscopic materials". *Nature* 1996, 382, 607-609.
13. M. E. Napier, C. R. Loomis, M. F. Sistare, J. Kim, A. E. Eckhardt, and H. H. Thorp, "Probing biomolecule recognition with electron transfer: electrochemical sensors for DNA hybridization". *Bioconj. Chem.* 1997, 8, 906-913.
14. S. O. Kelley, E. M. Boon, J. K. Barton, N. M. Jackson, and M. G. Hill, "Single-base mismatch detection based on charge transduction through DNA". *Nucl. Acids Res.* 1999, 27, 4830-4837.
15. P. A. Ropp, and H. H. Thorp, "Site-selective electron transfer from purines to electrocatalysts: voltammetric detection of a biologically relevant deletion in hybridized DNA duplexes". *Chem. Biol.* 1999, 6, 599-605.
16. E. M. Boon, D. M. Ceres, T. G. Drummond, M. G. Hill, and J. K. Barton, "Mutation detection by electrocatalysis at DNA-modified electrodes." *Nat. Biotech.* 2000, 18, 1096.
17. M. I. Pividori, A. Merkoci, and S. Alegret, "Electrochemical genosensor design: immobilization of oligonucleotides onto transducer surfaces and detection methods". *Biosens. Bioelect.* 2000, 15, 291-303.
18. T. A. Taton, C. A. Mirkin, and R. L. Letsinger, "Scanometric DNA array detection with nanoparticle probes". *Science* 2000, 289, 1757-1760.
19. R. J. Heaton, A. W. Peterson, and R. M. Georgiadis, "Electrostatic surface plasmon resonance: direct electric field-induced hybridization and denaturation in monolayer nucleic acid films and label-free discrimination of base mismatches". *Proc. Natl. Acad. Sci. U.S.A.* 2001, 98, 3701-3704.
20. A. W. Peterson, R. J. Heaton, and R. M. Georgiadis, "The effect of surface probe density on DNA hybridization". *Nucl. Acids Res.* 2001, 29, 5163-5168.
21. P. M. Armistead, and H. H. Thorp, "Electrochemical detection of gene expression in tumor samples: overexpression of Rak nuclear tyrosine kinase". *Bioconj. Chem.* 2002, 13, 172-176.
22. A. W. Peterson, L. K. Wolf, and R. M. Georgiadis, "Hybridization of mismatched or partially matched DNA at surfaces". *J. Am. Chem. Soc.* 2002, 124, 14601-14607.
23. E. Palecek, M. Fojta, M. Tomschik, and J. Wang, "Electrochemical biosensors for DNA hybridization and DNA damage". *Biosens. Bioelectron.* 1998, 13, 621-628.
24. H. H. Thorp, "Cutting out the middleman: DNA biosensors based on electrochemical oxidation." *Trends in Biotechnology* 1998, 16, 117-121.
25. B. J. Taft, M. M. O'Keefe, J. T. Fourkas, and S. O. Kelley, "Engineering DNA-electrode connectivities: effect of linker length and structure". *Anal. Chim. Acta* 2003, in press.
26. A. B. Steel, T. M. Heme, and M. J. Tarlov, "Electrochemical quantitation of DNA immobilized on gold". *Anal. Chem.* 1998, 70, 4670-4677.
27. S. Wang, A. E. Friedman, and E. T. Kool, "Origins of high sequence selectivity: a stopped-flow kinetics study of DNA/RNA hybridization by duplex- and triplex-forming oligonucleotides". *Biochemistry* 1995, 34, 9774-9784.

All patents, patent applications, and published references cited herein are hereby incorporated by reference in their entirety. While this invention has been particularly shown and described with references to preferred embodiments thereof, it will be understood by those skilled in the art that various changes in form and details can be made therein without departing from the scope of the invention encompassed by the appended claims.

Example 11

Preparation of Nanoelectrode Ensembles for Detection of Nucleic Acids

Electroless Gold Deposition

Track-etch polycarbonate filters obtained from Osmonics, Inc were used as membrane templates. These membranes are 6 mm thick with a nominal pore diameter of 10 nm and a pore density of $5.2 \times 10^8$ pores $cm^2$. The NEEs were prepared using the electroless plating procedure reported previously (1) with slight modifications (2). The template membrane was immersed into methanol for 2 hours and then immersed for 45 min in a solution that is 0.026 M in SnCl2 and 0.07 M in trifluoroacetic acid in 50:50 methanol/water as the solvent. This results in deposition of the "sensitizer" ($Sn^{2+}$) onto all membrane surfaces (both the pore walls and the membrane faces). The membrane was rinsed twice in methanol for 2.5 min and immersed into a solution of AgNO3 (0.029 M) in aqueous ammonia for 10 min. This results in the deposition of nanoparticles of Ag on all membrane surfaces. Membranes were then rinsed in methanol for 5 min. After treatment in AgNO3, the membrane was placed in a gold-plating mixture containing 0.5 mL of the commercial gold-plating solution Oromerse Part B (Technic Inc., 0.127 M in Na2SO3, 0.625 M in formaldehyde, and 0.025 M in NaHCO3). The temperature of this bath was maintained at ~4° C. The pH is initially 12, but was adjusted to 10 by dropwise addition of 0.5 M H2SO4, with constant stirring. Membranes were placed in the gold-plating bath for 24 hours resulting in the deposition of Au nanowires into the pores. After plating, the membrane was rinsed with water and then immersed in 10% HNO3 for 12 hours. The membrane was then thoroughly rinsed in water and air-dried.

Assembly of 2D NEEs

The 2D NEEs obtained via the electroless gold deposition method described above were assembled as reported previously (1) with slight modifications (3). A small piece of the gold plated membrane was first affixed to a piece of adhesive copper tape with the "shiny" side of the gold surface facing up and the rough face of the membrane facing the adhesive. Another strip of adhesive copper was then affixed to the upper shiny gold surface and covered only small part of the membrane. This improved the yield of making reproducible NEEs as well as electrical connection between the copper and the NEEs. The Au upper surface layer that was not covered by the Cu foil tape was then removed by simply applying and removing a strip of 3M Scotch tape (brand Magic tape No. 810). This step exposes the disc shaped ends of Au nanowires. The NEE assembly was then heated at 155° C. for 30 min. Membranes were then insulated with 3M Scotch brand No. 898 tape on the lower and upper surfaces of the assembly as well as Cu foil tape. Prior to placement on the assembly, a 0.07 $cm^2$ hole was punched in the upper piece of Scotch tape. This aperature defines the geometric area of the 2D NEEs exposed to solution.

Preparation and Assembly of 3D NEEs

After the electroless deposition of gold within the polycarbonate membrane pores as well as both faces of the membrane, the 3D NEEs were prepared by O2 plasma etching the 2D NEEs as described (4). The "shiny" side (5) of the gold surface was removed by applying and removing a strip of 3M Scotch tape which exposed the ends of the gold nanowires. The "shiny" membrane surface was O2 plasma etched using a Plasma Therma 290 Series System VII for 65 seconds. This process etches away the polycarbonate material and exposes ~200 nm of the gold nanowire ends. The etching conditions were as follows: power=100 W, oxygen pressure=150 mTorr, flow rate=30 $cm^3$ min−1. The 3D NEEs were assembled as the 2D NEEs described above and heat treated in the oven at 155° C. for 30 min to improve sealing of the polycarbonate membrane around NEEs. This fabrication process increased significantly the yield of functional 3D NEEs to ~85%. The geometric area of the 3D NEEs exposed to solution was 0.07 $cm^2$.

FIG. 13A shows scanning electron micrographs of the structures generated using a modified version of an electroless plating method previously described.[2] These twodimensional (2D) nanoelectrodes are approximately 10 nm in diameter and have an average separation of 200 m-n. Using oxygen plasma etching to remove a thin layer of polycarbonate, 5 the same materials are used to prepare threedimensional (3D) NEEs featuring exposed Au nanowires. Plasma etching resulted in consistent exposure of ~200 nm of the gold nanowires. Sealing of the polycarbonate membrane around the NEEs was achieved by heat treatment, and was a crucial step that significantly reduced the double-layer charging currents.[2]

Modification of Gold Surfaces with DNA Probe and DNA Hybridization Protocol

BAS macrodisc gold electrodes were polished prior to use with 0.05 mm alumina powder using a polishing wheel. The macrodisc gold electrodes were then rinsed with Millipore water, sonicated for 5 min. and etched by scanning from 0-1800 mV at 200 mV/s in 1M H2SO4, and rinsed with copious amounts of Millipore water. The ss-thiolated-DNA probes were immobilized on BAS macrodisc gold electrodes, 2D, and 3D NEEs. The electrodes were exposed to solutions containing 5 mM SH-DNA, 500 nM 6-mercapto-1-hexanol (97%), 25 mM sodium phosphate (pH=7), 25 mM NaCl and 50 mM MgCl2 in a humidity chamber at room temperature for 1 hour. Electrodes were then rinsed in 25 mM sodium phosphate/25 mM NaCl (pH=7). The chemisorption of DNA onto gold electrodes was confirmed by scanning from 0-500 mV in a solution of 2 mM ferricyanide in 25 mM sodium phosphate (pH=7)/25 mM NaCl at a scan rate of 100 mV/s. Electrodes were then rinsed in 25 mM sodium phosphate/25 mM NaCl (pH=7) and electrocatalysis currents were measured as described above. Solutions containing 1 pM-20 mM target DNA in 25 mM sodium phosphate (pH=7), 25 mM NaCl, and 100 mM MgCl2 were then introduced in a thermostatted humidity chamber at 37-40° C. Electrocatalytic current was then remeasured as described above.

Figure 13B:
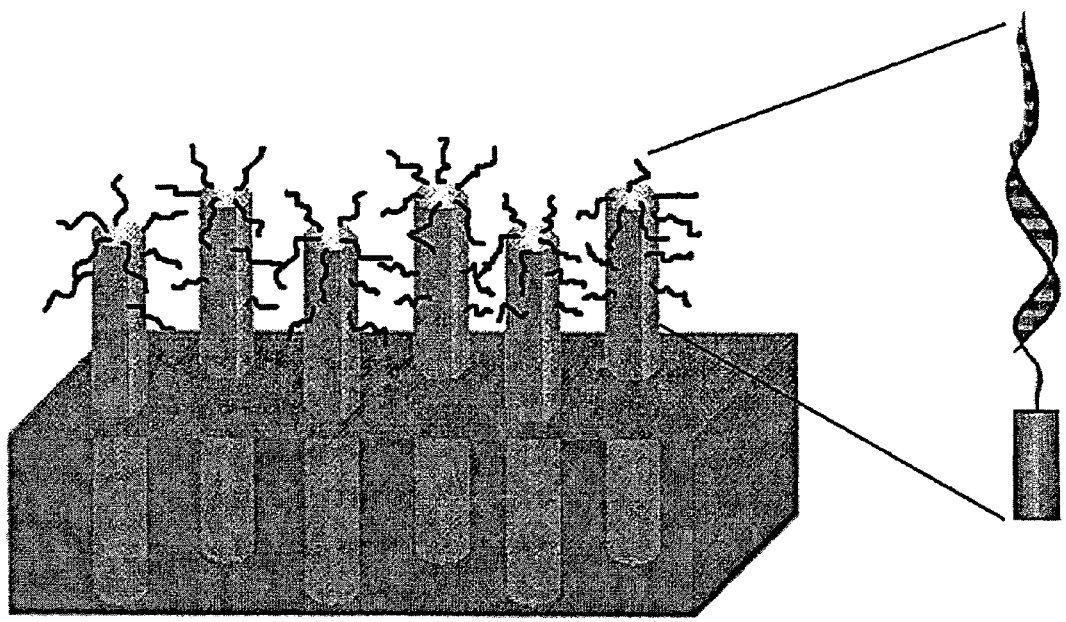
FIG. 13B shows nanowires with nucleic acid probes attached thereto.

FIG. 13B shows schematically the attachment of the nucleic acid probes on the nanowires.

Oligonucleotide Synthesis and Purification

Oligonucleotide synthesis was performed with an ABI 394 DNA/RNA synthesizer using standard automated solid-phase techniques (6). The DNA 5'-terminus was modified with a thiol linker and purified by reverse phase HPLC as described previously (7). DNA sequences belonging to the pathogenic microbe *Helicobacter pylori* were as follows:

```
Probe:                              (SEQ ID NO. 18)
SH-5'GGGTCTTTCCGTCTTGCC3'

Target:                             (SEQ ID NO. 19)
5'GGCAAGACGGAAAGACCC3'

Control                             (SEQ ID NO. 20)
(noncomplementary) target:
5'GCACTAGCGATAGTCATC3'
```

Oligonucleotides were quantified by measuring absorbance at 260 nm using extinction coefficients reported previously (8).

Example 12

Electrochemical Measurements of Nucleic Acids

Methods

Cyclic voltammetry measurements performed using a Bioanalytical Systems (BAS) Epsilon potentiostat/galvanostat controlled with BAS Epsilon EC software. All measurements were conducted with a three-electrode configuration at room temperature. An Ag/AgCl electrode equipped with a Luggin capillary was used as the reference electrode, and a platinum wire was used as the counter electrode. BAS gold macroelectrodes (area=0.02 cm2), 2D and 3D NEEs were used as working electrodes. All potentials are reported vs. Ag/AgCl. Electrocatalytic currents were measured in solutions of 5 mM $Fe(CN)_6^{3-}$ and 100 mM $Ru(NH_3)_6^{3+}$ in 25 mM sodium phosphate/250 mM NaCl (pH=7) at a scan rate of 100 mV/s. Cathodic charge (Q) was quantitated by integrating the area under each voltammogram, and signal changes corresponding to hybridization events were calculated as follows $$DQ\% = \{((Q\text{final} - Q\text{initial})/Q\text{initial})*100\}$$

where Qfinal and Qinitial represent integrated cathodic charges after and before the hybridization, respectively. All electrochemical measurements were performed on at least 3 different gold electrodes and integrated charge with standard deviations are reported in Table 1.

References

1. Menon V. P.; Martin C. R. *Anal. Chem.* 1995, 67, 1920.
2. Brunetti B.; Ugo P.; Moretto L. M.; Martin C. R. *J. Elecanal. Chem.* 2000, 491, 166.
3. Moretto L. M.; Pepe N.; Ugo P. *Talanta* 2004, 62, 1055.
4. Yu S.; Li N.; Wharton J.; Martin C. R. *Nano Lett.* 2004, 3, 815.
5. Cheng I. F.; Whiteley L. D.; Martin C. R. *Anal. Chem.* 1989, 61, 762.
6. Beaucage S. L.; Caruthers M. H.; *Tetrahedron Lett.* 1981, 22, 1859.
7. Taft B. J.; O'Keefe M. O.; Fourkas J. T.; Kelley S. O. *Anal. Chim. Acta.* 2003, 496, 81.
8. Lapierre M. A.; O'Keefe M. M.; Taft B. J.; Kelley S. O. *Anal. Chem.* 2003, 75, 6327.
9. Kelley S. O.; Boon E. M.; Jackson N. M.; Hill M. G.; Barton J. K. *Nucleic Acids Res.*, 1999, 27, 4830.
10. Kelley S. O., Hill M. G. *Frontiers in Electrochemistry: Bioinorganic Electrochemistry;* Kluwer Academic Publishers: in press 2004.

Results

Figure 14:
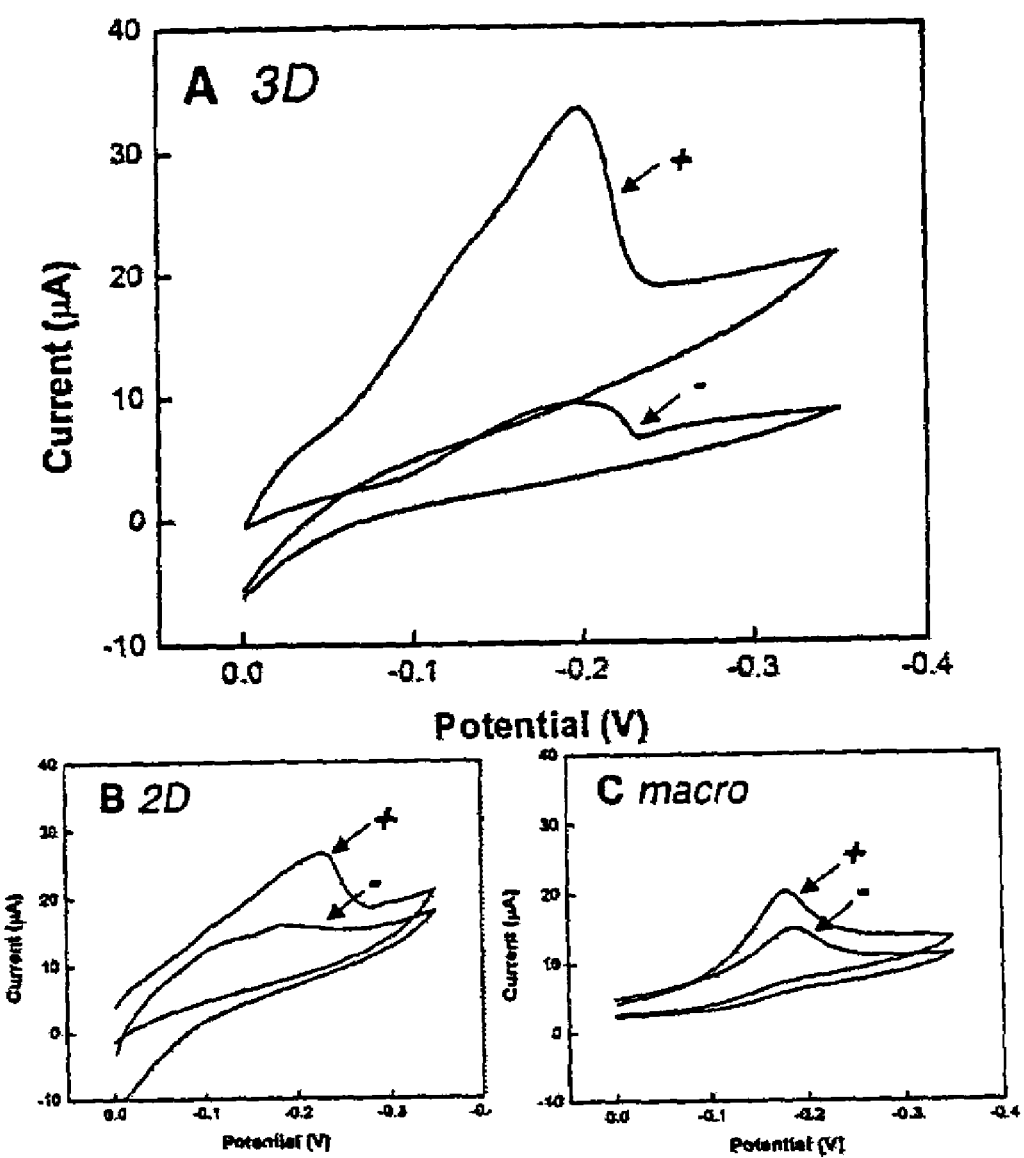
FIG. 14 shows cyclic voltammograms for Ru(III)/Fe(III) electrocatalysis at (A) 2D NEEs, (B) 2D NEEs, and (C) Au macroelectrodes in the absence (−) and presence of (+) a DNA oligonucleotide complementary to the immobilized probe. Data shown was obtained at a scan rate of 100 mV/s.

As shown in FIG. 14, the electrocatalysis signals obtained using NEEs exhibit large increases upon the hybridization of a target DNA sequence.[9] While very small currents are measured at probe-modified NEEs relative to macroelectrodes, the signals observed upon DNA hybridization at NEEs approach or surpass those obtained with Au macroelectrodes (Table 1 and FIG. 14).10 To quantitate the effect of DNA hybridization on the signals obtained with different electrodes, DQ values (reflecting integrated electrocatalysis currents before and after introduction of the target oligonucleotide)l were compared for 2D NEEs, 3D NEEs, and macroelectrodes. Average values of 730%, 420%, and 80% were obtained (Table 1), respectively. Thus, the electrocatalytic signals measured at NEEs were more strongly modulated by DNA hybridization relative to those observed at macroelectrodes. Control experiments where noncomplementary sequences were tested did not generate significant changes in the electrochemical response measured with any of the electrodes, indicating that the signal changes observed reflect the formation of a specific complex between target and probe.

TABLE 1

Comparison of electrochemical signals obtained at macro and nanoelectrodes

| Electrode | ΔQ %* | Q (μC)* | Genometric are (cm²)* |
|---|---|---|---|
| Au macro | 80 ± 10 | 6.6 ± 0.6 | 0.02 |
| 2D NEE | 730 ± 80 | 8.5 ± 0.5 | 0.07 |
| 3D NEE | 420 ± 9- | 13 ± 4 | 0.07 |

*See footnote 11. Integrated chare after hybridization. The genometric area of the NEEs is defined by the exposed area of the nanowire ensemble.

The success of the DNA hybridization experiments conducted using NEEs clearly indicates that these nanostructures are useful substrates for biosensing. While both types of NEEs exhibited positive signal changes when a target DNA strand was present, several differences in the behavior of these electrodes were observed that indicated that the 3D nanostructures were more suitable for practical applications. The electrocatalysis currents measured at 3D NEEs were larger than at 2D NEEs, consistent with the increased active surface area produced by etching of the polycarbonate substrate.[12] Moreover, the etching process used to generate the exposed nanowires increased the yield of functional electrodes obtained from a single membrane (85% for 3D and 45% for 2D NEEs), and produced electrodes with smaller capacitive currents and more stable background signals during DNA hybridization experiments.

Figure 15:
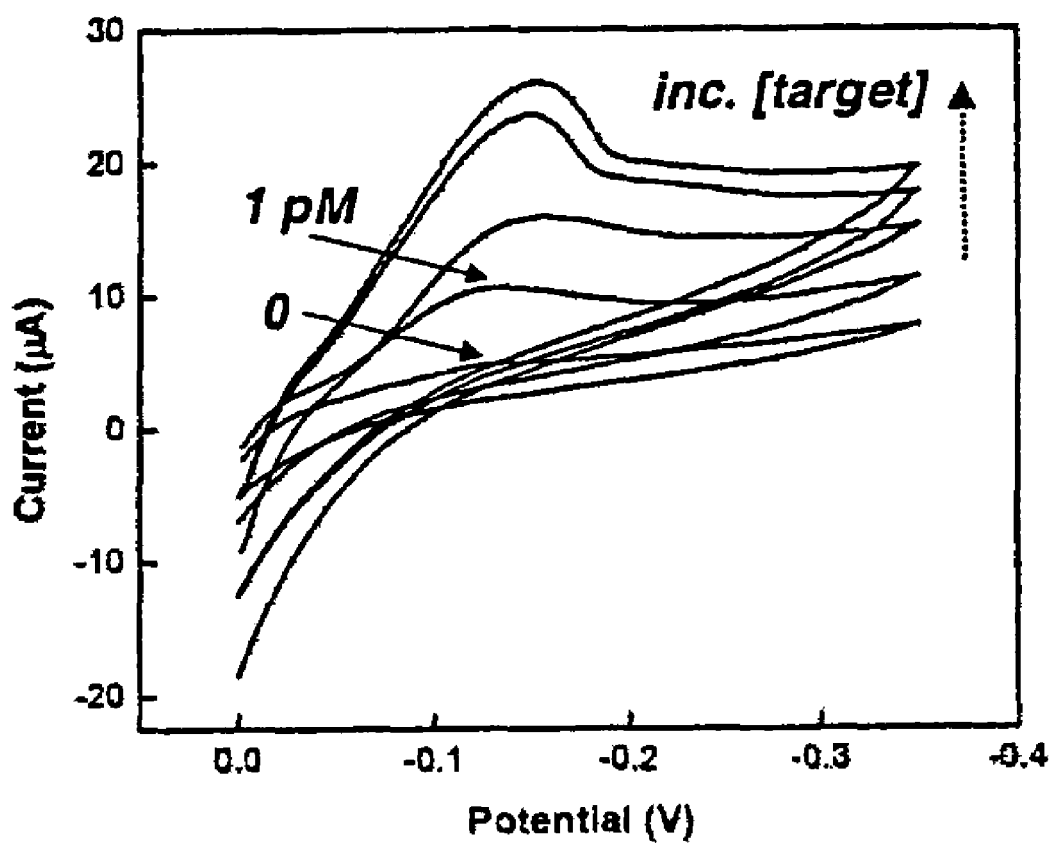
FIG. 15 shows evaluation of DNA detection limit at a 3D NEE using cyclic voltammetry. Data shown correspond to 0, 1 pM, 1 nM, 1 µM and 20 µM target DNA.

The 3D NEEs were used to establish the sensitivity of the electrocatalytic DNA detection assay performed on the nanoscale architecture (FIG. 15). When a probe-modified 3D NEE electrode was titrated with a target DNA strand, solutions containing picomolar concentrations of the analyte produced detectable changes in the electrochemical signal. Indeed, a sample containing 5 attomoles of target DNA increased the electrocatalysis signal by >200%. This analysis was performed on an electrode with an exposed geometric area of 0.07 cm², indicating that zeptomole detection limits could easily be achieved with a modest decrease in the size of the aperture used in the electrochemical analysis. Previous studies that used the Ru(III)/Fe(III) electrocatalysis assay to detect the same DNA sequences using macroscopic gold electrodes achieved femtomole senstivity.[4] An attomole-level detection limit compares favorably with recently reported electrochemical methods for the direct detection of oligonucleotides.[13] It is clear that the nanoelectrodes tested here are an attractive platform for biomolecular sensing because of the lowered detection levels and the enhanced amplification of the positive signal changes that occur upon DNA hybridization.

REFERENCE AND FOOTNOTES 1. (a) Li, C.; Papadopoulos, C.; Xu J. M. *Appl. Phys. Lett.* 1999, 75, 367. (b) Gooding, J. J.; Wibowo, R.; Liu, J.; Yang, W.; Losic, D.; Orbons, S.; Mearns, F. J.; Shapter, J. G.; Hibbert, D. B. *J. Am. Chem. Soc.* 2003, 125, 9006.
2. (a) Menon, V. P.; Martin, C. R. *Anal. Chem.* 1995, 67, 1920. (b) Brunetti, B.; Ugo P.; Moretto, L. M.; Martin, C. R. *J. Electroanal. Chem.* 2000, 491, 166. (c) Moretto, L. M.; Pepe, N.; Ugo, P. *Talanta* 2004, 62, 1055.
3. Forrer, P.; Schlottig, F.; Siegenthaler, H.; Textor, M. *J. Appl. Electrochem.* 2000, 30, 533.
4. Lapierre, M. A.; O'Keefe, M. M.; Taft, B. J.; Kelley, S. O. *Anal. Chem.* 2003, 75, 6327.
5. Yu, S.; Li, N.; Wharton, J.; Martin, C. R. *Nano Lett.* 2004, 3, 815.
6. Steele, A. B.; Heme, T. M.; Tarlov, M. J. *Anal. Chem.* 1998, 70, 4670.
7. Blaser, J.; *J. Infect. Dis.,* 1990, 161, 626.
8. Taft, B. J.; O'Keefe, M. O.; Fourkas, J. T.; Kelley, S. O. *Anal. Chim. Acta.* 2003, 496, 81.
9. See supplemental info for hybridization conditions and sequences.
10. Currents measured at 3D NEEs were typically ~2 fold higher than those measured at 2D NEEs. The surface area of exposed Au on 3D NEEs (A=0.025 cm2) should be increased by a factor of ~850 over 2D NEEs (A=2.9×10−5 cm2), based on areas approximated from SEM images. However, depletion of the diffusion layer between adjacent 3D nanostructures has previously been observed to decrease the participation of exposed sidewalls in electrochemical processes.3 This effect may be responsible for the relatively small signal increases that are observed at 3D relative to 2D NEEs in our assay.
11. Signal changes were calculated as follows. DQ (%/)={((Qfinal−Qinitial)/Qinitial)*100} where Qfinal and Qinitial are integrated cathodic charges after and before DNA hybridization, respectively.
12. The currents observed at NEEs are larger than what would be predicted based on the active surface areas of these structures.11 However, strong electric fields are predicted to exist around the NEEs which may facilitate the reduction of $Ru(NH)_6^{3+}$ through favorable electrostatic interactions. (Smith, C. P.; White, H. S.; *Anal. Chem.* 1993, 65, 3343.)
13. (a) Thorp, H. H.; *Trends Biotechnol.* 1998, 16, 117. (b) Armistead, P. M.; Thorp, H. H. *Anal. Chem.* 2000, 72, 3764. (c) Gore, M. R.; Szalai, V. A.; Ropp, P. A.; Yang, I. V.; Silverman, J. S.; Thorp H. H. *Anal. Chem.* 2003, 75, 6586. (d) Patolsky, F.; Lichtenstetin, A.; Kotler, M.; Willner, I. Angew. *Chem. Int. Ed. Engl.* 2001, 40, 2261. (e) Wang, J.; Polsky, R.; Merkoci, A.; Turner, L. *Langmuir,* 2003, 19, 989.

What we claim:

1. A method of detecting nucleic acid hybridization between a nucleic acid probe and a target nucleic acid in a sample, the method comprising:
   (a) providing a nucleic acid probe immobilized on nanoelectrode ensembles;
   (b) contacting under hybridization conditions the nanoelectrode ensembles and the immobilized nucleic acid probe with the sample and a redox pair comprising (i) a nucleic acid binding compound comprising a first transition metal complex that interacts electrostatically with the nucleic acid probe, and (ii) a redox-active probe comprising a second transition metal complex; wherein the sample and redox pair are in solution; and
   (c) measuring an electrocatalytic signal generated by hybridization of the nucleic acid probe and the target nucleic acid in the sample, wherein an increase of the signal detected relative to a signal of a control sample comprising no target nucleic acid, indicates hybridization between the nucleic acid probe and the target nucleic acid, and wherein a decrease in the signal detected relative to that of perfect complementarity between the nucleic acid probe and the target nucleic acid indicates a mismatch between the nucleic acid probe and the target nucleic acid.

2. The method of claim 1, wherein the first transition metal complex comprises a metal selected from the group consisting of cobalt, iron, molybdenum, osmium, ruthenium and rhenium.

3. The method of claim 1, wherein the first transition metal complex is a transition metal ammonium complex.

4. The method of claim 1, the nanoelectrode ensembles comprise a gold nanowire.

5. The method of claim 1, wherein the second transition metal complex comprises a metal selected from the group consisting of iron, cobalt, molybdenum, iridium, osmium and rhenium.

6. The method of claim 1, wherein the second transition metal complex is a transition metal cyanate or chloride complex.

7. The method of claim 1, wherein the nucleic acid probe comprises DNA.

8. The method of claim 1, wherein the target nucleic acid comprises DNA.

9. The method of claim 1, wherein the target nucleic acid comprises RNA.

10. A method of detecting nucleic acid hybridization between a first nucleic acid and a second nucleic acid, the method comprising:
   (a) providing the first nucleic acid immobilized on nanoelectrode ensembles;
   (b) contacting under hybridization conditions the nanoelectrode ensembles and the immobilized first nucleic acid with a solution suspected of containing the second nucleic acid and containing a redox pair comprising (i) a first transition metal complex that interacts electrostatically with the nucleic acids, and (ii) a redox-active probe comprising a second transition metal complex; and
   (c) measuring an electrocatalytic signal generated by hybridization of the first nucleic acid and the second nucleic acid, wherein an increase of the signal detected relative to a signal of a control sample comprising no second nucleic acid, indicates that the nucleic acid hybridization between the first nucleic acid and the second nucleic acid, and wherein a decrease in the signal detected relative to that of perfect complementarity between the first and second nucleic acids indicates a mismatch between the first nucleic acid and the second nucleic acid.

11. The method of claim 10, wherein the first transition metal complex comprises a metal selected from the group consisting of cobalt, iron, molybdenum, osmium, ruthenium and rhenium.

12. The method of claim 10, wherein the first transition metal complex is a transition metal ammonium complex.

13. The method of claim 10, wherein the nanoelectrode ensembles comprise a gold nanowire.

14. The method of claim 10, wherein the second transition metal complex comprises a metal selected from the group consisting of iron, cobalt, molybdenum, iridium, osmium and rhenium.

15. The method of claim 10, wherein the second transition metal complex is a transition metal cyanate or chloride complex.

16. The method of claim 10, wherein the nucleic acid probe comprises DNA.

17. The method of claim 10, wherein the target nucleic acid comprises DNA.

18. The method of claim 10, wherein the target nucleic acid comprises RNA.

19. A method of detecting nucleic acid hybridization between a nucleic acid probe and a target nucleic acid in a sample, the method comprising:
   (a) providing a nucleic acid probe immobilized on nanoelectrode ensembles;
   (b) contacting under hybridization conditions the nanoelectrode ensembles and the immobilized nucleic acid probe with the sample and a redox pair comprising a first transition metal complex that interacts electrostatically with the nucleic acid probe, and a redox-active probe comprising an ascorbic acid or tripropylamine, wherein the sample and the redox pair are in solution; and
   (c) measuring an electrocatalytic signal generated by hybridization of the nucleic acid probe and the target nucleic acid in the sample, wherein an increase of the signal detected relative to a signal of a control sample comprising no target nucleic acid, indicates that the nucleic acid hybridization between the nucleic acid probe and the target nucleic acid, and wherein a decrease in the signal detected relative to that of perfect complementarity between the nucleic acid probe and the target nucleic acid indicates a mismatch between the nucleic acid probe and the target nucleic acid.

20. The method of claim 19, wherein the first transition metal complex comprises a metal selected from the group consisting of cobalt, iron, molybdenum, osmium, ruthenium and rhenium.

21. The method of claim 19, wherein the first transition metal complex is a transition metal ammonium complex.

22. The method of claim 19, the nanoelectrode ensembles comprise a gold nanowire.

23. The method of claim 19, wherein the nucleic acid probe comprises DNA.

24. The method of claim 19, wherein the target nucleic acid comprises DNA.

25. The method of claim 19, wherein the target nucleic acid comprises RNA.

26. A method of detecting nucleic acid hybridization between a first nucleic acid and a second nucleic acid, the method comprising:
   (a) providing the first nucleic acid immobilized on nanoelectrode ensembles;
   (b) contacting under hybridization conditions the nanoelectrode ensembles and the immobilized first nucleic acid with a solution suspected of containing the second nucleic acid and containing a redox pair comprising (i) a first transition metal complex that interacts electrostatically with the nucleic acids, and (ii) a redox-active probe comprising an ascorbic acid or tripropylamine; and
   (c) measuring an electrocatalytic signal generated by hybridization of the first nucleic acid and the second nucleic acid, wherein an increase of the signal detected relative to a signal of a control sample comprising no second nucleic acid, indicates that the nucleic acid hybridization between the first nucleic acid and the second nucleic acid, and wherein a decrease in the signal detected relative to that of perfect complementarity between the first and second nucleic acids indicates a mismatch between the first nucleic acid and the second nucleic acid.

27. The method of claim 26, wherein the first transition metal complex comprises a metal selected from the group consisting of cobalt, iron, molybdenum, osmium, ruthenium and rhenium.

28. The method of claim 26, wherein the first transition metal complex is a transition metal ammonium complex.

29. The method of claim 26, wherein the nanoelectrode ensembles comprise a gold nanowire.

30. The method of claim 26, wherein the first nucleic acid comprises DNA.

31. The method of claim 26, wherein the second nucleic acid comprises DNA.

32. The method of claim 26, wherein the second nucleic acid comprises RNA.

* * * * *

UNITED STATES PATENT AND TRADEMARK OFFICE
CERTIFICATE OF CORRECTION

| | | |
|---|---|---|
| PATENT NO. | : 7,741,033 B2 | Page 1 of 1 |
| APPLICATION NO. | : 10/913925 | |
| DATED | : June 22, 2010 | |
| INVENTOR(S) | : Shana O. Kelley et al. | |

It is certified that error appears in the above-identified patent and that said Letters Patent is hereby corrected as shown below:

In the Specification:

At column 1, after the title GOVERNMENT SUPPORT, delete lines 16-18 and insert --The invention was made with government support under grant number NIH R21-CA 097945 awarded by the National Institutes of Health and under grant number F49620-03-1-0365 awarded by USAF/AFOSR. The United States Government has certain rights in the invention.--

In the Claims:

At column 51, claim 16, line 48, delete "the nucleic acid probe" and insert --the first nucleic acid--.

At column 51, claim 17, line 50, delete "the target nucleic acid" and insert --the second nucleic acid--.

At column 51, claim 18, line 52, delete "the target nucleic acid" and insert --the second nucleic acid--.

Signed and Sealed this

Thirty-first Day of August, 2010

David J. Kappos
*Director of the United States Patent and Trademark Office*